United States Patent [19]

Longley et al.

[11] Patent Number: 5,298,523
[45] Date of Patent: Mar. 29, 1994

[54] METHOD FOR TREATING TRANSPLANT PATIENTS USING MYCALAMIDE COMPOUNDS

[75] Inventors: Ross E. Longley, Vero Beach, Fla.; Glynn T. Faircloth, Cambridge, Mass.

[73] Assignee: Harbor Branch Oceanographic Institution, Inc., Fort Pierce, Fla.

[21] Appl. No.: 990,156

[22] Filed: Dec. 14, 1992

[51] Int. Cl.$^5$ .................... A61K 31/35; A01N 43/32
[52] U.S. Cl. .................................. 514/452; 514/456
[58] Field of Search ........................ 514/452, 456

[56] References Cited

U.S. PATENT DOCUMENTS

| | | | |
|---|---|---|---|
| 4,548,814 | 10/1985 | Rinehart, Jr. | 424/95 |
| 4,729,996 | 3/1988 | Wright et al. | 514/215 |
| 4,737,510 | 4/1988 | Rinehart, Jr. | 514/388 |
| 4,808,590 | 2/1989 | Higa et al. | 514/272 |
| 4,868,204 | 9/1989 | Blunt | 514/452 |

FOREIGN PATENT DOCUMENTS 9117172  11/1991  PCT Int'l Appl. .

OTHER PUBLICATIONS

Faulkner, D. J., (1984), "Marine Natural Products: Metabolites of Marine Invertebrates", Natural Product Reports, 1:551–598.
Uemura, Daisuke, Kanji Takabashi, and Toshihiro Yamamoto, (1985), "Norhalichondrin A: An Antitumor Polyether Macrolike from a Marine Sponge", J. Am. Chem. Soc., 107(16):4796–4798.
Faulkner, D. J., (1987), "Marine Natural Products", Natural Products Reports, 4(5):539–576.
Faulkner, D. J., (1986), "Marine Natural Products", Natural Products Reports, 3:1–33.

*Primary Examiner*—Frederick E. Waddell
*Assistant Examiner*—Gregory Hook
*Attorney, Agent, or Firm*—Saliwanchik & Saliwanchik

[57] ABSTRACT

Mycalamide compounds are derived from marine sponges of the genus Mycale or prepared by synthetic methods. These compounds, and pharmaceutical compositions containing them as active ingredients, are useful as immunomodulatory agents.

3 Claims, 3 Drawing Sheets

METHOD FOR TREATING TRANSPLANT PATIENTS USING MYCALAMIDE COMPOUNDS

DESCRIPTION

1. Field of the Invention

This invention relates to mycalamide compounds and compositions which have useful therapeutic properties. More particularly, the invention concerns mycalamide compounds having immunomodulatory activities, pharmaceutical compositions comprising such compounds, methods for the preparation of the compounds, and compositions and methods of their use for therapeutic purposes.

2. Background of the Invention

Immunomodulation is a developing segment of immunopharmacology. Immunomodulator compounds and compositions, as the name implies, are useful for modulating or regulating immunological functions in animals. Immunomodulators may be immunostimulants for building up immunities to, or initiate healing from, certain diseases and disorders. Conversely, immunomodulatories may be immunoinhibitors or immunosuppressors for preventing undesirable immune reactions of the body to foreign materials, or to prevent or ameliorate autoimmune reactions or diseases.

Immunomodulators have been found to be useful for treating systemic autoimmune diseases, such as lupus erythematosus and diabetes, as well as immunodeficiency diseases. Further, immunomodulators may be useful for immunotherapy of cancer or to prevent rejections of foreign organs or other tissues in transplants, e.g., kidney, heart, or bone marrow.

Various immunomodulator compounds have been discovered, including FK506, muramylic acid dipeptide derivatives, levamisole, niridazole, oxysuran, flagyl, and others from the groups of interferons, interleukins, leukotrienes, corticosteroids, and cyclosporins. Many of these compounds have been found, however, to have undesirable side effects and/or high toxicity. New immunomodulator compounds are therefore needed to provide a wider range of immuomodulator function for specific areas with a minimum of undesirable side effects.

Immunomodulation is thus of prime importance to man, and considerable research has been devoted to immunomodulatory measures. Certain methods and chemical compositions have been developed which aid in immunomodulation, but additional methods and compositions are needed.

It has been found that some natural products and organisms are potential sources for chemical molecules having useful biological activity of great diversity. Marine life has been the source for the discovery of compounds having varied biological activities. Some of the United States patents which have issued for such inventions are as follows: U.S. Pat. No. 4,548,814 for didemnins, having antiviral activity, were isolated from a marine tunicate; U.S. Pat. No. 4,729,996 discloses compounds, having antitumor properties, that were isolated from marine sponges *Teichaxinella morchella* and *Ptilocaulis walpersi*; U.S. Pat. No. 4,808,590 discloses compounds, having antiviral, antitumor, and antifungal properties, isolated from the marine sponge Theonella sp.; and U.S. Pat. No. 4,737,510 discloses compounds, having antiviral and antibacterial properties, isolated from the Caribbean sponge *Agelas coniferin*. Clearly, marine sponges have proved to be a source of biological compounds, and a number of publications have issued disclosing organic compounds derived from marine sponges, including Scheuer, P. J., Ed. (1978-1983) *Marine Natural Products, Chemical and Biological Perspectives*, Academic Press, New York; Faulkner, D. J. (1984) *Natural Products Reports* 1:551-598; Faulkner, D. J. (1986) *Natural Products Reports* 3:1-33; Faulkner, D. J. (1987) *Natural Products Reports* 4:539-576; Uemura, D., K. Takahashi, T. Yamamoto, C. Katayama, J. Tanaka, Y. Okumura, Y. Hirata (1985) *J. Am. Chem. Soc.* 107:4796-4798.

It has now been found that certain compounds derived from extracts of marine sponge of the genus Mycale, family Mycalidae, and order Poecilosclerida, possess useful biological activity. U.S. Pat. No. 4,868,204 and published PCT application WO/91/17172 describe some of these compounds as well as the observed antiviral and antitumor activity.

The present invention, utilizing sponges as a source material and supplemented by synthetic production methods, has provided the art with new biologically active compounds and new pharmaceutical compositions useful as immunomodulatory agents. The present invention has added to the arsenal of immunomodulatory compounds by the discovery of novel, useful immunomodulators, including compounds isolatable from extracts of marine sponges of the family Mycale.

Other advantages and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

BRIEF SUMMARY OF THE INVENTION

The invention provides mycalamide compounds having advantageous biological activities. Specifically, the mycalamide compounds have been found to be highly effective immune suppressors. Advantageously, the compounds have also been shown to have low cytotoxicity. Also provided are compositions containing such compounds, as well as methods for the preparation and use of the compounds and compositions.

The disclosure further provides a variety of processes for the production of compounds of the invention. One method of producing the compounds useful according to the subject invention comprises the steps of collecting marine sponges of the genus Mycale, family Mycalidae, and order Poecilosclerida, contacting such sponges with a selected organic solvent system to obtain an extract, fractionating the extract, and isolating mycalamide compounds from the fractionated extract. These compounds can serve as the starting materials for the preparation of many of the compounds described herein.

In other methods of making compounds useful according to the invention, certain mycalamide compounds are made by hydrogenation in the presence of a hydrogenation catalyst. Also, ion-exchange, hydrolysis, alkylation, acetylation, and other known synthesis type reactions may be used pursuant to known procedures to add, remove, or modify various groups in the original compounds to produce other compounds.

DETAILED DESCRIPTION OF THE INVENTION

Figure 1A:
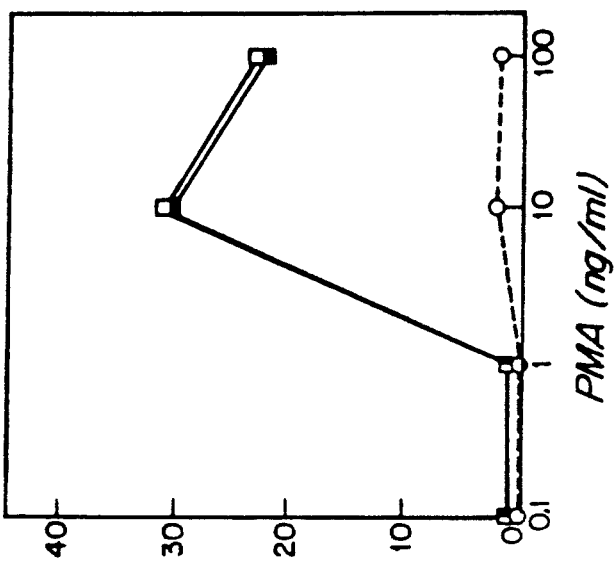
FIG. 1 shows effect of CsA on TCR- or mB7-induced T cell activation. (A) Costimulation of T cells with anti-CD3 mAb and mB7. $2\times10^5$ purified BALB/c CD4+ T lymphocytes were stimulated with the indicated concentrations of anti-CD3 mAb in the presence of medium (◯), $2\times10^4$ paraformaldehyde-fixed CHO-mB7 cells (□), or $2\times10^4$ paraformaldehyde-fixed CHO-mB7 cells in the presence of 0.1 μg/ml (0.08 μM) CsA (△) or 1 μg/ml (0.8 μM) CsA ( ). (B) Costimulation of T cells with mB7 and PMA. $2\times10^5$ purified BALB/c CD4+ T lymphocytes were stimulated with the indicated concentrations of PMA and either medium (◯), $2\times10^4$ paraformaldehyde-fixed CHO-mB7 cells (□) or paraformaldehyde-fixed CHO-mB7 cells in the presence of 1 μg/ml CsA ( ). All cultures were incubated for 48 hours and pulsed with 1 μCi [$^3$H] thymidine/well for the last 6 hours of the incubation period to assay for T cell proliferation.

The subject invention pertains to the immunosuppressive use of chemical compounds isolated from marine sponges, and various derivatives and analogs of these compounds. These compounds, generally known as mycalamides, can be used to reduce, suppress, inhibit, or prevent unwanted immune responses. Advantageously, this immunosuppression can be achieved without cytotoxicity. Therefore, these compounds are useful for treatments of humans or animals requiring immunosuppression. Examples of such situations include, but are not limited to, treatment or prevention of autoimmune diseases such as diabetes, lupus, and rheumatoid arthritis. Immunosuppression is also frequently needed in conjunction with organ transplants. Immunosuppressive agents can also be utilized when a human or animal has been, or may be, exposed to superantigens or other factors known to cause overstimulation of the immune system. The compounds of the subject invention are also useful as standards to assess the activity of other putative immunosuppressive agents. The subject invention further pertains to pharmaceutical compositions containing these compounds. Also disclosed and claimed are methods for administering the novel compositions. Various derivatives of these compounds can be produced by known procedures and as described in detail herein.

Compounds useful according to the subject invention can be isolated by various fractionation and chromatographic techniques from the extracts obtained as disclosed herein. Preferred isolation procedures include various chromatography techniques, such as countercurrent chromatography, with suitable columns including multi-layer planetary coil columns. A variety of solvents are available for use as single or mixed eluents, such as tetrahydrofuran, methanol, ethyl acetate, acetonitrile, n-propanol, n-butanol, water, and equivalent solvents. Further purifications using such procedures may also be carried out on the recovered extractions. Preferred isolation techniques for further purifications include chromatographic operations such as high-pressure liquid chromatography (HPLC) with suitable columns and suitable solvents.

A more complete understanding of the invention can be obtained by reference to preferred embodiments of the invention which are illustrated by the following specific examples of compounds, compositions, and methods of the invention. It will be apparent to those skilled in the art that the examples involve use of materials and reagents that are commercially available from known sources, e.g., chemical supply houses, so no details are given respecting them.

The subject invention pertains to the use of mycalamide A, mycalamide B, the derivatives of these compounds described herin, the derivatives of these compounds disclosed in U.S. Pat. No. 4,868,204, and other obvious variations or derivatives of these compounds. As will be seen in some of the examples below, the subject invention pertains, in part, to a class of compounds having the following structural formula:

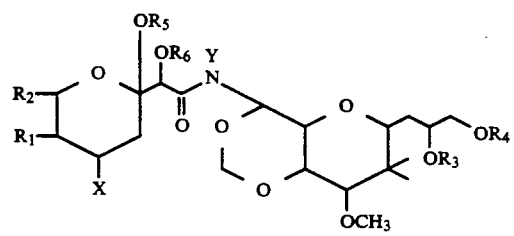

wherein $R^1$ and $R^2$ are the same or different and are hydrogen or lower alkyl, particularly C1-C5 alkyl; $R^{3-6}$ are the same or different and are hydrogen, lower alkyl, acyl, lower alkyl silyl, Bn, or Bz; X is —CH₂, —CH₃, or —O—CH₂; and Y is lower alkyl, Bn, or Bz.

Following are examples which illustrate procedures, including the best mode, for practicing the invention. These examples should not be construed as limiting. All percentages are by weight and all solvent mixture proportions are by volume unless otherwise noted.

EXAMPLE 1

The compound known as mycalamide A has the following formula:

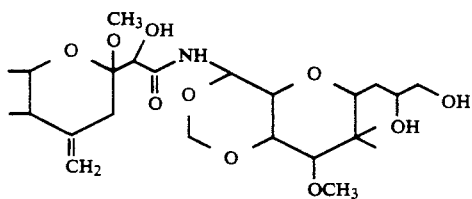

Mycalamide A is described in U.S. Pat. No. 4,868,204. A New Zealand marine sponge of the genus Mycale (family Mycalidae, order Poecilosclerida) was collected from the channel at Aquarium Point, Otago Harbour, New Zealand. Two hundred grams of frozen sponge were extracted by blending with 3:1 methanol:toluene and filtering off the solid. On removing the solvents, the combined extracts from three such steps yielded a brown gum (11.04 g) with antiviral properties. Reverse phase flash chromatography (Blunt et al. [1987] J. Natl. Prod. 50:290) gave bioactive fractions on eluting with 1:1, 3:1, and 9:1 mixtures of H₂O:methanol. These were combined to give a brown oil (307 mg). A subsample of this material (140 mg) was applied to a column of Fractogel PGM 2000 (120 g Fractogel, column 43 cm×2 cm). Eluting with 1:4 H₂O:methanol (0.5 ml/min) gave bioactive fractions at around 1.5 void volumes, which were combined (brown oil, 50 mg). Silica gel column chromatography (DAVISIL, 35–60 μm, 5 g) starting with CH₂Cl₂, then increasing amount of methanol, gave 1.7 mg of mycalamide A in the most bioactive fraction, eluted with 1:9 methanol:CH₂Cl₂.

Spectral data: [α]365 nm+110° (c 0.2 gm/100 ml, CHCl₃)

MS (EI): M⁺, measured 503.27220 daltons, calculated for C₂₄H₄₁NO₁₀ 503.27305 (−1.7 ppm). M⁺-methanol, measured 471.24824 daltons, calculated for C₂₃H₃₇NO₉ 471.24683 (+3.0 ppm).

IR, film (cm⁻¹): 3700–3100, 2690, 1740, 1700, 1540, 1470, 1390, 1100, 1080, 1040.

¹H NMR (CDCl₃): δ 7.49 (NH9, d, 9.8), 5.87 (H10, t, 9.8), 5.13 (10-OCH₂, d, 6.9), 4.84 (4=CH₂, m), 4.73 (4=CH₂, m), 4.30 (H7, s), 4.22 (H12, dd, 6.7, 10.3), 3.98 (H2, dq, 2.7, 6.6), 3.86 (H11, dd, 6.7, 9.8), 3.74 (H17, m), 3.60 (H15, dd, 4.0, 5.5), 3.55 (13-OCH₃, s), 3.55 (H18, m, hidden), 3.46 (H13, d, 10.3), 3.38 (H18, dd, 6.2, 11.2), 3.29 (6-OCH₃, s), 2.36 (H₂5, m), 2.24 (H3, dq, 2.7, 7.0), 1.54 (H₂16, m), 1.19 (2-CH₃, d, 6.6), 0.99 (3-CH₃, d, 7.0), 0.98 (14-CH₃(eq), s), 0.87 (14-CH₃(ax), s) ppm (couplings in Hz).

¹³C NMR (CDCl₃): δ 171.52 (C8), 145.40 (C4), 110.41 (4=CH₂), 99.66 (C6), 86.71 (10-OCH₂), 79.01 (C13), 78.91 (C15), 74.30 (C12), 73.62 (C10), 72.77 (C7), 71.51 (C17), 71.16 (C11), 69.70 (C2), 66.41 (C18), 61.75 (13-OCH₃), 48.88 (6-OCH₃), 41.61 (C14), 41.31 (C3), 33.70 (C5), 31.95 (C16), 23.10 (14-CH₃(eq)), 17.89 (2-CH₃), 13.51 (14-CH₃(ax)), 12.03 (3-CH₃).

EXAMPLE 2

The compound known as mycalamide B has the following formula:

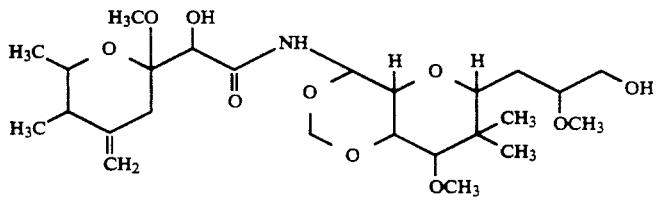

Mycalamide B is described in U.S. Pat. No. 4,864,204. Mycalamide B, an oil having a molecular formula of C₂₅H₄₃NO₁₀ and a molecular weight of 517, was extracted, using the same general procedure as described in Example 1, from the same sponge, i.e., Mycale sp. (type specimen PML1-9, Chemistry Department, University of Canterbury), family Mycalidae, order Poecilosclerida (Perry et al. [1988] JACS 110:4850–4851; J. Org. Chem. [1990] 55:223). Experience indicates that mycalamide A and B co-occur in all samples of the active Mycale sp. of sponge.

Spectral data: [α]_D+39° (c 0.2, CHCl₃).

HREIMS: M⁺—CH₃O 486.26993 (−0.8 ppm), M⁺—CH₃OH 485.26422 (+3.5 ppm).

DCIMS (NH₃): 535 (5%, M+NH₄⁺), 505 (28%), 504 (38%), 503 (100%, M+NH₄⁺—CH₃OH), 488 (23%), 487 (36%), 486 (89%).

DCIMS (ND₃): 543 (5%), 542 (14%), 541 (10%), 513 (17%), 512 (19%), 511 (34%), 510 (100%), 509 (82%), 508 (29%), 493 (8%), 492 (9%), 491 (15%), 490 (36%), 489 (37%), 488 (16%).

DCIMS (CH₄): 488 (16%), 487 (32%), 486 (100%, MH⁺CH₃OH), 456 (16%).

IR (film): 3700–3100, 2950, 1700, 1540, 1470, 1390, 1100, 1080, 1040, 750 cm⁻¹.

IR (CHCl₃): 3600–3300, 2900, 1690, 1390, 1100, 1040 cm⁻¹.

¹H NMR (CDCl₃): δ 7.54 (NH9, d, 10.0), 5.79 (H10, t, 9.7), 5.12 (10-O-CH₂, d, 7.0), 4.85 (10-O-CH₂, d, 6.9), 4.85 (4=CH₂, t, 2.0), 4.72 (4=CH₂, t, 1.9), 4.29 (H7, s), 4.21 (H12, dd, 6.7, 10.4), 4.02 (H2, dq, 2.8, 6.6), 3.79 (H11, dd, 6.7, 9.7), 3.65 (H18, dd, 3.3, 11.9), 3.55 (13-O-CH₃, s), 3.47 (H18, dd, 5.7, 11.9), 3.44 (H13, d, 10.5), 3.41 (H15, dd, 3.2, 9.1), 3.29 (6-O-CH₃, s), 3.24 (17-O-CH₃, s), 3.2 (H17, m), 2.36 (H5(eq), d, 13.9), 2.22 (H5(ax), td, 2.0, 13.9), 2.24 (H3, dq, 2.4, 6.9), 1.5 (H₂, m), 1.20 (2-CH₃, d, 6.6), 1.01 (3-CH₃, d, 7.1), 0.97 (14-CH₃(eq), s), 0.85 (14-CH₃(ax), s) ppm (couplings in Hz).

¹³C NMR (CDCl₃): δ 171.88 (C8), 145.10 (C4), 111.02 (4=CH₂), 99.95 (C6), 86.49 (10-O-CH₂), 79.27 (C13), 78.84 (C17), 75.46 (C15), 74.44 (C12), 73.90 (C10), 71.73 (C7), 70.94 (C11), 69.64 (C2), 63.48 (C18), 61.78 (13-O-CH₃), 56.64 (17-O-CH₃), 48.57 (6-O-CH₃), 41.47 (C14), 41.27 (C3), 33.64 (C5), 29.63 (C16), 23.13 (14-CH3(eq)), 17.93 (2-CH3), 13.32 (14-CH3(ax)), 1213 (3-CH3).

EXAMPLE 3

Mycalamide A Triacetate

Mycalamide A triacetate has a molecular weight of 629 and a molecular formula of $C_{30}H_{47}NO_{13}$. Its molecular structure is as follows:

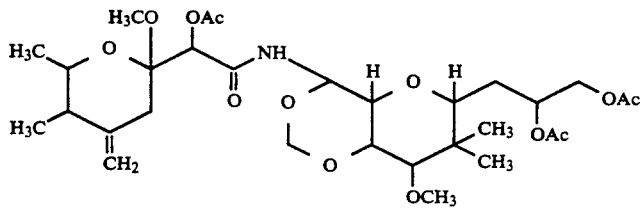

The compound is characterized as follows:
HREIMS: $M^+$—CH3OH 590.2800 (−10.6 ppm); $M^+$—CH3OH 597.27536 (−5.3 ppm).
DCIMS (NH3): 647 (13%, M+NH4), 617 (29%), 616 (37%), 615 (100%, M+NH4+—CH3OH), 542 (35%), 318 (42%), 317 (44%), 299 (30%), 286 (58%), 285 (41%), 270 (28%), 269 (60%), 257 (30%).
DCIMS (CH4): 598 (71%, MH+—CH3OH), 538 (100%, MH+—CH3OH—CH3CO2H), 299 (53%), 269 (50%), 240 (41%), 208 (55%).
1H NMR (CDCl3): δ 7.32 (NH9, d, 9.4), 5.76 (H10, t, 9.0), 5.47 (H7, s), 5.06 (10-OCH2, d, 9.4), 5.76 (H10, t, 9.0), 5.47 (H7, s), 5.06 (10-OCH2, d, 6.9), 4.98 (H17, m), 4.87 (4=CH2, m), 4.86 (10-OCH2, d, 7.0), 4.76 (4=CH2, m), 4.27 (H18, dd, 2.7, 12.4), 4.14 (H18, dd, 5.2, 12.4), 4.10 (H12, dd, 6.0, 9.4), 3.99 (H2, dq, 2.8, 6.6), 3.79 (H11, dd, 6.0, 8.7), 3.52 (13-OCH3, s), 3.36 (H13, d, 9.4), 3.45 (H15, dd, 2.4, 9.8), 3.18 (6-OCH3, s), 2.4 (H25, m), 2.25 (H3, dq, 2.7, 7.0), 2.20 (7-OCOCH3, s), 2.05 and 2.00 (17-OCOCH3, s and 18-OCHCH3, 2xs), 1.7–1.8 (H216, m), 1.20 (2-CH3, d, 6.6), 1.03 (3-CH3, d, 7.1), 1.01 (14-CH3(eq), s), 0.86 (14-CH3(ax), s) ppm (couplings in Hz).
13C NMR (CDCl3): δ 170.60 (C8), 169.85, 167.64 and 167.01 (7-OCO, 17-OCO, and 18-OCO), 145.08 (C4), 110.85 (4=CH2), 99.26 (C6), 86.53 (10-OCH2), 79.73 (C13), 75.53 (C15), 74.06 (C12), 73.72 (C10), 71.66 (C7), 70.01 (C17), 69.91 (C11), 69.73 (C2), 63.57 (C18), 61.55 (13-OCH3), 48.60 (6-OCH3), 41.24 (C14, C3), 34.18 (C5), 30.08 (C16), 23.69 (14-CH3(eq)), 21.06, 20.80 and 20.65 (7-OCOCH3, 17-OCOCH3, and 18-OCOCH3), 17.87 (2-CH3), 14.4 (14-CH3(ax)), 12.04 (3-CH3) ppm.

Mycalamide A triacetate is prepared as follows: Mycalamide A (2 mg) was dissolved in pyridine (0.5 ml) and acetic anhydride (0.5 ml). After 7 hours at 21° C., water (1 ml) was added and the mixture extracted with CHCl3 (3×1 ml). The solvent was removed and combined organic extracts were subjected to silica gel chromatography (200 mg Davisil, 150 Å, 35–70 μm), developed in steps from hexane to ethyl acetate. A fraction (1.2 mg) eluted with 1:1 hexane:ethyl acetate was pure mycalamide A triacetate, an oil.

EXAMPLE 4

Mycalamide B Diacetate

Mycalamide B diacetate has a molecular weight of 601 and a molecular formula of $C_{29}H_{47}NO_{12}$. Its molecular structure is as follows:

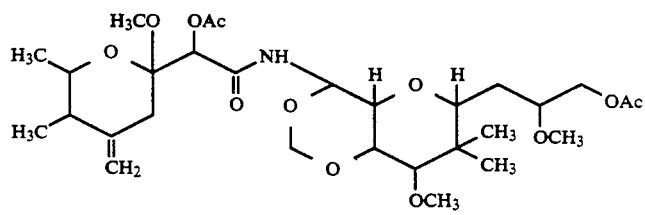

The compound is characterized as follows:
DCIMS (NH3): 619 (22%, M+NH4), 589 (16%), 588 (32%), 587 (100%, M+NH4—CH3OH), 570 (25%, MH+—CH3OH), 318 (19%), 290 (25%), 258 (62%), 257 (26%), 241 (45%).
IR (CHCl3): 3400, 2950, 2900, 1750, 1710, 1380, 1100, 1030, 910 cm−1.
1H NMR (CDCl3): δ 7.27 (NH9, d, 9.4), 5.75 (H10, t, 9.4), 5.45 (H7, s), 5.07 (10-OCH2, d, 7.0), 4.88 (4=CH2, m), 4.85 (10-OCH2, d, 6.9), 4.75 (4=CH2, m), 4.28 (H18, dd, 2.5, 12.3), 4.17 (H12, dd, 6.6, 10.2), 4.07 (H18, dd, 4.7, 12.5), 4.02 (H2, dq, 2.8, 6.7), 3.77 (H11, dd, 6.5, 9.4), 3.53 (13-OCH3, s), 3.39 (H13, d, 9.8), 3.3 (H17, m), 3.3 (H15, hidden), 3.25 (17-OCH3, s), 3.17 (6-OCH3, s), 2.4 (H25, m), 2.28 (H3, dq, 2.7, 7.3), 2.20 (7-OCOCH3, s), 2.08 (18-OCOCH3, s), 1.6–1.7 (H216, m), 1.22 (20CH3, d, 6.5), 1.04 (3-CH3, d, 7.2), 0.97 (14-CH3(eq), s), 0.86 (14-CH3(ax), s) ppm (couplings in Hz).
13C NMR (CDCl3): δ 170.85 (C8), 169.68 and 166.67 (7- and 18-OCO), 144.75 (C4), 111.26 (4=CH2), 99.15 (C6), 86.53 (10-OCH2), 79.43 (C13), 77.93 (C17), 75.68 (C15), 74.18 (C12), 74.02 (C10), 71.48 (C7), 70.64 (C11), 69.95 (C2), 63.47 (C18), 61.70 (13-OCH3), 56.88 (17-OCH3), 48.49 (6-OCH3), 41.24 (C14), 41.16 (C3), 34.39 (C5), 30.33 (C16), 23.38 (14-CH3(eq)), 20.97 and 20.65 (7-OCOCH3 and 18-OCOCH3), 17.92 (2-CH3), 13.8 (14-CH3(ax), broad), 12.19 (3-CH3) ppm.

Mycalamide B diacetate is prepared as follows: Mycalamide B (3.5 mg) was dissolved in pyridine (0.1 ml) and acetic anhydride (0.1 ml). After four hours at 21° C., water (0.2 ml) was added and the mixture extracted with CHCl3 (3×2.0 ml). The solvent was removed and the combined organic extracts were subjected to silica gel chromatography (200 mg Davisil, 150 Å, 35–70 μm), developed in steps from hexane to ethyl acetate. A fraction (3 mg) eluted with 1:1 hexane:ethyl acetate was pure mycalamide B diacetate, an oil.

EXAMPLE 5

Mycalamide B 18-Mono-TBDMS Ether

Mycalamide B 18-Mono-TBDMS Ether has a molecular weight of 631 and a molecular formula of $C_{31}H_{57}NO_{10}Si$. Its molecular structure is as follows:

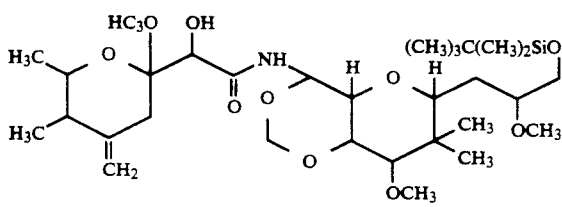

The compound is characterized as follows:

$^1$H NMR ($CD_2Cl_2$): δ 7.51 (NH9, d, 9.4), 5.78 (H10, t, 9.4), 5.12 (10-OCH$_2$, d, 7.0), 4.86 (4=CH$_2$, t, 2.0), 4.84 (10-OCH$_2$, d, 7.0), 4.70 (4=CH$_2$, t, 2.0), 4.24 (H7, d, 2.7), 4.14 (H12, dd, 6.3, 9.5), 4.03 (H2, dq, 2.9, 6.6), 3.86 (7-OH, d, 2.7), 3.79 (H11, dd, 6.3, 9.0), 3.67 (H18, dd, 2.8, 11.5), 3.57 (H18, dd, 4.1, 11.5), 3.53 (13-OCH$_3$, s), 3.41 (H13, d, 9.3), 3.36 (H15, dd, 1.5, 9.8), 3.28 (6-OCH$_3$, s), 3.21 (17-OCH$_3$, s), 3.12 (H17, m), 2.30 (H5(eq), d, 13.8), 2.27 (H3, dq, 2.6, 7.0), 2.15 (H5(ax), td, 2.1, 14.2), 1.76 (H16, ddd, 2.0, 9.5, 14.2), 1.5 (H16, m), 1.21 (2-CH$_3$, d, 6.6), 1.02 (3-CH$_3$, d, 7.2), 1.02 (14-CH$_3$(eq), s), 0.91 (18-OSiC(CH$_3$)$_3$, s), 0.87 (14-CH$_3$(ax), s), 0.08 and 0.09 (18-OSi(CH$_3$)$_2$, 2xs) ppm (couplings in Hz).

$^{13}$C NMR ($CD_2Cl_2$): δ 145.88 (C4), 110.74 (4=CH$_2$), 100.14 (C6), 86.53 (10-OCH$_2$), 79.96 (C13), 79.09 (C17), 76.49 (C15), 74.23 (C12, C10), 71.59 (C7), 69.70 (C2), 62.48 (C18), 61.53 (13-OCH$_3$), 56.74 (17-OCH$_3$), 48.46 (6-OCH$_3$), 41.57 (C3), 33.70 (C5), 29.91 (C16), 25.89 (18-OSiC(CH$_3$)$_3$), 23.70 (14-CH$_3$(eq)), 17.90 (2-CH$_3$), 12.34 (3-CH$_3$), −5.43 (18-OSi(CH$_3$)$_2$). NB: C8, C11, C14, 14-CH$_3$(ax) not observed.

Mycalamide B 18-Mono-TBDMS Ether is prepared as follows: Mycalamide b (3 mg), t-butyldimethylchlorosilane (12 mg), dimethylaminopyridine (1 mg) and triethylamine (14 mg) were stirred in pyridine (0.2 ml) at room temperature for 20 hours. H$_2$O (0.5 ml) was added, the mixture extracted with CH$_2$Cl$_2$ (3×0.3 ml), and the solvent removed. The combined organic extract was subjected to silica gel chromatography (200 mg Davisil, 150 Å, 35–70 μm), developed in steps from hexane to ethanol/ethyl acetate. The major fraction (1.7 mg) which eluted with 1:19 EtOH:EtOAc was unreacted mycalamide B, but a fraction (1.5 mg) which eluted with 1:1 PE:EtOAc was pure mycalamide B 18-mono-TBDMS ether by PMR, an oil.

EXAMPLE 6

Mycalamide B 7-Monoacetate

Mycalamide B 7-monoacetate has a molecular weight of 559 and molecular formula of $C_{27}H_{45}NO_{11}$. Its molecular structure is as follows:

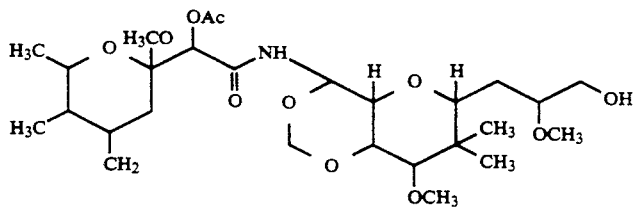

The compound is characterized as follows:

DCIMS (NH$_3$) 577 (15%, M+NH$_4$+), 547 (28%), 546 (30%), 545 (100%, M+NH$_4$+—CH$_3$OH), 530 (10%), 529 (11%), 528 (34%, MH+—CH$_3$OH).

$^1$H NMR ($CD_2Cl_2$): δ 7.44 (NH9, d, 9.8), 5.77 (H10, t, 9.5), 5.47 (H7, s), 5.12 (10-OCH$_2$, d, 7.0), 4.89 (4=CH$_2$, m), 4.85 (10-OCH$_2$, d, 7.1), 4.74 (4=CH$_2$, m), 4.20 (H12, dd, 6.7, 10.7), 4.02 (H2, dq, 2.9, 6.5), 3.78 (H11, dd, 6.7, 9.6), 3.66 (H18, dd, 2.6, 12.2), 3.54 (13-OCH$_3$, s), 3.45 (H13, d, 10.3), 3.44 (H15, dd, 1.7, 10.0), 3.35 (H18, dd, 6.2, 12.2), 3.23 (17-OCH$_3$, s), 3.16 (6-OCH$_3$, s), 3.13 (H17, m), 2.39 (H25, m), 2.30 (H3, dq, 2.9, 7.1), 2.20 (7-OCOCH$_3$, s), 1.58 (H16, m), 1.41 (H16, ddd, 1.6, 10.2, 14.3), 1.24 (2-CH$_3$, d, 6.6), 1.05 (3-CH$_3$, d, 7.1), 0.98 (14-CH$_3$(eq), s), 0.85 (14-CH$_3$(ax), s) ppm (couplings in Hz).

$^1$H NMR (CDCl$_3$): δ 7.46 (NH9, d, 10.0), 5.77 (H10, t, 9.3), 5.52 (H7, s), 5.09 (10-OCH$_2$, d, 7.1), 4.88 (4=CH$_2$, m), 4.87 (10-OCH$_2$, d, 7.1), 4.77 (4=CH$_2$, m), 4.22 (H12, dd, 7.1, 10.2), 4.04 (H2, dq, 2.8, 6.6), 3.75 (H11, dd, 6.6, 9.6), 3.71 (H18, dd, 2.1, 12.3), 3.55 (13-OCH$_3$, s), 3.44 (H15, broad d, 10.0), 3.42 (H13, d, 10.4), 3.41 (H18, dd, 6.7, 12.3), 3.26 (17-OCH$_3$, s), 3.14 (6-OCH$_3$, s), 3.14 (H17, m), 2.43 (H25, m), 2.29 (H3, dq, 2.9, 7.1), 2.21 (7-OCOCH$_3$, s), 1.54 (H16, m), 1.38 (H16, m), 1.24 (2-CH$_3$, d, 6.7), 1.05 (3-CH$_3$, d, 7.1), 0.96 (14-CH$_3$(eq), s), 0.85 (14-CH$_3$(ax), s) ppm (couplings in Hz).

$^{13}$C NMR ($CD_2Cl_2$): δ 145.17 (C4), 111.11 (4=CH$_2$), 99.46 (C6), 86.78 (10-OCH$_2$), 79.91 (C17), 79.40 (C13), 75.86 (C15), 74.75 (C12), 74.29 (C10), 71.45 (C7), 70.30 (C2), 63.81 (C18), 61.75 (13-OCH$_3$), 56.67 (17-OCH$_3$), 48.50 (6-OCH$_3$), 41.50 (C14), 41.37 (C3), 34.73 (C5), 30.18 (C16), 23.13 (14-CH$_3$(eq)), 20.54 (7-OCOCH$_3$), 17.84 (2-CH$_3$) 13.32 (14-CH$_3$(ax), broad), 12.20 (3-CH$_3$). NB: C8, 7-OCO and C11 not observed.

Mycalamide B 7-monoacetate can be prepared as follows: Mycalamide B 18-mono-TMS ether (1 mg ca) was dissolved in pyridine (0.1 ml) and acetic anhydride (0.1 ml). The preparation of mycalamide B 18-mono-TMS ether is described in U.S. Pat. No. 4,868,204. After 3 hrs at room temperature, H$_2$O (0.2 ml) was added, the mixture extracted with CH$_2$Cl$_2$ (3×0.2 ml), and the solvent removed (1 mg). TLC and PMR showed desilylation and about 25% diacetate present in an otherwise clean sample of mycalamide B 7-monoacetate. Subsequently this was purified by subjecting the combined sample to silica gel chromatography (200 mg Davisil, 150 Å, 35–70 μm), developed in steps from hexane to ethyl acetate. The major fraction (0.7 mg) which eluted with 100% ethyl acetate was pure mycalamide B 7-monoacetate, an oil.

EXAMPLE 7

7-Methoxy, Mycalamide B 18-Monoacetate

7-Methoxy, Mycalamide B 18-Monoacetate has a molecular weight of 573 and a molecular formula of $C_{28}H_{47}NO_{11}$. Its molecular structure is as follows:

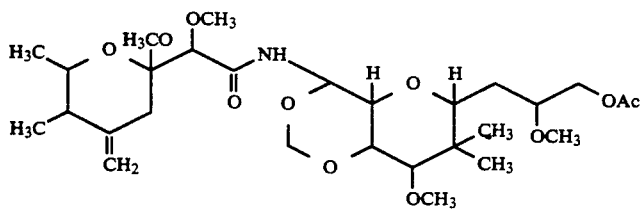

The compound is characterized as follows:

DCIMS (NH$_3$): 591 (2%, M+NH$_4$+), 562 (9%), 561 (34%), 561 (34%), 560 (32%), 559 (100%, M+NH$_4$+—CH$_3$OH), 545 (11%), 544 (36%), 543 (30%), 542 (99%, MH+—CH$_3$OH).

$^1$H NMR (CDCl$_3$): δ 7.11 (NH9, d, 9.9), 5.79 (H10, t, 9.7), 5.11 (10-OCH$_2$, d, 6.9), 4.83 (10-OCH$_2$, d, 6.7), 4.82 (4=CH$_2$, t, 1.7), 4.71 (4=CH$_2$, t, 1.8), 4.27 (H18, dd, 2.5, 12.1), 4.20 (H12, dd, 6.7, 10.2), 4.03 (H18, dd, 5.3, 12.1), 3.94 (H2, dq, 2.8, 6.6), 3.85 (H7, s), 3.81 (H11, dd, 6.8, 9.6), 3.54 (13-OCH$_3$, s), 3.54 (7-OCH$_3$, s), 3.43 (H13, d, 10.2), 3.37 (H17, m), 3.36 (H15, dd, 4.5, 7.6), 3.28 (17-OCH$_3$, s), 3.27 (6-OCH$_3$, s), 2.41 (H5(ax), td, 2.0, 14.1), 2.30 (H5(eq), d, 14.3), 2.21 (H3, dq, 2.9, 7.1), 2.08 (18-OCOCH$_3$, s), 1.63 (H$_2$16, m), 1.17 (2-CH$_3$, d, 6.6), 0.98 (3-CH$_3$, d, 7.1), 0.97 (14-CH$_3$(eq), s), 0.87 (14-CH$_3$(ax), s) ppm (couplings in Hz).

$^{13}$C NMR (CDCl$_3$): δ 170.87 (C8), 169.69 (18-OCO), 145.95 (C4), 110.25 (4=CH$_2$), 99.91 (C6), 86.45 (10-OCH$_2$), 82.72 (C7), 79.42 (C13), 75.53 (C15), 74.31 (C12), 73.31 (C10), 70.75 (C11, broad), 69.45 (C2), 64.12 (C18), 61.77 (13-OCH$_3$), 60.06 (7-OCH$_3$), 56.91 (17-OCH$_3$), 48.94 (6-OCH$_3$), 41.43 (C14), 41.38 (C3), 34.15 (C5), 30.20 (C16), 23.31 (14-CH$_3$(eq)), 20.95 (18-OCOCH$_3$), 17.87 (2-CH$_3$), 13.55 (14-CH$_3$(ax), broad), 11.87 (3-CH$_3$). NB: C17 not observed.

7-methoxy, mycalamide B 18-monoacetate can be prepared as follows: Mycalamide B (6 mg), Ag$_2$O (40 mg), and MeI (27 mg) were stirred in benzene (0.4 ml) for 2 hours at 90° C. The solution was filtered over celite and the solvent removed. Pyridine (0.1 ml) and acetic anhydride (0.1 ml) were added and the mixture stirred at room temperature for 16 hours. H$_2$O was added (2.5 ml) and the solution extracted with CH$_2$Cl$_2$ (2×2 ml). Prep TLC of this extract (3:1 EtOAc:PE) gave three fractions (1.7 mg, 2.0 mg, 2.4 mg) which were pure 7-methoxy mycalamide B 18-acetate, 18-methoxy mycalamide B 7-acetate, and mycalamide B diacetate respectively by nmr, an oil.

EXAMPLE 8

7-Methoxy Mycalamide B 7-methoxy mycalamide B has a molecular weight of 531 and a molecular formula of $C_{26}H_{45}NO_{10}$. Its molecular structure is as follows:

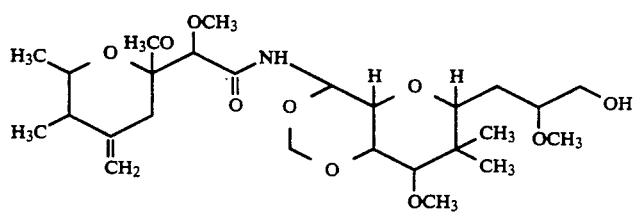

The compound is characterized as follows:

DCIMS (NH$_3$): 549 (6%, M+NH$_4$+), 520 (4%), 519 (20%), 518 (40%), 517 (100%, M+NH$_4$+—CH$_3$OH), 502 (13%), 501 (29%), 500 (79%, MH+—CH$_3$OH).

$^1$H NMR (CDCl$_3$): δ 7.25 (NH9, d, 9.7), 5.82 (H10, t, 9.7), 5.13 (10-OCH$_2$, d, 6.9), 4.85 (10-OCH$_2$, d, 7.0), 4.83 (4=CH$_2$, t, 1.9), 4.71 (4=CH$_2$t, 2.0), 4.23 (H12, dd, 6.8, 10.5), 3.94 (H2, dq, 2.7, 6.6), 3.89 (H7, s), 3.80 (H11, dd, 6.8, 10.0), 3.69 (H18, dd, 3.0, 12.0), 3.57 (7-OCH$_3$, s), 3.56 (13-OCH$_3$, s), 3.45 (H13, d, 10.5), 3.45 (H18, m), 3.43 (H15, dd, 1.7, 10.0), 3.30 (17-OCH$_3$, s), 3.27 (6-OCH$_3$, s), 3.22 (H17, m), 2.41 (H5(ax), td, 1.9, 14.3), 2.32 (H5(eq), d, 14.4), 2.21 (H3, dq, 2.5, 7.0), 1.57 (H16, m), 1.46 (H16, m), 1.17 (2-CH$_3$, d, 6.6), 0.98 (3-CH$_3$, d, 7.0), 0.97 (14-CH$_3$(eq), s), 0.86 (14CH$_3$(ax), s) ppm (couplings in Hz).

$^{13}$C NMR (CDCl$_3$): δ 170.33 (C8), 145.77 (C4), 110.37 (4=CH$_2$), 100.00 (C6), 86.61 (10-OCH$_2$), 82.39 (C7), 79.72 (C17), 79.27 (C13), 75.49 (C15), 74.64 (C12), 73.51 (C10), 71.41 (C11), 69.52 (C2), 64.69 (C18), 61.86 (13-OCH$_3$), 60.39 (7-OCH$_3$), 56.87 (17-OCH$_3$), 48.98 (6-OCH$_3$), 41.59 (C14), 41.36 (C3), 34.19 (C5), 29.94 (C16), 23.12 (14-CH$_3$(eq)), 17.85 (2-CH$_3$), 13.18 (14-CH$_3$(ax), broad), 11.88 (3-CH$_3$).

7-methoxy mycalamide B can be prepared as follows: 7-Methoxy mycalamide B 18-monoacetate (1.8 mg) was stirred in a solution with 1.2 mg K$_2$CO$_3$ in aqueous MeOH (0.4 ml) at room temperature for 5 hours. The solution was concentrated, then H$_2$O (2.5 ml) was added and the solution extracted with CH$_2$Cl$_2$ (3×2 ml). The solvent was removed and the sample subjected to prep TLC (developed twice in 1:5 PE:EtOAc) to give pure 7-methoxy mycalamide B (1.2 mg) by NMR, an oil.

EXAMPLE 9

Mycalamide B 7-Monobenzyl Ether

Mycalamide B 7-Monobenzyl Ether has a molecular weight of 607 and a molecular formula of $C_{32}H_{49}NO_{10}$. Its molecular structure is as follows:

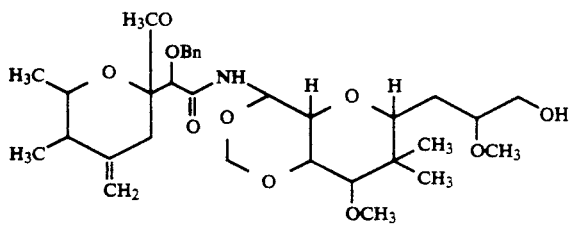

The compound is characterized as follows:
HRFABMS: 630.3202 (M+Na+, −8.3 ppm).
FABMS: 631 (9%), 630 (100%, M+Na+), 598 (7%, M+Na+—CH3OH), 577 (8%), 576 (20%, MH+—CH3OH).

$^1$H NMR (CDCl3): δ 7.4-7.3 (φ, m), 7.35 (NH9, d, 9.8), 5.85 (H10, t, 9.8), 5.13 (10-OCH2, d, 6.9), 4.84 (10-OCH2, d, 7.1), 4.82 (4=CH2, m), 4.81 (7-OCH2φ, d, 11.5), 4.72 (4=CH2, m), 4.64 (7-OCH2φ, d, 11.3), 4.23 (H12, dd, 6.9, 10.6), 4.11 (H7, s), 3.91 (H2, dq, 2.8, 6.6), 3.77 (H11, dd, 6.7, 9.9), 3.71 (H18, dd, 2.9, 12.1), 3.56 (13-OCH3, s), 3.48 (H18, dd, 6.6, 11.9), 3.46 (H13, d, 10.4), 3.45 (H15, broad d, 10.0), 3.27 (17-OCH3, s), 3.27 (H17, m), 3.10 (6-OCH3, s), 2.43 (H25, m), 2.20 (H3, dq, 2.7, 7.0), 1.55 (H16, m), 1.45 (H16, ddd, 1.6, 9.8, 14.3), 1.17 (2-CH3, d, 6.6), 0.98 (14-CH3(eq), s), 0.98 (3-CH3, d, 7.0), 0.88 (14-CH3(ax), s) ppm (couplings in Hz).

$^{13}$C NMR (CDCl3): δ 170.52 (C8), 146.00 (C4), 136.98, 128.57, 128.24 and 128.20 (7-OCH2φ), 110.30 (4=CH2), 100.10 (C6), 86.58 (10-OCH2), 80.15 (C7), 79.71 (C17), 79.29 (C13), 75.45 (C15), 74.64 (C12), 74.22 (C10), 73.48 (7-OCH2), 71.38 (C11, broad), 69.50 (C2), 64.69 (C18), 61.85 (13-OCH3), 56.86 (17-OCH3), 48.95 (6-OCH3), 41.59 (C14), 41.35 (C3), 34.53 (C5), 29.85 (C16), 23.14 (14-CH3(eq)), 17.84 (2-CH3), 13.22 (14-CH3(ax), broad), 11.86 (3-CH3).

Mycalamide B 7-monobenzyl ether can be prepared as follows: Mycalamide B (4.4 mg), powdered KOH (7 mg) and benzyl bromide (12 mg) were stirred in DMSO (0.3 ml) at room temperature for 4 minutes. H2O (2 ml) was added and the mixture extracted with CHCl3 (3×2 ml). The extract was evaporated to dryness, then subjected to prep TLC(developed in 1:1 PE:EtOAc). Three bands of silica were recovered and eluted with ethyl acetate to give three pure products (1.8 mg, 0.8 mg, 0.9 mg), which were mycalamide B 7-mono-; 7,N-di- and 7,18-di-benzyl ethers by NMR respectively, an oil.

EXAMPLE 10

7,17,18-Trimethoxy, N-Methyl Mycalamide A 7,17,18-Trimethoxy, N-Methyl Mycalamide A has a molecular weight of 559 and a molecular formula of $C_{28}H_{49}NO_{10}$. Its molecular structure is as follows:

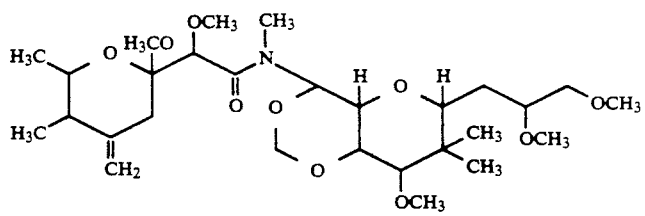

The compound is characterized as follows:
DCIMS (NH3): 577 (1%, M+NH4+), 547 (4%), 546 (6%), 545 (19%, M+NH4+—CH3OH), 531 (5%), 530 (19%), 529 (30%), 528 (100%, MH+—CH3OH).

$^1$H NMR (CDCl3): δ 6.26 (H10, d, 10.1), 5.15 (10-OCH2, d, 7.0), 4.85 (10-OCH2, d, 7.0), 4.81 (4=CH2, t, 2.0), 4.70 (4=CH2, t, 2.0), 4.26 (H12, dd, 6.8, 10.5), 4.25 (H7, s), 4.18 (H11, dd, 6.8, 10.1), 3.91 (H2, dq, 2.8, 6.6), 3.55 (13-OCH3, s), 3.53 (H18, m), 3.49 (H13, d, 10.5), 3.44 (7-OCH3, s), 3.38 (H15, broad d, 8.7), 3.37 (18-OCH3, s), 3.36 (H18, m), 3.33 (H17, m), 3.29 (6-OCH3, s), 3.27 (17-OCH3, s), 3.20 (N-CH3, s), 2.65 (H5(ax), td, 2.0, 14.2), 2.26 (H5(eq), d, 14.2), 2.18 (H3, dq, 2.8, 7.0), 1.70 (H16, ddd, 1.8, 9.6, 14.1), 1.51 (H16, ddd, 2.2, 8.9, 14.2), 1.12 (2-CH3, d, 6.6), 0.97 (14-CH3(eq), s), 0.97 (3-CH3, d, 7.0), 0.87 (14-CH3(ax),s) ppm (couplings in Hz).

$^{13}$C NMR (CDCl3): δ 170.75 (C8), 146.76 (C4), 109.75 (4=CH2), 100.74 (C6), 86.37 (10-OCH2), 84.10 (C7), 79.35 (C13), 77.33 (C10, C17), 75.82 (C15), 74.31 (C12), 72.49 (C18), 69.40 (C2), 66.78 (C11), 61.76 (13-OCH3), 59.07 (18-OCH3), 58.83 (7-OCH3), 56.36 (17-OCH3), 48.93 (6-OCH3), 41.64 (C14), 41.35 (C3), 34.06 (C5), 30.43 (C16), 28.79 (N-CH3), 23.15 (14-CH3(eq)), 17.68 (2-CH3), 13.21 (14-CH3(ax)), 11.97 (3-CH3).

7,17,18-Trimethoxy, N-methyl mycalamide A can be prepared as follows: Mycalamide A (5.5 mg), powdered KOH (14 mg) and MeI (23 mg) were stirred in DMSO (0.3 ml) at room temperature for 3.5 hours. H2O was added (0.5 ml) and the mixture transferred onto a reverse phase pipette column (200 mg C18, equilibrated to H2O), flushed with H2O (6 ml) and then eluted with MeOH (6 ml). The MeOH fraction was evaporated to dryness (5.5 mg), then subjected to prep TLC(developed in EtOAc). Two fractions of silica were recovered and each eluted with 1:9 EtOH:EtOAc (4 ml) to give two fractions on evaporation (1 mg, 3.5 mg) which were 7,18-dimethoxy, N-methyl mycalamide A and 7,17,18-trimethoxy, N-methyl mycalamide A by nmr respectively, an oil.

EXAMPLE 11

7,18-Dimethoxy, N-Methyl Mycalamide A 7,18-Dimethoxy, N-Methyl Mycalamide A has a molecular weight of 545 and a molecular formula of $C_{27}H_{47}NO_{10}$. Its molecular structure is as follows:

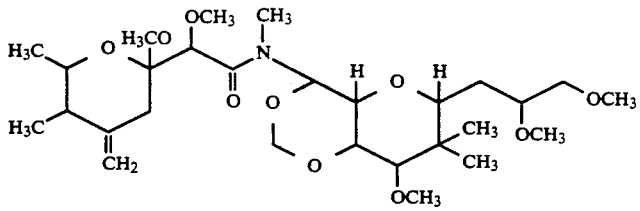

The compound is characterized as follows:

DCIMS (NH₃): 563 (10%, M+NH₄⁺), 533 (19%), 532 (37%), 531 (100%, M+NH₄⁺—CH₃OH), 516 (17%), 515 (32%), 514 (95%, MH⁺—CH₃OH).

$^1$H NMR (CDCl₃): δ 6.35 (H10, d, 9.5), 5.16 (10-OCH₂, d, 6.7), 4.88 (10-OCH₂, d, 6.6), 4.82 (4=CH₂, m), 4.72 (4=CH₂, t, 2.0), 4.29 (H12, dd, 7.2, 10.0), 4.25 (H7, s), 4.19 (H11, dd, 7.1, 9.5), 3.92 (H2, dq, 2.8, 6.5), 3.81 (H17, m), 3.69 (H15, dd, 2.5, 10.0), 3.57 (13-OCH₃, s), 3.54 (H13, d, 10.1), 3.46 (7-OCH₃, s), 3.35 (18-OCH₃, s), 3.31 (6-OCH₃, s), 3.28 (H₂18, m), 3.19 (N-CH₃, s), 2.70 (H5(ax), broad d, 14.4), 2.29 (H5(eq), d, 14.5), 2.19 (H3, dq, 3.0, 6.9), 1.71 (H16, broad d, 14.4), 1.47 (H16, m), 1.13 (2-CH₃, d, 6.4), 1.00 (3-CH₃, d, 6.8), 0.99 (14-CH₃(eq), s), 0.90 (14-CH₃(ax), s) ppm (couplings in Hz).

$^{13}$C NMR: δ 171.24 (C8), 147.01 (C4), 109.52 (4=CH₂), 100.87 (C6), 86.68 (10-OCH₂), 83.39 (C7), 79.15 (C13), 78.64 (C15), 76.44 (C18), 74.40 (C12), 69.58 (C17), 69.36 (C2), 67.01 (C11), 61.83 (13-OCH₃), 59.12 (18-OCH₃), 58.90 (7-OCH₃), 48.90 (6-OCH₃), 41.90 (C14), 41.43 (C3), 33.83 (C5), 33.34 (C16), 28.70 (N-CH₃), 22.95 (14-CH₃(eq)), 17.65 (2-CH₃), 13.20 (14-CH₃(ax)), 12.12 (3-CH₃). NB: C10 not observed.

7,18-dimethoxy N-methyl mycalamide A can be prepared as follows: Mycalamide A (5.5 mg), powdered KOH (14 mg) and MeI (23 mg) were stirred in DMSO (0.3 ml) at room temperature for 3.5 hours. H₂O was added (0.5 ml) and the mixture transferred onto a reverse phase pipette column (200 mg C18, equilibrated to H₂O), flushed with H₂O (6 ml) and then eluted with MeOH (6 ml). The MeOH fraction was evaporated to dryness (5.5 mg), then subjected to prep TLC (developed in EtOAc). Two fractions of silica were recovered and each eluted with 1:9 EtOH:EtOAc (4 ml) to give two fractions on evaporation (1 mg, 3.5 mg) which were 7,18-dimethoxy, N-methyl mycalamide A and 7,17,18-trimethoxy, N-methyl mycalamide A by nmr respectively, an oil.

EXAMPLE 12

7-Methoxy, N-Methyl Mycalamide A

7-Methoxy, N-Methyl Mycalamide A has a molecular weight of 531 and a molecular formula of C₂₆H₄₅NO₁₀. Its molecular structure is as follows:

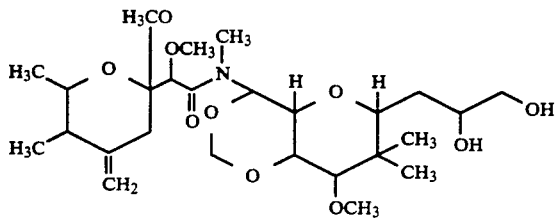

The compound is characterized as follows:

DCIMS (NH₃): 549 (3%, M+NH₄⁺), 519 (6%), 518 (20%), 517 (66%, M+NH₄⁺—CH₃OH), 502 (10%), 501 (29%), 500 (100%, MH⁺—CH₃OH).

$^1$H NMR (CDCl₃): δ 6.34 (H10, d, 9.9), 5.17 (10-OCH₂, d, 6.6), 4.89 (10-OCH₂, d, 6.7), 4.83 (4=CH₂, m), 4.73 (4=CH₂, m), 4.28 (H12, dd, 7.1, 10.6), 4.27 (H7, s), 4.15 (H11, dd, 7.2, 10.0), 3.93 (H2, dq, 2.6, 6.3), 3.74 (H17, m), 3.70 (H15, dd, 3.2, 9.8), 3.60 (H18, m), 3.58 (13-OCH₃, s), 3.53 (H13, d, 10.7), 3.45 (7-OCH₃, s), 3.34 (H18, m), 3.31 (6-OCH₃, s), 3.19 (N-CH₃, s), 2.68 (H5(ax), broad d, 14.5), 2.29 (H5(eq), d, 14.3), 2.20 (H3, dq, 2.4, 6.8), 1.58 (H₂16, broad td, 3.0, 10.1), 1.14 (2-CH₃, d, 6.5), 1.01 (3-CH₃, d, 7.0), 0.99 (14-CH₃(eq), s), 0.88 (14-CH₃(ax), s) ppm (couplings in Hz).

$^{13}$C NMR (CDCl₃): δ 146.76 (C4), 109.76 (4=CH₂), 100.82 (C6), 86.49 (10-OCH₂), 82.56 (C7), 79.16 (C13), 78.14 (C15), 77.26 (C10), 74.40 (C12), 71.07 (C17), 69.39 (C2), 67.09 (C11), 66.86 (C18), 61.86 (13-OCH₃), 58.89 (7-OCH₃), 48.90 (6-OCH₃), 41.84 (C14), 41.39 (C3), 33.88 (C5), 32.97 (C16), 28.75 (N-CH₃), 22.98 (14-CH₃(eq)), 17.66 (2-CH₃), 13.11 (14-CH₃(ax)), 12.16 (3-CH₃). NB: C8 not observed.

7-methoxy, N-methyl mycalamide A can be prepared as follows: Mycalamide A (3 mg), powdered KOH (3 mg) and MeI (7 mg) were stirred in DMSO at room temperature for 4 hours. H₂O was added (0.3 ml), the mixture extracted with CH₂Cl₂ (3×0.4 ml), and the solvent removed (3.5 mg). Prep RPLC (30% H₂O in MeOH) gave two fractions (1.9 mg, 1 mg) which were pure 7-methoxy, N-methyl mycalamide A and a 4:1 mixture of 7,18-dimethoxy, N-methyl mycalamide A and 7,17-dimethoxy, N-methyl mycalamide A by PMR respectively, an oil.

EXAMPLE 13

6-Ethoxy Mycalamide A

6-Ethoxy Mycalamide A has a molecular weight of 517 and a molecular formula of C₂₅H₄₃NO₁₀. Its molecular structure is as follows:

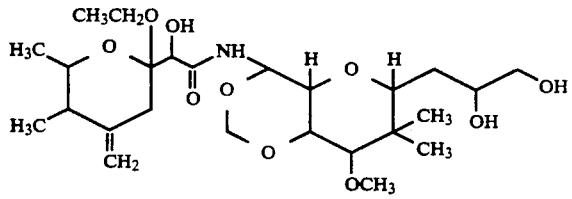

The compound is characterized as follows:

DCIMS (NH₃): 535 (6%, M+NH₄⁺), 491 (4%), 490 (6%), 489 (100%, M+NH₄⁺—CH₃CH₂OH), 474 (5%), 473 (5%), 472 (65%, MH⁺—CH₃CH₂OH).

$^1$H NMR (CDCl₃): δ 7.50 (NH9, d, 10.0), 5.87 (H10, t, 9.8), 5.14 (10-OCH₂, d, 6.9), 4.87 (10-OCH₂, d, 6.9), 4.83 (4=H₂, m), 4.73 (4=CH₂, m), 4.26 (H7, s), 4.22 (H12, dd, 6.6, 10.2), 3.99 (H2, dq, 2.8, 6.5), 3.85 (H11, dd, 6.8, 9.7), 3.74 (H17, m), 3.63 (H15, m), 3.6 (H18, m), 3.56 (13-OCH$_3$, s), 3.55 (6-OCH$_2$, q, 7.0), 3.46 (H13, d, 10.2), 3.38 (H18, dd, 6.1, 11.2), 2.38 (H25, m), 2.23 (H3, dq, 3.0, 7.1), 1.57 (H$_2$16, m), 1.18 (6-OCH$_2$CH$_3$, t, 7.0), 1.17 (2-CH$_3$, d, 6.6), 1.00 (3-CH$_3$, d, 7.1), 0.98 (14-CH$_3$(eq), s), 0.88 (14-CH$_3$(ax), s) ppm (couplings in Hz).

$^{13}$C NMR (CDCl$_3$): δ 110.49 (4=CH$_2$), 99.74 (C6), 86.83 (10-OCH$_2$), 79.16 (C13), 78.96 (C15), 74.42 (C12), 73.77 and 73.70 (C10 and C7), 71.49 (C17), 71.28 (C11), 69.84 (C2), 66.53 (C18), 61.82 (13-OCH$_3$), 56.74 (6-OCH$_2$), 41.41 (C3), 33.90 (C5), 32.05 (C16), 23.23 (14-CH$_3$(eq)), 17.92 (2-CH$_3$), 15.18 (6-OCH$_2$CH$_3$), 13.53 (14-CH$_3$(ax)), 12.08 (3-CH$_3$). NB: C8, C4, C14 not observed.

6-ethoxy mycalamide A can be prepared as follows: Mycalamide A (20 mg) was dissolved in CDCl$_3$ containing a trace of ethanol and left for two weeks. PMR showed partial reaction to at least two components and this was confirmed by HPLC. Prep HPLC (35% H$_2$O in MeOH) separated unreacted mycalamide A (4.5 mg) and 6-ethoxy mycalamide A (1.2 mg) in pure form by PMR.

EXAMPLE 14

Mycalamide A 17,18-Di-p-Bromobenzoate

Mycalamide A 17,18-Di-p-Bromobenzoate has a molecular weight of 869 and a molecular formula of C$_{38}$H$_{47}$Br$_2$NO$_{12}$. Its molecular structure is as follows:

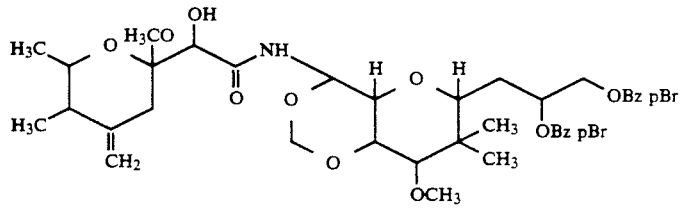

The compound is characterized as follows:

$^1$H NMR (CDCl$_3$): δ 7.83 and 7.82 (17- and 18-OCOC$_6$H$_4$Br, 2xd, 8.6), 7.55 (NH9, d, hidden), 7.54 (17- and 18-OCOC$_6$H$_4$Br, d, 8.7), 5.85 (H10, t, 9.2), 5.42 (H17, qd, 4.5, 9.0), 5.12 10-OCH$_2$, d, 6.9), 4.86 (10-OCH$_2$, d, 6.8), 4.82 (4=CH$_2$, t, 1.9), 4.70 (4=CH$_2$, t, 1.7), 4.56 (H$_2$18, d, 4.5), 4.27 (H7, d, 2.9), 4.15 (H12, dd, 6.0, 9.5), 4.00 (H2, dq, 2.9, 6.6), 3.93 (7-OH, d, 2.9), 3.87 (H11, dd, 6.2, 8.7), 3.59 (H15, dd, 2.2, 9.9), 3.53 (13-OCH$_3$, s), 3.41 (H13, d, 9.5), 3.28 (6-OCH$_3$, s), 2.39 (H5(eq), d, 14.3), 2.26 (H5(ax), broad d, 14.2), 2.22 (H3, dq, 2.4, 7.1), 1.97 (H16, ddd, 2.1, 9.0, 14.6), 1.85 (H16, ddd, 3.5, 10.5, 14.5), 1.19 (2-CH$_3$, d, 6.7), 1.01 (14-CH$_3$(eq), s), 0.98 (3-CH$_3$, d, 7.1), 0.88 (14-CH$_3$(ax), s) ppm (couplings in Hz).

Mycalamide A 17,18-Di-p-bromobenzoate can be prepared as follows: Mycalamide A (5.0 mg, 0.01 mmole), p-bromobenzoyl chloride (11 mg, 0.05 mmole), dimethylaminopyridine (1 mg) and triethylamine (7 mg, 0.07 mmole) were stirred in pyridine (0.4 ml) at 75° C. overnight. H$_2$O (0.3 ml) was added, the mixture extracted with CH$_2$Cl$_2$ (3×0.4 ml), and the solvent removed (17 mg ca.). Prep RPLC (10% H$_2$O in MeOH) gave four fractions (2 mg, 1 mg, 1.2 mg, 1.1 mg) which were mycalamide A 18-mono-p-bromobenzoate and mycalamide A 7,18-di-p-bromobenzoate, obtained previously, and two new compounds, identified by PMR as pure mycalamide A 17,18-di-p-bromobenzoate and mycalamide A tri-p-bromobenzoate respectively, a white solid.

EXAMPLE 15

7-Methoxy Mycalamide A

7-Methoxy Mycalamide A has a molecular weight of 517 and a molecular formula of C$_{25}$H$_{43}$NO$_{10}$. Its molecular structure is as follows:

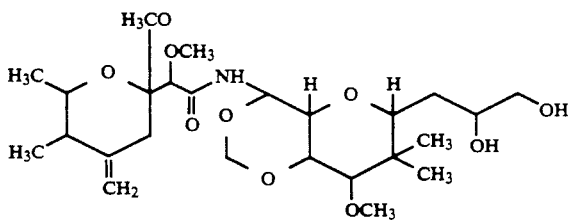

The compound is characterized as follows:

DCIMS (NH$_3$): 535 (10%, M+NH$_4^+$), 505 (28%), 504 (28%), 503 (100%, M+NH$_4^+$—CH$_3$OH), 488 (12%), 487 (9%), 486 (30%, MH$^+$—CH$_3$OH).

$^1$H NMR (CDCl$_3$): δ 7.18 (NH9, d, 10.0), 5.91 (H10, t, 10.0), 5.14 (10-OCH$_2$, d, 6.9), 4.85 (10-OCH$_2$, d, 6.9), 4.82 (4=CH$_2$, t, 1.9), 4.71 (4=CH$_2$, t, 1.8), 4.24 (H12, dd, 6.9, 10.6), 3.90 (H2, dq, 2.6, 6.7), 3.88 (H7, s), 3.87 (H11, dd, 6.9, 10.0), 3.75 (H17, m), 3.64 (H15, dd, 5.1, 6.5), 3.60 (H18, dd, 3.4, 11.0), 3.56 (7- and 13-OCH$_3$, s), 3.48 (H13, d, 10.6), 3.38 (H18, dd, 6.0, 11.0), 3.28 (6-OCH$_3$, s), 2.43 (H5(ax), td, 2.0, 14.3), 2.32 (H5(eq), d, 14.1), 2.19 (H3, dq, 2.6, 7.0), 1.56 (H$_2$16, m), 1.17 (2-CH$_3$, d, 6.6), 0.97 (14-CH$_3$(eq), s), 0.96 (3-CH$_3$, d, 7.0), 0.88 (14-CH$_3$(ax), s) ppm (couplings in Hz).

$^{13}$C NMR (CDCl$_3$): δ 170.56 (C8), 146.27 (C4), 109.95 (4=CH$_2$), 100.02 (C6), 86.83 (10-OCH$_2$), 82.99 (C7), 79.22 (C13), 78.99 (C15), 74.55 (C12), 73.22 (C10), 71.65 (C17), 71.60 (C11), 69.40 (C2), 66.68 (C18), 61.89 (13-OCH$_3$), 60.50 (7-OCH$_3$), 49.18 (6-OCH$_3$), 41.81 (C14), 41.40 (C3), 34.14 (C5), 32.03 (C16), 22.98 (14-CH$_3$(eq)), 17.81 (2-CH$_3$), 13.24 (14-CH$_3$(ax)), 11.77 (3-CH$_3$).

7-methoxy mycalamide A can be prepared as follows: Mycalamide A (7 mg), Ag$_2$O (55 mg) and MeI (21 mg), were stirred in benzene (0.4 ml) at 95° C. in a sealed vial for 1.5 hours. The solution was filtered over celite and the solvent removed (7.3 mg). Preparative TLC (developed twice in 1:7 PE:EtOAc) gave four fractions (0.8 mg, 1.4 mg, 2.0 mg, 2.8 mg) which were mycalamide A, 7-methoxy A, 3:2 17-methoxy A:18-methoxy A, and pure 18-methoxy A by nmr respectively. Subsequently 7-methoxy mycalamide A was subjected to further chromatography (prep. TLC, developed 3× in 1:5 PE:EtOAc) to give the pure compound (1.2 mg), an oil.

EXAMPLE 16

7,18-Dimethoxy Mycalamide A 7,18-Dimethoxy Mycalamide A has a molecular weight of 531 and a molecular formula of $C_{26}H_{45}NO_{10}$. Its molecular structure is as follows:

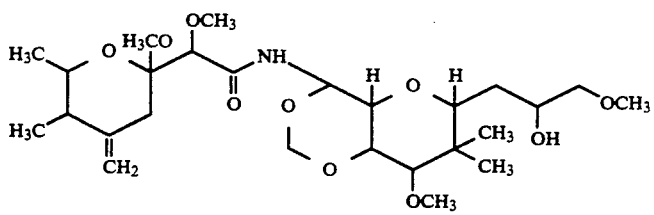

The compound is characterized as follows:

DCIMS (NH$_3$): 549 (7%, M+NH$_4$+), 519 (22%), 518 (30%), 517 (100%, M+NH$_4$+—CH$_3$OH), 502 (11%), 501 (16%), 500 (53%, MH+—CH$_3$OH).

$^1$H NMR (CDCl$_3$): δ 7.13 (NH9, d, 9.9), 5.90 (H10, t, 10.0), 5.14 (10-OCH$_2$, d, 7.0), 4.83 (10-OCH$_2$, d, 7.0), 4.81 (4=CH$_2$, t, 1.8), 4.70 (4=CH$_2$, t, 1.9), 4.23 (H12, dd, 6.8, 10.5), 3.89 (H2, dq, 2.7, 6.6), 3.88 (H7, s), 3.88 (H11, dd, 6.7, 9.8), 3.82 (H17, m), 3.58 (H15, m), 3.55 (13-OCH$_3$, s), 3.54 (7-OCH$_3$, s), 3.47 (H13, d, 10.8), 3.35 (18-OCH$_3$, s), 3.30 (H18, dd, 4.6, 9.6), 3.28 (6-OCH$_3$, s), 3.26 (H18, dd, 5.7, 9.7), 2.44 (H5(ax), td, 1.9, 14.3), 2.31 (H5(eq), d, 14.5), 2.18 (H3, dq, 2.6, 7.2), 1.6 and 1.52 (H$_2$16, m), 1.16 (2-CH$_3$, d, 6.6), 0.97 (14-CH$_3$(eq), s), 0.96 (3-CH$_3$, d, 7.2), 0.88 (14-CH$_3$(ax), s) ppm (couplings in Hz).

$^{13}$C NMR (CDCl$_3$): δ 170.43 (C8), 146.45 (C4), 109.79 (4=CH$_2$), 99.97 (C6), 86.74 (10-OCH$_2$), 83.16 (C7), 79.38 (C13), 79.08 (C15), 76.19 (C18), 74.47 (C12), 73.07 (C10), 71.26 (C11), 69.96 (C17), 69.32 (C2), 61.86 (13-OCH$_3$), 60.45 (7-OCH$_3$), 59.10 (18-OCH$_3$), 49.14 (6-OCH$_3$), 41.81 (C14), 41.45 (C3), 34.20 (C5), 32.48 (C16), 23.03 (14-CH$_3$(eq)), 17.80 (2-CH$_3$), 13.35 (14-CH$_3$(ax)), 11.73 (3-CH$_3$).

7,18-dimethoxy mycalamide A can be prepared as follows: Mycalamide A (4.2 mg), Ag$_2$O (25 mg) and MeI (18 mg), were stirred in benzene (0.3 ml) at 80° C. in a sealed vial for 3 days. The solution was filtered over celite and the solvent removed (4.6 mg). Preparative TLC (developed in EtOAc) gave three fractions (0.5 mg, 1.2 mg, 2.0 mg) which were 7,17-dimethoxy mycalamide A, 7,18-dimethoxy A and 7,17,18-trimethoxy A by nmr respectively. These were individually rechromatographed by prep. TLC to give the pure compounds, an oil.

EXAMPLE 17

18-Methoxy Mycalamide A

18-Methoxy Mycalamide A has a molecular weight of 517 and a molecular formula of $C_{25}H_{43}NO_{10}$. Its molecular structure is as follows:

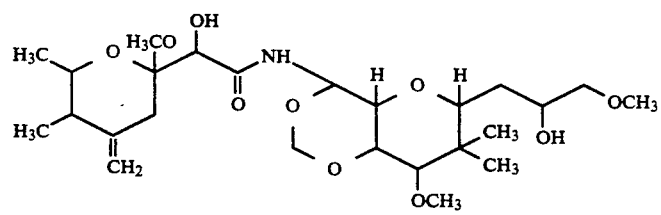

The compound is characterized as follows:

DCIMS (NH$_3$): 535 (16%, M+NH$_4$+), 505 (24%), 504 (33%), 503 (100%, M+NH$_4$+—CH$_3$OH), 487 (19%), 486 (66%, MH+—CH$_3$OH).

$^1$H NMR (CDCl$_3$): δ 7.49 (NH9, d, 9.8), 5.85 (H10, t, 9.6), 5.13 (10-OCH$_2$, d, 6.9), 4.87 (10-OCH$_2$, d, 6.9), 4.84 (4=CH$_2$, t, 1.6), 4.74 (4=CH$_2$, t, 1.5), 4.29 (H7, s), 4.21 (H12, dd, 6.6, 10.2), 4.00 (H2, dq, 2.7, 6.5), 3.84 (H11, dd, 6.6, 9.6), 3.79 (H17, m), 3.55 (13-OCH$_3$, s), 3.54 (H15, m), 3.44 (H13, d, 10.1), 3.35 (18-OCH$_3$, s), 3.32 (H18, dd, 4.2, 9.5), 3.30 (6-OCH$_3$, s), 3.23 (H18, dd, 6.2, 9.6), 2.38 (H5(eq), d, 13.9), 2.31 (H5(ax), td, 1.7, 14.0), 2.24 (H3, dq, 2.6, 7.1), 1.60 and 1.54 (H$_2$16, m), 1.19 (2-CH$_3$, d, 6.6), 1.01 (3-CH$_3$, d, 7.1), 0.99 (14-CH$_3$(eq), s), 0.87 (14-CH$_3$(ax), s) ppm (couplings in Hz).

$^{13}$C NMR (CDCl$_3$): δ 171.73 (C8), 145.50 (C4), 110.71 (4=CH$_2$), 99.85 (C6), 86.72 (10-OCH$_2$), 79.34 (C13), 78.56 (C15), 76.05 (C18), 74.31 (C12), 73.83 (C10), 72.52 (C7), 70.87 (C11, broad), 69.71 (C17), 69.48 (C2), 61.77 (13-OCH$_3$), 59.05 (18-OCH$_3$), 48.86 (6-OCH$_3$), 41.54 (C14), 41.35 (C3), 33.72 (C5), 32.49 (C16), 23.25 (14-CH$_3$(eq)), 17.93 (2-CH$_3$), 13.72 (14-CH$_3$(ax), broad), 12.07 (3-CH$_3$).

18-methoxy mycalamide A can be prepared as follows: Mycalamide A (7 mg), Ag$_2$O (55 mg) and MeI (21 mg), were stirred in benzene (0.4 ml) at 95° C. in a sealed vial for 1.5 hours. The solution was filtered over celite and the solvent removed (7.3 mg). Preparative TLC (developed twice in 1:7 PE:EtOAc) gave four fractions (0.8 mg, 1.4 mg, 2.0 mg, 2.8 mg) which were mycalamide A, 7-methoxy A, 3:2 17-methoxy A:18-methoxy A, and pure 18-methoxy A by nmr respectively, an oil.

EXAMPLE 18

7',17,18-Trimethoxy, N-Methyl Mycalamide A

7',17,18-Trimethoxy, N-Methyl Mycalamide A has a molecular weight of 559 and a molecular formula of $C_{28}H_{49}NO_{10}$. Its molecular structure is as follows:

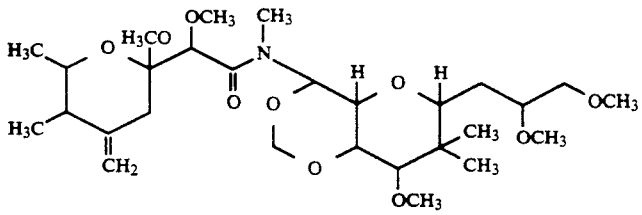

The compound is characterized as follows:

DCIMS (NH$_3$): 577 (8%, M+NH$_4^+$), 547 (15%), 546 (30%), 545 (88%, M+NH$_4^+$—CH$_3$OH), 530 (19%), 529 (37%), 528 (100%, MH$^+$—CH$_3$OH).

$^1$H NMR (CDCl$_3$): δ 6.33 (H10, d, 10.2), 5.13 (10-OCH$_2$, d, 6.7), 4.85 (10-OCH$_2$, d, 6.7), 4.82 (4=CH$_2$, t, 2.0), 4.73 (4=CH$_2$, t, 2.0), 4.27 (H12, dd, 6.9, 10.6), 4.16 (H7, s), 4.12 (H11, dd, 6.9, 10.3), 3.94 (H2, dq, 2.6, 6.6), 3.56 (7-OCH$_3$, s), 3.55 (13-OCH$_3$, s), 3.52 (H13, d, 10.7), 3.49 (H18, dd, 3.0, 10.1), 3.37 (H18, dd, 3.6, 10.0), 3.35 (18-OCH$_3$, s), 3.33 (H15, broad d, 9.2), 3.30 (17-OCH$_3$, s), 3.26 (6-OCH$_3$, s), 3.23 (H17, m), 3.11 (N-CH$_3$, s), 2.80 (H5(ax), td, 2.0, 14.6), 2.63 (H5(eq), d, 14.7), 2.21 (H3, dq, 2.4, 7.2), 1.83 (H16, broad dd, 9.4, 14.3), 1.42 (H16, m), 1.14 (2-CH$_3$, d, 6.6), 1.04 (3-CH$_3$, d, 7.0), 0.97 (14-CH$_3$(eq), s). 0.86 (14-CH$_3$(ax), s) ppm (couplings in Hz).

$^{13}$C NMR (CDCl$_3$): δ 109.72 (4=CH$_2$), 101.78 (C6), 87.00 (10-OCH$_2$), 81.15 (C7), 79.11 (C13), 77.3 (C10), 76.09 (C15), 74.69 (C12), 72.01 (C18), 69.18 (C2), 67.27 (C11), 61.85 (13-OCH$_3$), 59.22 (18-OCH$_3$), 56.42 (17-OCH$_3$), 50.48 (6-OCH$_3$), 41.41 (C3), 33.24 (C5), 30.06 (C16), 28.90 (N-CH$_3$), 23.01 (14-CH$_3$(eq)), 17.99 (2-CH$_3$), 12.97 (14-CH$_3$(ax)), 12.08 (3-CH$_3$). NB: C4, C6, C8, 7-OCH$_3$, C14, C17 not observed.

7',17,18-trimethoxy, N-methyl mycalamide A can be prepared as follows: Mycalamide A (4 mg), powdered KOH (7.2 mg) and MeI (10 mg) were stirred in DMSO (0.3 ml) at room temperature for 20 hours, then at 40° C. for 4 hours. H$_2$O was added (0.5 ml) and the mixture transferred onto a reverse phase pipette column (200 mg C18, equilibrated to H$_2$O), flushed with H$_2$O (6 ml) and then eluted with MeOH (6 ml). The MeOH fraction was evaporated to dryness (4.3 mg), then subjected to prep TLC (developed in EtOAc). Three fractions of silica were recovered and each eluted with 1:9 EtOH:EtOAc (4 ml) to give three fractions on evaporation (0.5 mg, 1.5 mg, 1 mg) which were 7,18-dimethoxy, N-methyl mycalamide A, 7,17,18-trimethoxy, N-methyl mycalamide A and 7',17,18-trimethoxy, N-methyl mycalamide A by nmr respectively, an oil.

EXAMPLE 19

Mycalamide B Trans-Oxazolidinone

Mycalamide B Trans-Oxazolidinone has a molecular weight of 487 and a molecular formula of C$_{24}$H$_{41}$NO$_9$. Its molecular structure is as follows:

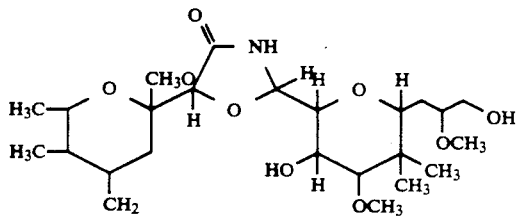

The compound is characterized as follows:

HRFABMS: 510.26340 (M+Na$^+$, −8.8 ppm).

FABMS: 511 (26%), 510 (100%, M+Na$^+$), 457 (22%), 456 (67%, MH$^+$—CH$_3$OH).

$^1$H NMR (CDCl$_3$): δ 5.57 (H10, dd, 2.2, 6.1), 4.84 (4=CH$_2$, t, 2.0), 4.72 (4=CH$_2$, t, 1.8), 4.38 (H7, d, 2.2), 3.97 (H12, dd, 5.1, 7.4), 3.94 (H2, dq, 2.6, 6.6), 3.80 (H11, dd, 5.1, 6.1), 3.78 (H18, dd, 4.6, 9.7), 3.62 (H18, dd, 5.9, 9.9), 3.54 (13-OCH$_3$, s), 3.5 (H17, m), 3.43 (17-OCH$_3$, s), 3.40 (H15, dd, 2.6, 10.9), 3.30 (6-OCH$_3$, s), 2.93 (H13, d, 7.3), 2.47 (H5(ax), td, 2.0, 13.7), 2.32 (H5(eq), d, 13.8), 2.21 (H3, dq, 2.6, 6.7), 1.85 (H16, m), 1.7 (H16, m), 1.18 (2-CH$_3$, d, 6.6), 1.04 (3-CH$_3$, d, 6.8), 1.03 (14-CH$_3$(eq), s), 0.88 (14-CH$_3$(ax), s) ppm (couplings in Hz). NB: NH9 not observed.

Mycalamide B trans-oxazolidinone can be prepared as follows: Mycalamide B (2.5 mg) was dissolved in a solution of 1M NaOMe in methanol (0.3 ml) and stirred at 50° C. for 24 hours. The solvent was removed and the residue partitioned in 1:1 CHCl$_3$:H$_2$O (5 ml) and then extracted with CHCl$_3$ (3×2 ml). Prep TLC of this extract (developed twice in 1:19 EtOH:EtOAc) gave two fractions (1 mg, 0.9 mg), which were cis and trans isomers respectively at C7–C10 of mycalamide B oxazolidinone by nmr, although the second fraction also contained up to 25% unreacted mycalamide B, an oil.

EXAMPLE 20

Mycalamide B Cis-Oxazolidinone

Mycalamide B cis-Oxazolidinone has a molecular weight of 487 and a molecular formula of C$_{24}$H$_{41}$NO$_9$. Its molecular structure is as follows:

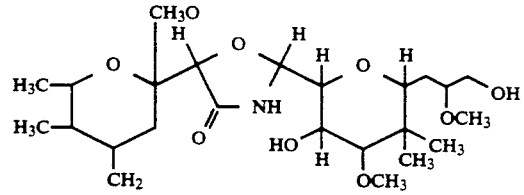

The compound is characterized as follows:

FABMS: 511 (17%), 510 (100%, M+Na$^+$), 456 (82%, MH$^+$—CH$_3$OH).

$^1$H NMR (CDCl$_3$): δ 6.65 (NH9, broad s), 5.52 (H10, dd, 1.6, 8.8), 4.82 (4=CH$_2$, t, 1.8), 4.70 (4=CH$_2$, t, 1.9), 4.34 (H7, d, 1.6), 3.94 (H12, dd, 6.7, 9.6), 3.93 (H2, dq, 2.3, 6.6), 3.84 (H11, dd, 6.6, 8.7), 3.79 (H18, dd, 4.6, 11.7), 3.69 (H18, dd, 5.1, 11.7), 3.64 (H17, m), 3.59 (13-OCH$_3$, s), 3.46 (H15, dd, 4.0, 8.3), 3.38 (17-OCH$_3$, s), 3.30 6-OCH$_3$, s), 2.95 (H13, d, 9.8), 2.39 (H5(ax), td, 1.8, 13.7), 2.33 (H5(eq), d, 13.8), 2.19 (H3, dq, 2.4, 7.0), 1.65 (H$_2$16, m), 1.19 (2-CH$_3$, d, 6.6), 1.04 (3-CH$_3$, d, 7.0), 0.97 (14-CH$_3$(eq), s), 0.89 (14-CH$_3$(ax), s) ppm (couplings in Hz).

13C NMR (CDCl3): δ 109.64 (4=CH2), 98.32 (C6), 88.02 (C13), 80.84 (C10), 78.92 (C17), 75.63 (C15), 74.96 (C7), 69.18 (C2), 69.04 (C12), 63.00 (13-OCH3), 62.94 (C18), 56.94 (17-OCH3), 48.62 (6-OCH3), 41.77 (C3), 33.81 (C5), 29.45 (C16), 23.41 (14-CH3(eq)), 17.89 (2-CH3), 13.67 (14-CH3(ax)), 11.77 (3-CH3). NB: C4, C8, C11, C14 not observed.

Mycalamide B cis-oxazolidinone can be prepared as follows: Mycalamide B (2.5 mg) was dissolved in a solution of 1M NaOMe in methanol (0.3 ml) and stirred at 50° C. for 24 hours. The solvent was removed and the residue partitioned in 1:1 CHCl3H2O (5 ml) and then extracted with CHCl3 (3×2 ml). Prep TLC of this extract (developed twice in 1:19 EtOH:EtOAc) gave two fractions (1 mg, 0.8 mg), which were cis and trans isomers respectively at C7-C10 of mycalamide B oxazolidinone by nmr, although the second fraction also contained up to 25% unreacted mycalamide B, an oil.

EXAMPLE 21

Mycalamide B Bis-Ethylcarbonate Hydrochloride

Mycalamide B Bis-Ethylcarbonate Hydrochloride has a molecular weight of 666 and a molecular formula of C30H48ClNO13. Its molecular structure is as follows:

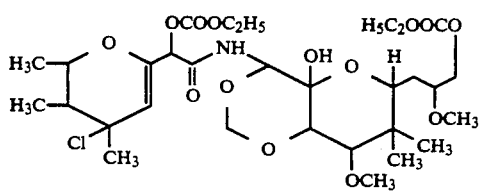

The compound is characterized as follows:
1H NMR (CDCl3): δ 5.67 (H10, t, 9.4), 5.35 (H7, d, 1.0), 5.15 (H5, d, 1.1), 5.14 (10-OCH2, d, 7.1), 4.88 (10-OCH2, d, 6.9), 4.22 (H12, dd, 6.7, 10.6), 4.19 (H18, dd, 3.2, 11.7), 4.18 (H2, dq, 2.8, 6.5), 4.15 (7- and 18-OCOOCH2, q, 7.0), 4.04 (H18, dd, 5.1, 11.7), 3.94 (H11, dd, 6.6, 9.7), 3.56 (13-OCH3, s), 3.44 (H13, d, 10.2), 3.36 (H17, m), 3.35 (H15, dd, 2.4, 8.1), 3.26 (17-OCH3, s), 2.53 (H3, broad dq, 2.8, 6.9), 1.7 and 1.62 (H216, m), 1.58 (4-CH3, s), 1.30 (2-CH3, d, 6.5), 1.27 (2x-OCH2CH3, t, 7.1), 1.03 (3-CH3, d, 7.0), 0.99 (14-CH3(eq), s), 0.87 (14-CH3(ax), s) ppm (couplings in Hz). NB: NH9 not observed.

Mycalamide B bis-ethylcarbonate hydrochloride can be prepared as follows: Mycalamide B (2.5 mg ca.), K2CO3 (8.5 mg) and ethyl chloroformate 4.5 mg) were stirred in benzene (0.3 ml) for 20 hours at room temperature. The solution was then diluted with benzene, filtered over celite and the solvent removed. Prep TLC (developed in 3:2 PE:EtOAc) gave 0.8 mg of the major component, which was pure mycalamide B bis-ethylcarbonate hydrochloride by PMR.

EXAMPLE 22

Mycalamide B 18-Monoacetate

Mycalamide B 18-Monoacetate has a molecular weight of 559 and a molecular formula of C27H45NO11. Its molecular structure is as follows:

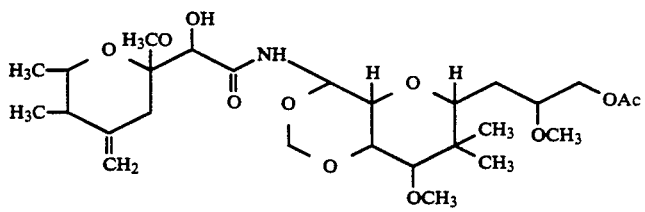

The compound is characterized as follows:
DCIMS (NH3): 577 (1%, M+NH4+), 560 (1%, MH+), 547 (15%), 546 (35%), 545 (100%, M+NH4+—CH3OH), 530 (16%), 529 (27%), 528 (88%, MH+—CH3OH).

1H NMR (CDCl3): δ 7.50 (NH9, d, 9.6), 5.78 (H10, t, 9.5), 5.11 (10-OCH2, d, 7.0), 4.87 (4=CH2, t, 2.0), 4.85 (10-OCH2, d, 7.0), 4.73 (4=CH2, t, 1.9), 4.26 (H7, s), 4.20 (H18, dd, 2.6, 12.3), 4.20 (H12, dd, 6.5, 10.0), 4.09 (H18, dd, 5.3, 12.2), 4.05 (H2, dq, 2.9, 6.5), 3.90 (7-OH, broad s), 3.78 (H11, dd, 6.7, 9.5), 3.55 (13-OCH3, s), 3.42 (H13, d, 10.1), 3.38 (H15, m), 3.31 (6-OCH3, s), 3.30 (H17, m), 3.24 (17-OCH3, s), 2.36 (H5(eq), d, 14.0), 2.27 (H3, dq, 2.7, 7.1), 2.17 (H5(ax), td, 2.1, 14.1), 2.08 (18-OCOCH3, s), 1.60 (H216, m), 1.21 (2-CH3, d, 6.6), 1.02 (3-CH3, d, 7.1), 0.97 (14-CH3(eq), s), 0.86 (14-CH3(ax), s) ppm (couplings in Hz).

13C NMR (CDCl3): δ 171.69 (C8), 171.04 (18-OCO), 144.95 (C4), 111.25 (4=CH2), 100.00 (C6), 86.43 (10-OCH2), 79.27 (C13), 76.26 (C17), 75.61 (C15), 74.26 (C12), 74.05 (C10), 71.11 (C7), 70.80 (C11, broad), 69.54 (C2), 64.14 (C18), 61.76 (13-OCH3), 56.98 (17-OCH3), 48.51 (6-OCH3), 41.40 (C14), 41.31 (C3), 33.59 (C5), 30.29 (C16), 23.28 (14-CH3(eq)), 20.97 (18-OCOCH3), 18.01 (2-CH3), 13.60 (14-CH3(ax), broad), 12.22 (3-CH3).

Mycalamide B 18-monoacetate can be prepared as follows: Mycalamide B diacetate (2.5 mg) was stirred with 0.5 mg K2CO3 in 9:1 MeOH:H2O (0.5 ml) for 1 hour at room temperature. H2O (2.5 ml) was added and the mixture extracted with CH2Cl2 (3×2 ml). The solvent was removed and the combined organic extracts were subjected to preparative TLC (developed in ethyl acetate). Two bands of silica were recovered (Rf=0.7 and 0.2) and eluted with 1:3 EtOH:EtOAc, giving two fractions on evaporation (1.7 mg, 0.5 mg) which were pure mycalamide B 18-monoacetate and mycalamide B respectively by nmr, an oil.

EXAMPLE 23

18-Methoxy, Mycalamide B 7-Monoacetate

18-Methoxy, Mycalamide B 7-Monoacetate has a molecular weight of 573 and a molecular formula of C28H47NO11. Its molecular structure is as follows:

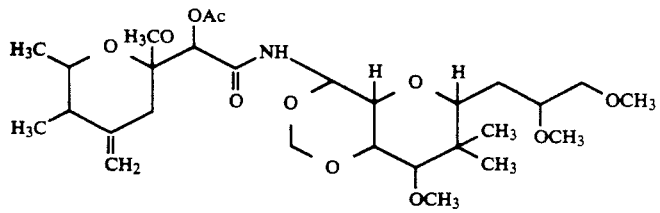

The compound is characterized as follows:

DCIMS (NH$_3$): 592 (10%), 591 (32%, M+NH$_4$+), 561 (26%), 560 (33%), 559 (100%, M+NH$_4$+—CH$_3$OH), 544 (10%), 543 (14%), 542 (43%, MH+—CH$_3$OH).

$^1$H NMR (CDCl$_3$): δ 7.38 (NH9, d, 9.4), 5.78 (H10, t, 9.5), 5.48 (H7, s), 5.08 (10-OCH$_2$, d, 6.9), 4.88 (4=CH$_2$, t, 1.7), 4.85 (10-OCH$_2$, d, 6.9), 4.76 (4=CH$_2$, t, 1.7), 4.18 (H12, dd, 6.5, 10.0), 4.03 (H2, dq, 2.8, 6.7), 3.75 (H11, dd, 6.4, 9.3), 3.54 (13-OCH$_3$, s), 3.46 (H18, dd, 2.4, 10.5), 3.39 (H13, d, 10.1), 3.37 (18-OCH$_3$, s), 3.34 (H15, m), 3.32 (H18, dd, 5.0, 10.5), 3.26 (17-OCH$_3$, s), 3.24 (H17, m), 3.17 (6-OCH$_3$, s), 2.43 (H5(ax), td, 1.8, 14.2), 2.36 (H5(eq), d, 14.2), 2.28 (H3, dq, 2.9, 7.2), 2.20 (7-OCOCH$_3$, s), 1.65 (H16, m), 1.60 (H16, m), 1.22 (2-CH$_3$, d, 6.6), 1.05 (3-CH$_3$, d, 7.1), 0.98 (14-CH$_3$(eq), s), 0.86 (14-CH$_3$(ax), s) ppm (couplings in Hz).

$^{13}$C NMR (CDCl$_3$): δ 169.60 (C8), 166.79 (7-OCO), 144.73 (C4), 111.31 (4=CH$_2$), 99.26 (C6), 86.48 (10-OCH$_2$), 79.55 (C13), 77.34 (C17), 76.08 (C15), 74.22 (C12), 73.79 (C10), 72.21 (C18), 71.45 (C7), 70.58 (C11, broad), 70.00 (C2), 61.71 (13-OCH$_3$), 59.11 (18-OCH$_3$), 56.84 (17-OCH$_3$), 48.50 (6-OCH$_3$), 41.32 (C14), 41.17 (C3), 34.36 (C5), 30.00 (C16), 23.46 (14-CH$_3$(eq)), 20.63 (7-OCOCH$_3$), 17.94 (2-CH$_3$), 13.81 (14-CH$_3$(ax), broad), 12.26 (3-CH$_3$).

18-methoxy, mycalamide B 7-monoacetate can be prepared as follows: Mycalamide B (6 mg), Ag$_2$O (40 mg) and MeI (27 mg) were stirred in benzene (0.4 ml) for 2 hours at 90° C. The solution was filtered over celite and the solvent removed. Pyridine (0.1 ml) and acetic anhydride (0.1 ml) were added and the mixture stirred at room temperature for 16 hours. H$_2$O was added (2.5 ml) and the solution extracted with CH$_2$Cl$_2$ (2×2 ml). Prep TLC of this extract (3:1 EtOAc:PE) gave three fractions (1.7 mg, 2.0 mg, 2.4 mg) which were pure 7-methoxy mycalamide B 18-acetate, 18-methoxy mycalamide B 7-monoacetate, and mycalamide B diacetate respectively by nmr, an oil.

EXAMPLE 24

Mycalamide B 7-Mono-p-Bromobenzoate

Mycalamide B 7-Mono-p-Bromobenzoate has a molecular weight of 700 and a molecular formula of C$_{32}$H$_{46}$BrNO$_{11}$. Its molecular structure is as follows:

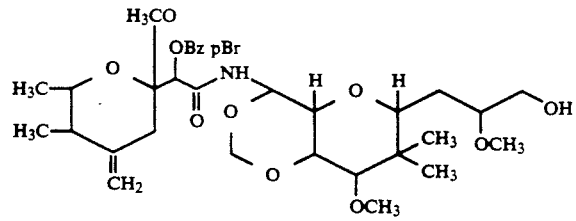

The compound is characterized as follows:

$^1$H NMR (CDCl$_3$): δ 7.98 (7-OCOC$_6$H$_4$Br, d, 8.7), 7.62 (7-OCOC$_6$H$_4$Br, d, 8.6), 7.48 (NH9, d, 9.8), 5.79 (H10, t, 9.5), 5.74 (H7, s), 5.11 (10-OCH$_2$, d, 7.1), 4.94 (4=CH$_2$, m), 4.89 (10-OCH$_2$, d, 7.0), 4.83 (4=CH$_2$, m), 4.24 (H12, dd, 7.0, 10.5), 4.09 (H2, dq, 2.9, 6.3), 3.78 (H11, dd, 7.0, 9.5), 3.65 (H18, dd, 1.9, 12.2), 3.56 (13-OCH$_3$, s), 3.42 (H13, d, 10.7), 3.4 (H15, m), 3.36 (H18, dd, 6.8, 12.4), 3.28 (17-OCH$_3$, s), 3.20 (6-OCH$_3$, s), 3.2 (H17, m), 2.59 (H5(ax), broad d, 14.0), 2.53 (H5(eq), d, 13.8), 2.33 (H3, dq, 2.5, 6.9), 1.5–1.6 (H$_2$16, m), 1.28 (2-CH$_3$, d, 6.5), 1.10 (3-CH$_3$, d, 7.1), 0.95 (14-CH$_3$(eq), s), 0.86 (14-CH$_3$(ax), s) ppm (couplings in Hz).

A minor product (0.8 mg), isolated from the p-bromobenzoylation of mycalamide B (see Example 25), was found to be mycalamide B 7-mono-p-bromobenzoate by PMR, a white solid.

EXAMPLE 25

Mycalamide B 18-Mono-p-Bromobenzoate

Mycalamide B 18-Mono-p-Bromobenzoate has a molecular weight of 700 and a molecular formula of C$_{32}$H$_{46}$BrNO$_{11}$. Its molecular structure is as follows:

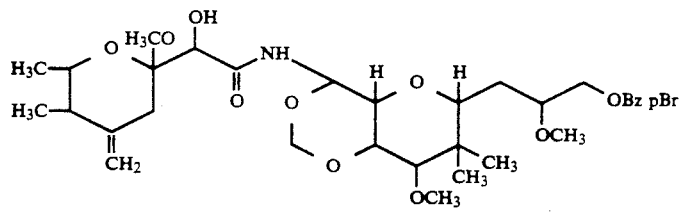

The compound is characterized as follows:

$^1$H NMR (CDCl$_3$): δ 7.91 (18-OCOC$_6$H$_4$Br, d, 8.5), 7.59 (18-OCOC$_6$H$_4$Br, d, 8.6), 7.51 (NH9, d, 9.7), 5.82 (H10, t, 9.5), 5.13 (10-OCH$_2$, d, 7.0), 4.88 (4=CH$_2$, m), 4.87 (10-OCH$_2$, d, 6.9), 4.73 (4=CH$_2$, t, 1.9), 4.48 (H18, dd, 2.3, 12.5), 4.36 (H18, dd, 5.0, 12.2), 4.25 (H7, d, 2.1), 4.21 (H12, dd, 6.6, 10.2), 4.06 (H2, dq, 2.8, 6.5), 3.83 (7-OH, d, 2.4), 3.82 (H11, dd, 6.7, 9.5), 3.56 (13-OCH$_3$, s), 3.47 (H15, broad d, 9.5), 3.45 (H17, m), 3.44 (H13, d, 10.0), 3.31 and 3.30 (6-OCH$_3$ and 17-OCH$_3$, 2xs), 2.36 (H5(eq), d, 14.1), 2.29 (H3, dq, 2.9, 7.2), 2.17 (H5(ax), td, 1.9, 14.1), 1.69 (H16, ddd, 2.0, 9.6, 14.8), 1.6 (H16, m), 1.21 (2-CH$_3$, d, 6.6), 1.03 (3-CH$_3$, d, 7.1), 0.98 (14-CH$_3$(eq), s), 0.88 (14-CH$_3$(ax), s) ppm (couplings in Hz).

$^{13}$C NMR (CDCl$_3$): δ 171.69 (C8), 145.01 (C4), 131.78, 131.14, 129.03 and 128.18 (18-OCOC$_6$H$_4$Br), 111.19 (4=CH$_2$), 99.93 (C6), 86.40 (10-OCH$_2$), 79.33 (C13), 76.47 (C17), 75.67 (C15), 74.19 (C12), 74.00 (C10), 71.31 (C7), 70.70 (C11, broad), 69.55 (C2), 64.48 (C18), 61.73 (13-OCH$_3$), 57.09 (17-OCH$_3$), 48.57 (6-OCH$_3$), 41.50 (C14), 41.31 (C3), 33.58 (C5), 30.49 (C16), 23.39 (14-CH$_3$(eq)), 18.00 (2-CH$_3$), 13.78 (14-CH$_3$(ax), broad), 12.20 (3-CH$_3$). NB: 18-OCO not observed.

Mycalamide B 18-mono-p-bromobenzoate can be prepared as follows: Mycalamide B (10–12 mg), p-bromobenzoyl chloride (26 mg), dimethylaminopyridine (1 mg), and triethylamine (15 mg) were stirred in pyridine (0.8 ml) at 50° C. for one week. After concentrating to 0.1 ml, H$_2$O (0.3 ml) was added, the mixture extracted with CH$_2$Cl$_2$ (4×0.4 ml) and the solvent removed (50 mg ca). Prep RPLC (10% H$_2$O in MeOH, then 18% H$_2$O in MeOH) gave four fractions overall (1.2 mg, 0.8 mg, 5.2 mg, 2.4 mg) which were mycalamide B, mycalamide B 7- and 18-mono-, and mycalamide B di-p-bromobenzoates by PMR respectively, a white solid.

EXAMPLE 26

Mycalamide B Di-p-Bromobenzoate

Mycalamide B Di-p-Bromobenzoate has a molecular weight of 883 and a molecular formula of C$_{39}$H$_{49}$Br$_2$NO$_{12}$. Its molecular structure is as follows:

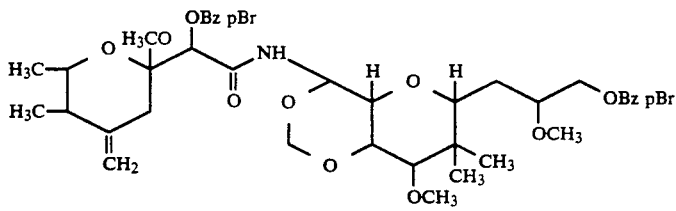

The compound is characterized as follows:
DCIMS (NH$_3$): 872 (15%), 871 (55%), 870 (32%), 869 (100%, M+NH$_4$+—CH$_3$OH), 868 (16%), 867 (51%), 854 (17%), 853 (8%), 852 (52%, MH+—CH$_3$OH), 850 (18%).

$^1$H NMR (CDCl$_3$): δ 7.90 and 7.85 (18- and 7-OCOC$_6$H$_4$Br, 2xd, 8.5), 7.57 and 7.54 (18- and 7-OCOC$_6$H$_4$Br, d, 8.5), 7.28 (NH9, d, 9.6), 5.79 (H10, t, 9.4), 5.63 (H7, s), 5.08 (10-OCH$_2$, d, 6.7), 4.91 (4=CH$_2$, m), 4.87 (10-OCH$_2$, d, 6.9), 4.79 (4=CH$_2$, m), 4.54 (H18, dd, 3.0, 12.3), 4.28 (H18, dd, 4.2, 12.4), 4.17 (H12, dd, 6.5, 9.8), 4.05 (H2, dq, 2.6, 6.6), 3.80 (H11, dd, 6.3, 8.9), 3.53 (13-OCH$_3$, s), 3.46 (H15, broad d, 9.1), 3.45 (H17, m), 3.38 (H13,d, 9.7), 3.31 (17-OCH$_3$, s), 3.19 (6-OCH$_3$, s), 2.52 (H5(ax), broad d, 13.5), 2.45 (H5(eq), d, 13.9), 2.30 (H3, dq, 2.7, 6.9), 1.7 (H16, m), 1.58 (H16, m), 1.23 (2-CH$_3$, d, 6.6), 1.07 (3-CH$_3$, d, 7.1) 0.96 (14-CH$_3$(eq), s), 0.87 (14-CH$_3$(ax), s) ppm (couplings in Hz).

$^{13}$C NMR (CDCl$_3$): δ 166.63 (C8), 144.74 (C4), 131.91, 131.69, 131.41, 131.14, 129.16, 128.71, 128.15 and 128.01 (7- and 18-OCOC$_6$H$_4$Br), 111.37 (4=CH$_2$), 99.27 (C6), 86.52 (10-OCH$_2$), 79.52 (C13), 76.48 (C17), 75.78 (C15), 74.10 (C12), 74.08 (C10), 72.30 (C7), 70.50 (C11, broad), 70.04 (C2), 63.68 (C18), 61.67 (13-OCH$_3$), 57.01 (17-OCH$_3$), 48.62 (6-OCH$_3$), 41.22 (C3), 41.16 (C14), 34.54 (C5), 30.51 (C16), 23.56 (14-CH$_3$(eq)), 17.93 (2-CH$_3$), 14.03 (14-CH$_3$(ax), broad), 12.19 (3-CH$_3$). NB: 7-OCO and 18-OCO not observed.

Mycalamide B di-p-bromobenzoate can be prepared as follows: Mycalamide B (10–12 mg), p-bromobenzoyl chloride (26-mg), dimethylaminopyridine (1 mg), and triethylamine (15 mg) were stirred in pyridine (0.8 ml) at 50° C. for one week. After concentrating to 0.1 ml, H$_2$O (0.3 ml) was added, the mixture extracted with CH$_2$Cl$_2$ (4×0.4 ml) and the solvent removed (50 mg ca). Prep RPLC (10% H$_2$O in MeOH, then 18% H$_2$O in MeOH) gave four fractions overall (1.2 mg, 0.8 mg, 5.2 mg, 2.4 mg) which were mycalamide B, mycalamide B 7- and 18-mono-, and mycalamide B di-p-bromobenzoates by PMR respectively, a white solid.

Example 27

18-Methoxy Mycalamide B

18-Methoxy Mycalamide B has a molecular weight of 531 and a molecular formula of C$_{26}$H$_{45}$NO$_{10}$. Its molecular structure is as follows:

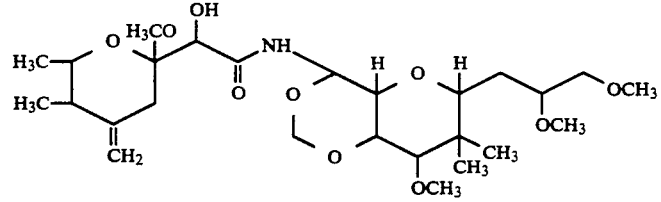

The compound is characterized as follows:
DCIMS (NH$_3$): 549 (7%, M+NH$_4$+), 520 (6%), 519 (23%), 518 (29%), 517 (99%, M+NH$_4$+—CH$_3$OH), 503 (5%), 502 (19%), 501 (29%), 500 (100%, MH+—CH$_3$OH).

$^1$H NMR (CDCl$_3$): δ 7.55 (NH9, d, 9.5), 5.81 (H10, t, 9.6), 5.13 (10-OCH$_2$, d, 6.9), 4.86 (10-OCH$_2$, d, 6.8), 4.86 (4=CH$_2$, t, 1.8), 4.74 (4=CH$_2$, t, 1.8), 4.28 (H7, d, 2.5), 4.20 (H12, dd, 6.6, 10.2), 4.05 (H2, dq, 2.9, 6.6), 3.92 (7-OH, d, 2.6), 3.79 (H11, dd, 6.6, 9.6), 3.56 (13-OCH$_3$, s), 3.46 (H18, dd, 2.2, 10.3), 3.44 (H13, d, 10.3), 3.37 (18-OCH$_3$, s), 3.37 (H15, m), 3.32 (6-OCH$_3$, s), 3.31 (H18, dd, 5.2, 10.3), 3.25 (17-OCH$_3$, s), 3.24 (H17, m), 2.37 (H5(eq), d 14.3), 2.27 (H3, dq, 2.5, 7.2), 2.20 (H5(ax), td, 1.9, 14.1), 1.62 and 1.57 (H$_2$16, m), 1.21 (2-CH$_3$, d, 6.6), 1.03 (3-CH$_3$, d, 7.1), 0.99 (14-CH$_3$(eq), s), 0.87 (14-CH$_3$(ax), s) ppm (couplings in Hz).

$^{13}$C NMR (CDCl$_3$): δ 171.78 (C8), 145.00 (C4), 111.23 (4=CH$_2$), 100.01 (C6), 86.47 (10-OCH$_2$), 79.43 (C13), 75.99 (C15), 74.33 (C12), 73.94 (C10), 72.63 (C18), 71.45 (C7), 70.62 (C11, broad), 69.58 (C2), 61.76 (13-OCH$_3$), 59.20 (18-OCH$_3$), 56.87 (17-OCH$_3$), 48.56 (6-OCH$_3$), 41.47 (C14), 41.30 (C3), 33.61 (C5), 29.95 (C16), 23.34 (14-CH$_3$(eq)), 18.01 (2-CH$_3$), 13.66 (14-CH$_3$(ax), broad), 12.28 (3-CH$_3$). NB: C17 not observed.

18-methoxy mycalamide B can be prepared as follows: 18-methoxy mycalamide B 7-monoacetate (2 mg) (see Example 23) was stirred in a solution with 0.4 mg K$_2$CO$_3$ in aqueous MeOH (0.4 ml) at room temperature for 1.5 hours. The solution was concentrated, then H$_2$O (2.5 ml) was added and the solution extracted with CH$_2$Cl$_2$ (3×2 ml). The solvent was removed to give pure 18-methoxy mycalamide B (1.8 mg) by nmr, an oil.

EXAMPLE 28

Mycalamide B 7,N-Dibenzyl Ether

Mycalamide B 7,N-Dibenzyl Ether has a molecular weight of 697 and a molecular formula of C$_{39}$H$_{55}$NO$_{10}$. Its molecular structure is as follows:

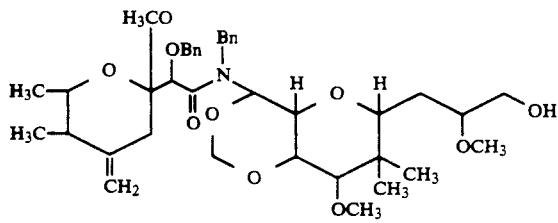

The compound is characterized as follows:
DCIMS (NH$_3$): 715 (9%, M+NH$_4$+), 686 (13%), 685 (33%), 684 (45%), 683 (100%, M+NH$_4$+—CH$_3$OH), 668 (22%), 667 (27%), 666 (63%, MH$_+$—CH$_3$OH). $^1$H NMR (CDCl$_3$): δ 7.4–7.2 (2xφ, m), 6.26 (H10, d, 8.9), 5.20 (10-OCH$_2$, d, 6.8), 5.11 (N-CH$_2$φ, d, 17.2), 4.87 (10-OCH$_2$, d, 6.6), 4.78 (4=CH$_2$, t, 1.9), 4.68 (4=CH$_2$, m), 4.61 (N-CH$_2$φ, d, 17.6), 4.39 (7-OCH$_2$φ, d, 11.5), 4.25 (H12, dd, 7.4, 9.9), 4.21 (H7, s), 4.03 (H11, broad t, 8.0), 3.97 (7-OCH$_2$φ, d, 12.1), 3.89 (H2, dq, 2.8, 6.5), 3.86 (H18, dd, 3.0, 11.8), 3.69 (H15, dd, 2.5, 8.3), 3.60 (H18, dd, 5.5, 11.8), 3.54 (13-OCH$_3$, s), 3.46 (H17, m), 3.42 (H13, d, 9.7), 3.34 (17-OCH$_3$, s), 2.96 (6-OCH$_3$, s), 2.59 (H5(ax), broad d, 14.1), 2.23 (H5(eq), d, 14.2) 2.17 (H3, dq, 2.3, 6.8), 1.62 (H16, m), 1.56 (H16, m), 1.18 (2-CH$_3$, d, 6.4), 1.02 (14-CH$_3$(eq), s), 0.98 (3-CH$_3$, d, 6.7), 0.87 (14-CH$_3$(ax), s) ppm (couplings in Hz).

Mycalamide B 7,N-dibenzyl ether can be prepared as follows: Mycalamide B (4.4 mg), powdered KOH (7 mg) and benzyl bromide (12 mg) were stirred in DMSO (0.3 ml) at room temperature for 4 minutes. H$_2$O (2 ml) was added and the mixture extracted with CHCl$_3$ (3×2 ml). The extract was evaporated to dryness, then subjected to prep TLC (developed in 1:1 PE:EtOAc). Three bands of silica were recovered and eluted with ethyl acetate to give three pure products (1.8 mg, 0.8 mg, 0.9 mg), which were mycalamide B 7-mono-; 7,N-di- and 7,18-di-benzyl ethers by NMR respectively, an oil.

EXAMPLE 29

Mycalamide B 7,18-Dibenzyl Ether

Mycalamide B 7,18-Dibenzyl Ether has a molecular weight of 697 and a molecular formula of C$_{39}$H$_{55}$NO$_{10}$. Its molecular structure is as follows:

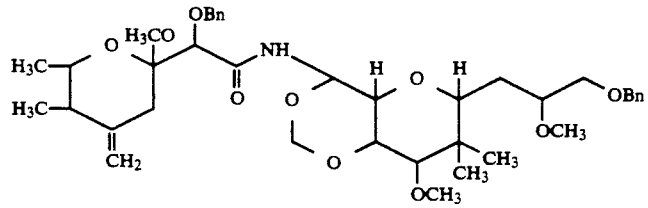

The compound is characterized as follows:
DCIMS (NH$_3$): 716 (9%), 715 (19%, M+NH$_4$+), 686 (10%), 685 (28%), 684 (45%), 683 (100%, M+NH$_4$+—CH$_3$OH), 668 (10%), 667 (16%), 666 (36%, MH+—CH$_3$OH).

$^1$H NMR (CDCl$_3$): δ 7.4–7.3 (2xφ, m), 7.22 (NH9, d, 9.8), 5.81 (H10, t, 9.8), 5.11 (10-OCH$_2$, d, 6.9), 4.81 (10-OCH$_2$, d, 6.7), 4.80 (4=CH$_2$, m), 4.72 (7-OCH$_2$φ, d, 11.3), 4.69 (4=CH$_2$, t, 1.8), 4.62 (18-OCH$_2$φ, d, 12.1), 4.54 (18-OCH$_2$φ, d, 12.0), 4.52 (7-OCH$_2$φ, d, 11.3), 4.19 (H12, dd, 6.5, 10.2), 4.01 (H7, s), 3.87 (H2, dq, 2.7, 6.6), 3.80 (H11, dd, 6.7, 9.7), 3.61 (H18, m), 3.54 (13-OCH$_3$, s), 3.45 (H18, m), 3.44 (H15, m), 3.38 (H13, d, 10.2), 3.28 (H17, m), 3.27 (17-OCH$_3$, s), 3.06 (6-OCH$_3$, s), 2.43 (H5(ax), td, 1.8, 14.3), 2.35 (H5(eq), d, 14.3), 2.18 (H3, dq, 2.9, 7.1), 1.65 (H$_2$16, m), 1.16 (2-CH$_3$, d, 6.6), 0.95 (3-CH$_3$, d, 7.1) 0.93 (14-CH$_3$(eq), s). 0.87 (14-CH$_3$(ax), s) ppm (couplings in Hz).

$^{13}$C NMR (CDCl$_3$): δ 170.17 (C8), 146.40 (C4), 138.58, 137.06, 128.51, 128.28, 128.10, 127.79 and 127.39 (7-and 18-OCH$_2$φ), 109.94 (4=CH$_2$), 99.95 (C6), 86.42 (10-OCH$_2$), 80.73 (C7), 79.55 (C13), 77.79 (C17), 75.84 (C15), 74.33 (C12), 73.98 (C10), 73.25 and 73.13 (7- and 18-OCH$_2$), 70.54 (C18), 69.34 (C2), 61.75 (13-OCH$_3$), 57.10 (17-OCH$_3$), 48.94 (6-OCH$_3$), 41.46 (C14), 41.41 (C3), 34.42 (C5), 30.11 (C16), 23.22 (14-CH$_3$(eq)), 17.83 (2-CH$_3$), 13.60 (14-CH$_3$(ax), broad), 11.82 (3-CH$_3$). NB: C$_{11}$ not observed.

Mycalamide B 7,18-dibenzyl ether can be prepared as follows: Mycalamide B (4.4 mg), powdered KOH (7 mg) and benzyl bromide (12 mg) were stirred in DMSO (0.3 ml) at room temperature for 4 minutes. H$_2$O (2 ml) was added and the mixture extracted with CHCl$_3$ (3×2 ml). The extract was evaporated to dryness, then subjected to prep TLC (developed in 1:1 PE:EtOAc). Three bands of silica were recovered and eluted with ethyl acetate to give three pure products (1.8 mg, 0.8 mg, 0.9 mg), which were mycalamide B 7-mono-; 7,N-di- and 7,18-di-benzyl ethers by NMR respectively, an oil.

EXAMPLE 30

Mycalamide B 7,18, N-Tribenzyl Ether

Mycalamide B 7,18,N-Tribenzyl Ether has a molecular weight of 787 and a molecular formula of C$_{46}$H$_{61}$NO$_{10}$. Its molecular structure is as follows:

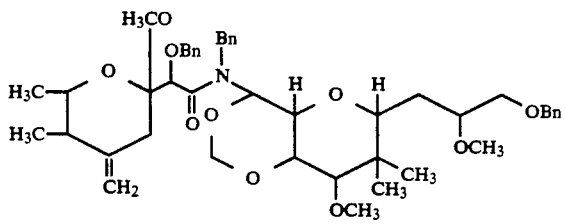

The compound is characterized as follows:
DCIMS (NH₃): 805 (17%, M+NH₄+), 775 (22%), 774 (49%), 773 (100%, M+NH₄+—CH₃OH), 758 (8%), 757 (18%), 756 (35%, MH+—CH₃OH).

$^1$H NMR (CDCl₃): δ 7.4–7.25 (3xφ, m), 6.10 (H10, d, 7.8), 5.15 (10-OCH₂, d, 6.2), 5.07 (N-CH₂φ, d, 17.3), 4.89 (10-OCH₂, d, 6.2), 4.77 (4=CH₂, m), 4.66 (4=CH₂, m), 4.65 (N-CH₂φ, d, 16.8), 4.59 (18-OCH₂φ, d, 12.0), 4.53 (18-OCH₂φ, d, 12.0), 4.37 (7-OCH₂φ, d, 11.6), 4.25 (H12, m), 4.23 (H7, s), 4.07 (H11, broad t, 6.8), 3.93 (7-OCH₂φ, d, 11.5), 3.85 (H2, m), 3.71 (H18, dd, 1.7, 10.0), 3.61 (H18, dd, 3.2, 10.9), 3.51 (13-OCH₃, s), 3.50 (H15, m), 3.47 (H17, m), 3.31 (H13, d, 10.4), 3.30 (17-OCH₃, s), 2.89 (6-OCH₃, s), 2.86 (H5(ax), broad d, 14.7), 2.28 (H5(eq), d, 14.5), 2.15 (H3, m), 1.85 (H16, m), 1.65 (H16, m), 1.14 (2-CH₃, d, 7.0), 0.98 (3-CH₃, d, 7.0), 0.98 (14-CH₃(eq), s), 0.85 (14-CH₃(ax), s) ppm (couplings in Hz).

$^{13}$C NMR (CDCl₃): δ 171.63 (C8), 146.97 (C4), 139.01, 138.30, 138.17, 128.63, 128.28, 128.14, 127.88, 127.51, 127.26 and 126.67 (7—O—, 18—O—and N-CH₂φ), 109.65 (4=CH₂), 101.44 (C6), 86.04 (10-OCH₂), 80.69 (C13), 79.60 (C10), 77.19 (C17), 76.33 (C15), 75.98 (C7), 73.42 (C12), 73.30 (18-OCH₂), 71.91 (7-OCH₂), 69.45 (C2), 69.05 (C18), 67.67 (C11), 61.39 (13-OCH₃), 56.44 (17-OCH₃), 47.81 (6-OCH₃), 46.32 (N-CH₂), 41.53 (C3), 40.46 (C14), 33.46 (C5), 30.66 (C16), 24.11 (14-CH₃(eq)), 17.76 (2-CH₃), 14.84 (14-CH₃(ax)), 12.18 (3-CH₃).

Mycalamide B 7,18,N-tribenzyl ether can be prepared as follows: Mycalamide B (7 mg), powdered KOH (22 mg), and benzyl bromide (36 mg) were stirred in DMSO (0.3 ml) at room temperature for 3 hours. H₂O (2 ml) was added and the mixture transferred onto a reverse phase pipette column (200 mg C18, equilibrated to H₂O), flushed with H₂O (8 ml), then eluted with MeOH (6 ml). The resulting MeOH fraction was evaporated to dryness, then subjected to prep TLC (5:2 PE:EtOAc). Two bands of silica (R_f 0.6, 0.7) were recovered and each eluted with ethyl acetate to give two pure products (2.2 mg, 5.2 mg), which were mycalamide B 7,8,18-tri and 7,18,N-tri- benzyl ethers by NMR respectively, an oil.

EXAMPLE 31

Mycalamide B 7,8,18-Tribenzyl Ether

Mycalamide B 7,8,18-Tribenzyl Ether has a molecular weight of 787 and a molecular formula of C₄₆H₆₁NO₁₀. Its molecular structure is as follows:

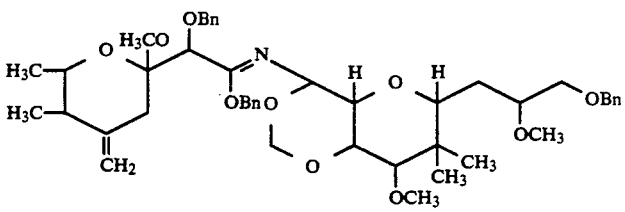

The compound is characterized as follows:
DCIMS (NH₃): 789 (60%), 788 (100%, MH+).

$^1$H NMR (CDCl₃): δ 7.4–7.2 (φ, m), 5.28 (8-OCH₂φ, d, 12.5), 5.13 (10-OCH₂, d, 6.1), 5.09 (8-OCH₂φ, d, 12.6), 5.00 (H10, d, 2.0), 4.76 (4=CH₂, t, 2.0), 4.69 (4=CH₂, t, 2.0), 4.68 (10-OCH₂, d, 6.1), 4.67 (H7, s), 4.60 (18-OCH₂φ, d, 12.2), 4.51 (7-OCH₂φ, d, 12.1), 4.47 (18-OCH₂φ, d, 12.2), 4.39 (7-OCH₂φ, d, 12.1), 3.97 (H12, dd, 1.8, 3.2), 3.76 (H2, dq, 2.6, 6.4), 3.63 (H18, dd, 2.7, 10.4), 3.52 (H18, dd, 4.3, 10.6), 3.51 (H11, t, 1.9), 3.51 (H15, dd, 2.5, 12.5), 3.39 (H17, m), 3.36 (13-OCH₃, s), 3.34 (17-OCH₃, s), 3.13 (6-OCH₃, s), 3.09 (H5(ax), td, 2.0, 14.7), 2.86 (H13, d, 3.2), 2.34 (H5(eq), d, 14.8), 2.31 (H16, m), 2.12 (H3, dq, 2.4, 7.1), 1.71 (H16, m), 1.20 (14-CH₃(ax), s), 1.02 (2-CH₃, d, 6.5), 0.91 (14-CH₃(eq), s), 0.84 (3-CH₃, d, 7.0) ppm (couplings in Hz).

$^{13}$C NMR (CDCl₃): δ 147.53 (C4), 128.41, 128.34, 128.25, 128.01, 127.87, 127.69, 127.56 and 127.31 (7-, 8- and 18-OCH₂φ), 109.11 (4=CH₂), 101.32 (C6), 86.40 (10-OCH₂), 84.03 (C13), 82.56 (C10), 78.65 (C15), 78.30 (C17), 73.32 and 73.29 (18-OCH₂ and C7), 71.71 (7-OCH₂), 69.77 (C18), 69.09 (C2), 68.70 (C12), 67.43 (8-OCH₂), 64.79 (C11), 59.32 (13-OCH₃), 56.98 (17-OCH₃), 48.24 (6-OCH₃), 41.59 (C3), 36.66 (C14), 33.83 (C5), 28.46 (C16), 27.68 (14-CH₃(ax)), 22.25 (14-CH₃(eq)), 17.67 (2-CH₃), 11.73 (3-CH₃). NB: 3xφ, C8 not observed.

Mycalamide B 7,8,18-tribenzyl ether can be prepared as follows: Mycalamide B (7 mg), powdered KOH (22 mg), and benzyl bromide (36 mg) were stirred in DMSO (0.3 ml) at room temperature for 3 hours. H₂O (2 ml) was added and the mixture transferred onto a reverse phase pipette column (200 mg C18, equilibrated to H₂O), flushed with H₂O (8 ml), then eluted with MeOH (6 ml). The resulting MeOH fraction was evaporated to dryness, then subjected to prep TLC (5:2 PE:EtOAc). Two bands of silica (R_f 0.6, 0.7) were recovered and each eluted with ethyl acetate to give two pure products (2.2 mg, 5.2 mg), which were mycalamide B 7,8,18-tri- and 7,18,N-tri- benzyl ethers by NMR respectively, an oil.

EXAMPLE 32

Mycalamide B Bis-TBDMS Ether

Mycalamide B Bis-TBDMS Ether has a molecular weight of 745 and a molecular formula of C₃₇H₇₁NO₁₀Si₂. Its molecular structure is as follows:

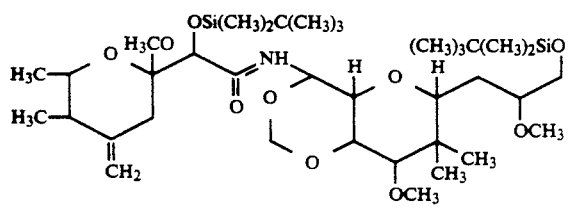

The compound is characterized as follows:

$^1$H NMR (CDCl$_3$): δ 7.27 (NH9, d, 9.9), 5.76 (H10, dd, 8.8, 9.8), 5.10 (10-OCH$_2$, d, 7.0), 4.82 (10-OCH$_2$, d, 7.0), 4.81 (4=CH$_2$, t, 2.0), 4.71 (4=CH$_2$, t, 2.0), 4.22 (H7, s), 4.14 (H12, dd, 6.2, 9.2), 3.87 (H2, dq, 2.8, 6.5), 3.74 (H11, dd, 6.1, 8.7), 3.70 (H18, dd, 2.8, 11.5), 3.57 (H18, dd, 3.7, 11.6), 3.52 (13-OCH$_3$, s), 3.38 (H13, d, 9.3), 3.35 (H15, dd, 2.0, 9.6), 3.29 (6-OCH$_3$, s), 3.26 (17-OCH$_3$, s), 3.16 (H17, m), 2.51 (H5(eq), d, 14.4), 2.36 (H5(ax), td, 2.0, 14.6), 2.19 (H3, dq, 2.9, 7.1), 1.79 (H16, ddd, 2.0, 9.8, 14.2), 1.55 (H16, m), 1.17 (2-CH$_3$, d, 6.6), 1.00 (14-CH$_3$(eq), s), 0.99 (3-CH$_3$, d, 7.0), 0.94 (7-OSiC(CH$_3$)$_3$, s), 0.88 (18-OSiC(CH$_3$)$_3$, s), 0.87 (14-CH$_3$(ax), s), 0.16 and 0.14 (7-OSi(CH$_3$)$_2$, 2xs), 0.06 (18-OSi(CH$_3$)$_2$, s) ppm (couplings in Hz).

$^{13}$C NMR (CDCl$_3$): δ 170.69 (C8), 146.62 (C4), 109.97 (4=CH$_2$), 99.59 (C6), 86.34 (10-OCH$_2$), 80.07 (C13), 78.87 (C17), 77.2 (C7), 76.31 (C15), 73.92 (C12), 73.38 (C10), 70.1 (C11, broad), 69.56 (C2), 62.03 (C18), 61.51 (13-OCH$_3$), 56.69 (17-OCH$_3$), 50.00 (6-OCH$_3$), 41.32 (C3), 41.04 (C14), 35.59 (C5), 29.70 (C16), 25.97 (7-OSiC(CH$_3$)$_3$), 25.87 (18-OSiC(CH$_3$)$_3$), 23.89 (14-CH$_3$(eq)), 17.85 (2-CH$_3$), 14.3 (14-CH$_3$(ax), broad), 11.85 (3-CH$_3$), −4.74 (7-OSi(CH$_3$)$_2$), −5.26 (18-OSi(CH$_3$)$_2$).

Mycalamide B bis-TBDMS ether can be prepared as follows: Mycalamide B (1 mg), t-butyldimethylchlorosilane (12 mg), dimethylaminopyridine (1 mg), and triethylamine (14 mg) were stirred in pyridine (0.2 ml) at 70° C. for 20 hours. H$_2$O (0.5 ml) was added, the mixture extracted with CH$_2$Cl$_2$ (3×0.3 ml), and the solvent removed. The combined organic extract was subjected to silica gel chromatography (200 mg Davisil, 150 Å, 35–70 μm), developed in steps from hexane to ethanol/ethyl acetate. The major fraction (1 mg) eluted with 3:1 PE:EtOAc was pure mycalamide bis-TBDMS ether by PMR, an oil.

EXAMPLE 33

Mycalamide A 7,N-Dibenzyl Ether

Mycalamide A 7,N-Dibenzyl Ether has a molecular weight of 683 and a molecular formula of C$_{38}$H$_{53}$NO$_{10}$. Its molecular structure is as follows:

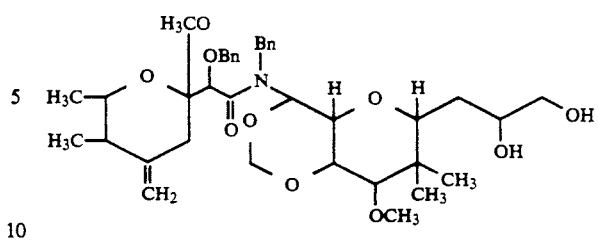

The compound is characterized as follows:

DCIMS (NH$_3$): 701 (12%, M+NH$_4^+$), 672 (17%), 671 (46%), 670 (44%), 669 (100%, M+NH$_4^+$—CH$_3$OH), 654 (19%), 653 (20%), 652 (45%, MH$^+$—CH$_3$OH).

$^1$H NMR (CDCl$_3$): δ 7.7–7.25 (2xφ, m), 6.40 (H10, d, 9.2), 5.21 (10-OCH$_2$, d, 7.0), 5.14 (N-CH$_2$φ, d, 17.0), 4.90 (10-OCH$_2$, d, 6.9), 4.78 (4=CH$_2$, t, 1.9), 4.69 (4=CH$_2$, t, 1.8), 4.63 (N-CH$_2$φ, d, 17.1), 4.33 (7-OCH$_2$φ, d, 12.0), 4.24 (H7, s), 4.24 (H12, dd, 7.0, 9.2), 4.00 (H11, dd, 7.0, 9.2), 3.91 (H2, dq, 2.9, 6.5), 3.86 (7-OCH$_2$φ, d, 12.5), 3.8 (H17, m), 3.78 (H15, m), 3.69 (H18, dd, 2.8, 11.1), 3.56 (13-OCH$_3$, s), 3.48 (H13, d, 10.0), 3.29 (H18, dd, 6.5, 11.0), 2.96 (6-OCH$_3$, s), 2.64 (H5(ax), broad d, 14.4), 2.28 (H5(eq), d, 14.1), 2.19 (H3, dq, 2.5, 7.0), 1.55 (H$_2$16, m), 1.19 (2-CH$_3$, d, 6.5), 1.01 (3-CH$_3$, d, 7.0), 1.00 (14-CH$_3$(eq), s), 0.87 (14-CH$_3$(ax), s) ppm (couplings in Hz).

Mycalamide A 7,N-dibenzyl ether can be prepared as follows: Mycalamide A (5 mg), powdered KOH (8 mg) and benzyl bromide (15 mg) were stirred in DMSO at room temperature for 3 minutes. H$_2$O (2 ml) was added and the mixture extracted with CH$_2$Cl$_2$ (2×2 ml). This extract was washed with H$_2$O (2×2 ml) and the solvent removed (7.5 mg). Prep RPLC (15% H$_2$O in MeOH) gave four fractions (1 mg, 0.7 mg, 2.5 mg, 2 mg), but the third fraction was a mixture of the second and another component. Prep TLC (developed in 1:1 PE:EtOAc) and appropriate combination of samples gave four pure products (1 mg, 1.3 mg, 1 mg, 2 mg) which were mycalamide A 7-mono-; 7,18-di-; 7,N-di- and 7,18,N-tribenzyl ethers by NMR respectively, an oil.

EXAMPLE 34

Mycalamide A 7,18-Dibenzyl Ether

Mycalamide A 7,18-Dibenzyl Ether has a molecular weight of 683 and a molecular formula of C$_{38}$H$_{53}$NO$_{10}$. Its molecular structure is as follows:

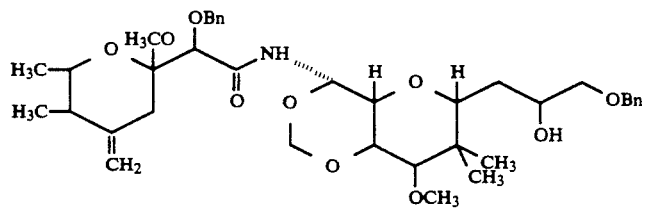

The compound is characterized as follows:

DCIMS (NH$_3$): 703 (7%), 702 (12%), 701 (28%, M+NH$_4^+$), 672 (9%), 671 (27%), 670 (41%), 669 (100%, M+NH$_4^+$—CH$_3$OH), 654 (5%), 653 (8%), 652 (19%, MH$^+$—CH$_3$OH).

$^1$H NMR (CDCl$_3$): δ 7.4–7.25 (2xφ, m), 7.22 (NH9, d, 10.0), 5.92 (H10, t, 10.0), 5.13 (10-OCH$_2$, d, 7.1), 4.82 (10-OCH$_2$, d, 7.0), 4.80 (4=CH$_2$, m), 4.75 (7-OCH$_2$φ, d, 11.2), 4.70 (4=CH$_2$, m), 4.63 (7-OCH$_2$φ, d, 10.8), 4.59 (18-OCH$_2$φ, d, 11.7), 4.52 (18-OCH$_2$φ, d, 12.1), 4.22 (H12, dd, 6.8, 10.5), 4.08 (H7, s), 3.92 (H17, m), 3.86 (H2, dq, 2.9, 6.6), 3.81 (H11, dd, 6.7, 10.1), 3.60 (H15, dd, 1.8, 10.4), 3.55 (13-OCH$_3$, s), 3.46 (H13, d, 10.3), 3.44 (H18, dd, 4.7, 9.6), 3.39 (H18, dd, 5.6, 9.6), 3.10 (6-OCH$_3$, s), 2.47 (H5(ax), broad d, 14.5), 2.40 (H5(eq), d, 14.4), 2.18 (H3, dq, 2.9, 7.1), 1.7 (H16, m), 1.55 (H16, m), 1.16 (2-CH$_3$, d, 6.6), 0.97 (14-CH$_3$(eq), s), 0.95 (3-CH$_3$, d, 7.0), 0.88 (14-CH$_3$(ax), s) ppm (couplings in Hz).

$^{13}$C NMR (CDCl$_3$): δ 170.43 (C8), 146.62 (C4), 138.86, 137.15, 128.46, 128.41, 128.34, 128.07, 127.64 and 127.53 (7- and 18-OCH$_2$φ), 109.77 (4=CH$_2$), 100.03 (C6), 86.76 (10-OCH$_2$), 80.91 (C7), 79.23 (C13), 79.13 (C15), 74.48 (C12), 74.07 (C10), 73.78 (C18), 73.20 and 73.11 (7- and 18-OCH$_2$), 71.29 (C11), 70.09 (C17), 69.29 (C2), 61.84 (13-OCH$_3$), 49.15 (6-OCH$_3$), 41.78 (C14), 41.41 (C3), 34.65 (C5), 32.58 (C16), 23.05 (14-CH$_3$(eq)), 17.80 (2-CH$_3$), 13.41 (14-CH$_3$(ax)), 11.74 (3-CH$_3$).

Mycalamide A 7,18-dibenzyl ether can be prepared as follows: Mycalamide A (5 mg), powdered KOH (8 mg) and benzyl bromide (15 mg) were stirred in DMSO at room temperature for 3 minutes. H$_2$O (2 ml) was added and the mixture extracted with CH$_2$Cl$_2$ (2×2 ml). This extract was washed with H$_2$O (2×2 ml) and the solvent removed (7.5 mg). Prep RPLC (15% H$_2$O in MeOH) gave four fractions (1 mg, 0.7 mg, 2.5 mg, 2 mg), but the third fraction was a mixture of the second and another component. Prep TLC (developed in 1:1 PE:EtOAc) and appropriate combination of samples gave four pure products (1 mg, 1.3 mg, 1 mg, 2 mg) which were mycalamide A 7-mono-; 7,18-di-; 7,N-di- and 7,18,N-tribenzyl ethers by NMR respectively, an oil.

EXAMPLE 35

Mycalamide A 7-Monobenzyl Ether

Mycalamide A 7-Monobenzyl Ether has a molecular weight of 593 and a molecular formula of C$_{31}$H$_{47}$NO$_{10}$. Its molecular structure is as follows:

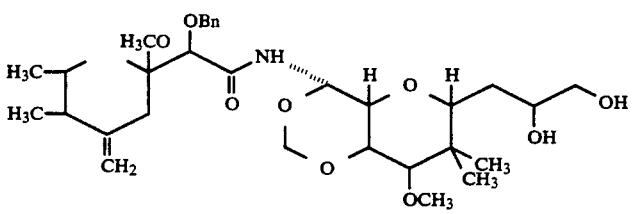

The compound is characterized as follows:
DCIMS (NH$_3$): 611 (7%, M+NH$_4$$^+$), 582 (8%), 581 (26%), 580 (34%), 579 (100%, M+NH$_4$$^+$—CH$_3$OH), 564 (5%), 563 (6%), 562 (17%, MH$^+$—CH$_3$OH).

$^1$H NMR (CDCl$_3$): δ 7.4–7.25 (φ, m), 7.24 (NH9, d, 10.0), 5.93 (H10, t, 10.1), 5.13 (10-OCH$_2$, d, 7.0), 4.84 (10-OCH$_2$, d, 7.0), 4.82 (4=CH$_2$, t, 1.8), 4.77 (7-OCH$_2$φ, d, 11.2), 4.72 (4=CH$_2$, t, 1.9), 4.68 (7-OCH$_2$φ, d, 11.2), 4.23 (H12, dd, 6.8, 10.5), 4.10 (H7, s), 3.88 (H2, dq, 2.7, 6.6), 3.82 (H17, m), 3.80 (H11, dd, 6.8, 10.0), 3.68 (H15, dd, 5.8, 6.9), 3.62 (H18, dd, 3.5, 11.3), 3.56 (13-OCH$_3$, s), 3.49 (H13, d, 10.5), 3.39 (H18, dd, 6.0, 11.2), 3.14 (6-OCH$_3$, s), 2.48 (H5(ax), td, 1.9, 14.4), 2.41 (H5(eq), d, 14.3), 2.19 (H3, dq, 2.5, 7.0), 1.55 (H$_2$16, m), 1.17 (2-CH$_3$, d, 6.6), 0.98 (14-CH$_3$(eq), s), 0.97 (3-CH$_3$, d, 7.0), 0.88 (14-CH$_3$(ax), s) ppm (couplings in Hz).

$^{13}$C NMR (CDCl$_3$): δ 170.59 (C8), 146.48 (C4), 128.55, 128.38 and 128.19 (7-OCH$_2$φ), 109.91 (4=CH$_2$), 100.09 (C6), 86.86 (10-OCH$_2$), 80.81 (C7), 79.24 (C13), 78.98 (C15), 74.56 (C12), 74.19 (C10), 73.24 (7-OCH$_2$), 71.70 (C17), 71.66 (C11), 69.38 (C2), 66.74 (C18), 61.88 (13-OCH$_3$), 49.22 (6-OCH$_3$), 41.82 (C14), 41.38 (C3), 34.61 (C5), 32.02 (C16), 22.98 (14-CH$_3$(eq)), 17.80 (2-CH$_3$), 13.26 (14-CH$_3$(ax)), 11.76 (3-CH$_3$). NB: 1×φ not observed.

Mycalamide A 7-monobenzyl ether can be prepared as follows: Mycalamide A (5 mg), powdered KOH (8 mg) and benzyl bromide (15 mg) were stirred in DMSO at room temperature for 3 minutes. H$_2$O (2 ml) was added and the mixture extracted with CH$_2$Cl$_2$ (2×2 ml). This extract was washed with H$_2$O (2×2 ml) and the solvent removed (7.5 mg). Prep RPLC (15% H$_2$O in MeOH) gave four fractions (1 mg, 0.7 mg, 2.5 mg, 2 mg), but the third fraction was a mixture of the second and another component. Prep TLC (developed in 1:1 PE:EtOAc) and appropriate combination of samples gave four pure products (1 mg, 1.3 mg, 1 mg, 2 mg) which were mycalamide A 7-mono-; 7,18-di-; 7,N-di- and 7,18,N-tri-benzyl ethers by NMR respectively, an oil.

EXAMPLE 36

Mycalamide A 7,18,N-Tribenzyl Ether

Mycalamide A 7,18,N-Tribenzyl Ether has a molecular weight of 773 and a molecular formula of C$_{45}$H$_{59}$NO$_{10}$. Its molecular structure is as follows:

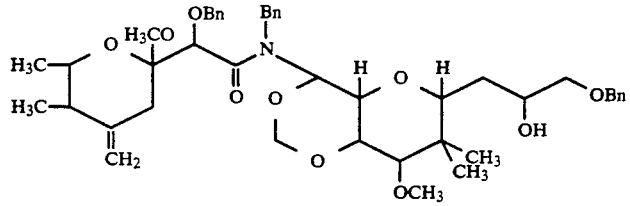

The compound is characterized as follows:
DCIMS (NH$_3$): 791 (8%, M+NH$_4$$^+$), 761 (19%), 760 (49%), 759 (100%, M+NH$_4$$^+$—CH$_3$OH), 743 (13%), 742 (24%, MH$^+$—CH$_3$OH).

$^1$H NMR (CDCl$_3$): δ 7.4–7.25 (3×φ, m), 6.33 (H10, d, 9.1), 5.19 (10-OCH$_2$, d, 6.0), 5.11 (N-CH$_2$φ, d, 17.1), 4.91 (10-OCH$_2$, d, 6.0), 4.76 (4=CH$_2$, t, 1.9), 4.66 (4=CH$_2$, m), 4.65 (N-CH$_2$φ, d, 17.2), 4.56 (18-OCH$_2$φ, d, 12.4), 4.52 (18-OCH$_2$φ, d, 12.0), 4.36 (7-OCH$_2$φ, d, 11.5), 4.27 (H7, s), 4.24 (H12, dd, 6.9, 10.0), 4.03 (H11, dd, 7.1, 8.7), 3.92 (H17, m), 3.90 (7-OCH$_2\phi$, d, 11.5), 3.88 (H2, dq, 2.7, 6.5), 3.77 (H15, m), 3.55 (13-OCH$_3$, s), 3.47 (H13, d, 10.0), 3.44 (H18, m), 3.36 (H18, dd, 5.1, 9.1), 2.90 (6-OCH$_3$, s), 2.86 (H5(ax), broad d, 14.0), 2.33 (H5(eq), d, 14.0), 2.16 (H3, dq, 2.7, 7.0), 1.83 (H16, broad d, 14.0), 1.5 (H16, m), 1.16 (2-CH$_3$, d, 6.5), 1.01 (3-CH$_3$, d, 7.0), 1.00 (14-CH$_3$(eq), s), 0.87 (14-CH$_3$(ax), s) ppm (couplings in Hz).

$^{13}$C NMR (CDCl$_3$): δ 138.45, 128.68, 128.32, 128.15, 127.70, 127.60, 127.48, 127.35 and 126.95 (3x$\phi$), 109.52 (4=CH$_2$), 86.23 (10-OCH$_2$), 79.84 (C13), 78.68 (C15), 77.80 (C10), 76.22 (C7), 74.35 (C12), 74.16 (18-OCH$_2$), 73.32 (7-OCH$_2$), 71.79 (C18), 69.28 (C17), 69.11 (C2), 68.44 (C11), 61.67 (13-OCH$_3$), 47.92 (6-OCH$_3$), 45.96 (N-CH$_2$), 41.48 (C3), 34.29 (C5), 33.60 (C16), 23.32 (14-CH$_3$(eq)), 17.70 (2-CH$_3$), 13.70 (14-CH$_3$(ax)), 12.46 (3-CH$_3$). NB: C4, C6, C8 and C14 not observed.

Mycalamide A 7,18,N-tribenzyl ether can be prepared as follows: Mycalamide A (5 mg), powdered KOH (8 mg) and benzyl bromide (15 mg) were stirred in DMSO at room temperature for 3 minutes. H$_2$O (2 ml) was added and the mixture extracted with CH$_2$Cl$_2$ (2×2 ml). This extract was washed with H$_2$O (2×2 ml) and the solvent removed (7.5 mg). Prep RPLC (15% H$_2$O in MeOH) gave four fractions (1 mg, 0.7 mg, 2.5 mg, 2 mg), but the third fraction was a mixture of the second and another component. Prep TLC (developed in 1:1 PE:EtOAc) and appropriate combination of samples gave four pure products (1 mg, 1.3 mg, 1 mg, 2 mg) which were mycalamide A 7-mono-; 7,18-di-; 7,N-di- and 7,18,N-tri-benzyl ethers by NMR respectively, an oil.

EXAMPLE 37

7'-Deutero, 7'-Methoxy, N-Methyl Mycalamide A

7'-Deutero, 7'-Methoxy, N-Methyl Mycalamide A has a molecular weight of 532 and a molecular formula of C$_{26}$H$_{44}$DNO$_{10}$. Its molecular structure is as follows:

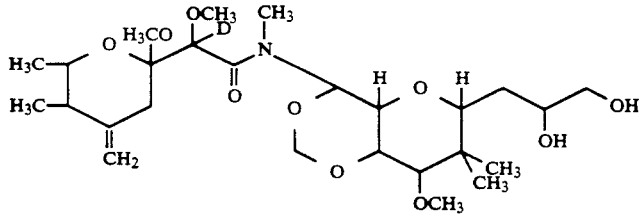

The compound is characterized as follows:
DCIMS (NH$_3$): 550 (3%, M+NH$_4^+$), 520 (10%), 518 (61%, M+NH$_4^+$—CH$_3$OH), 503 (23%), 502 (9%), 501 (100%, MH$^+$—CH$_3$OH).

$^1$H NMR (CDCl$_3$): δ 6.40 (H10, d, 10.3), 5.15 (10-OCH$_2$, d, 6.7), 4.86 (10-OCH$_2$, d, 6.8), 4.84 (4=CH$_2$, t, 2.0), 4.74 (4=CH$_2$, t, 2.0), 4.27 (H12, dd, 7.0, 10.7), 4.14 (H11, dd, 7.0, 10.4), 3.94 (H2, dq, 2.7, 6.5), 3.67 (H17, m), 3.66 (H18, m), 3.64 (H15, dd, 1.5, 9.8), 3.58 and 3.56 (7- and 13-OCH$_3$, 2xs), 3.53 (H13, d, 10.7), 3.31 (6-OCH$_3$, s), 3.26 (H18, dd, 6.9, 11.0), 3.14 (N-CH$_3$, s), 2.84 (H5(ax), td, 2.0, 14.6), 2.51 (H5(eq), d, 14.5), 2.21 (H3, dq, 2.6, 6.8), 1.53 (H$_2$16, m), 1.13 (2-CH$_3$, d, 6.6), 1.03 (3-CH$_3$, d, 7.0), 0.96 (14-CH$_3$(eq), s), 0.87 (14-CH$_3$(ax), s) ppm (couplings in Hz).

7'-deutero, 7'-methoxy, N-methyl mycalamide A can be prepared as follows: 7-methoxy, N-methyl mycalamide A (1.2 mg) (see Example 12) was dissolved in 3M NaOCD$_3$/CH$_3$OD and stirred at 70° C. for 2 days. The crude mixture was then loaded onto a TLC plate (silica gel 60 F$_{254, 0.2}$ mm) which was developed twice in 1:19 EtOH:EtOAc. The two bands of silica were recovered and each eluted with 1:3 EtOH:EtOAc giving two fractions (0.4 mg, 0.7 mg) where the first was a mixture but the second was pure 7'-methoxy, N-methyl mycalamide A with quantitative inclusion of deuterium at the epimerised C7 centre by PMR and MS, an oil.

EXAMPLE 38

7-Epimycalamide A Trans-Oxazolidinone 7-epimycalamide A trans-oxazolidinone has a molecular weight of 473 and a molecular formula of C$_{23}$H$_{39}$NO$_9$. Its molecular structure is as follows:

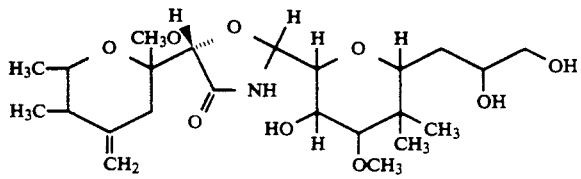

The compound is characterized as follows:
HRFABMS: 442.24300 (MH$_+$—CH$_3$OH, −2.4 ppm).
FABMS: 443 (28%), 442 (100%, MH$_+$—CH$_3$OH).

$^1$H NMR (CDCl$_3$): δ 6.67 (NH9, broad s), 5.67 (H10, dd, 2.2, 8.6), 4.83 (4=CH$_2$, t, 2.)), 4.71 (4=CH$_2$, t, 2.1), 4.28 (H7, d, 2.1), 3.97 (H12, dd, 6.9, 9.7), 3.94 (H2, dq, 2.4, 6.6), 3.86 (H17, m), 3.84 (H11, dd, 6.9, 8.7), 3.62 (H15, m), 3.60 (13-OCH$_3$, s), 3.58 (H18, m), 3.52 (H18, m), 3.43 (6-OCH$_3$, s), 2.95 (H13, d, 9.7), 2.92 (H5(ax), td, 2.0, 14.4), 2.20 (H3, dq, 2.4, 6.9), 2.13 (H5(eq), d, 14.3), 1.53 (H$_2$16, m), 1.17 (2-CH$_3$, d, 6.5), 1.02 (3-CH$_3$, d, 7.0), 0.97 (14-CH$_3$(eq), s), 0.88 (14-CH$_3$(ax), s) ppm (couplings in Hz).

7-epimycalamide A trans-oxazolidinone was prepared as follows: Mycalamide A (7 mg) was stirred in a solution of 2M NaOH in 50% MeOH-H$_2$O (0.3 ml) at 55° C. for 10 hours. The solution was concentrated (0.1 ml) and then loaded onto a C18 pipette column (100 mg). The column was flushed with H$_2$O (8 ml), then a fraction obtained by elution with MeOH (5 ml) was collected and the solvent removed (6 mg). Analytical reverse phase HPLC (45% H$_2$O in MeOH) gave four fractions (1.4 mg, 1.8 mg, 0.7 mg, 0.8 mg). PMR and NOE's showed that the first two were cis and trans isomers respectively at C7–C10 of mycalamide A oxazolidinone, but the second two were at least 70% pure trans and cis isomers, respectively, of 7-epimycalamide A oxazolidinone, with the major impurity being unreacted mycalamide A by PMR and HRFABMS, an oil.

EXAMPLE 39

7-Epimycalamide A Cis-Oxazolidinone

7-Epimycalamide A Cis-Oxazolidinone has a molecular weight of 473 and a molecular formula of $C_{23}H_{39}NO_9$. Its molecular structure is as follows:

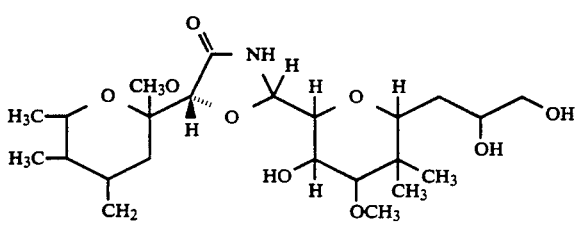

The compound is characterized as follows:
HRFABMS: 442.24100 (MH+—CH$_3$OH, −6.9 ppm).
FABMS: 443 (26%), 442 (100%, MH+—CH$_3$OH).
$^1$H NMR (CDCl$_3$): δ 8.04 (NH9, broad s), 5.66 (H10, dd, 1.4, 6.9), 4.82 (4=CH$_2$, t, 2.1), 4.70 (4=CH$_2$, t, 2.0), 4.33 (H7, d, 1.3), 4.06 (H11, t, 6.3), 4.01 (H12, dd, 6.1, 8.3), 3.95 (H2, dq, 2.6, 6.6), 3.88 (H17, m), 3.59 (13-OCH$_3$, s), 3.57 (H$_2$18, m), 3.47 (H15, broad d, 9.5), 3.36 (6-OCH$_3$, s), 3.05 (H5(ax), td, 2.1, 14.3), 3.04 (H13, d, 8.1), 2.19 (H3, dq, 2.3, 6.7), 2.11 (H5(eq), d, 14.2), 1.60 and 1.54 (H$_2$16, m), 1.15 (2-CH$_3$, d, 6.5), 0.99 (3-CH$_3$, d, 6.7), 0.98 (14-CH$_3$(eq), s), 0.86 (14-CH$_3$(ax), s) ppm (couplings in Hz).

7-epimycalamide A cis-oxazolidinone can be prepared as follows: Mycalamide A (7 mg) was stirred in a solution of 2M NaOH in 50% MeOH-H$_2$O (0.3 ml) at 55° C. for 10 hours. The solution was concentrated (0.1 ml) and then loaded onto a C18 pipette column (100 mg). The column was flushed with H$_2$O (8 ml), then a fraction obtained by elution with MeOH (5 ml) was collected and the solvent removed (6 mg). Analytical reverse phase HPLC (45% H$_2$O in MeOH) gave four fractions (1.4 mg, 1.8 mg, 0.7 mg, 0.8 mg). PMR and NOE's showed that the first two were cis and trans isomers respectively at C7-C10 of mycalamide A oxazolidinone, but the second two were at least 70% pure trans and cis isomers, respectively, of 7-epimycalamide A oxazolidinone, with the major impurity being unreacted mycalamide A by PMR and HRFABMS, an oil.

EXAMPLE 40

Neomycalamide A Triacetate

Neomycalamide A Triacetate has a molecular weight of 597 and a molecular formula of $C_{29}H_{43}NO_{12}$. Its molecular structure is as follows:

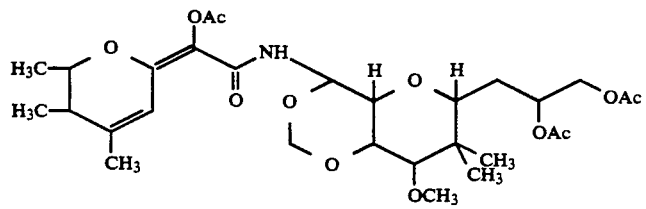

The compound is characterized as follows:
DCIMS (NH$_3$): 616 (7%), 615 (34%, M+NH$_4^+$), 600 (13%), 599 (31%), 598 (100%, MH+), 573 (28%), 571 (18%), 557 (24%), 556 (66%, MH+—CH$_2$CO), 493 (8%), 419 (35%).
$^1$H NMR (CDCl$_3$): δ 8.11 (NH9, d, 9.0), 6.02 (H5, q, 1.4), 5.86 (H10, t, 9.2), 5.15 (10-OCH$_2$, d, 7.0), 5.11 (H17, m), 4.86 (10-OCH$_2$, d, 7.0), 4.32 (H2, dq, 2.9, 6.5), 4.28 (H18, dd, 2.7, 12.6), 4.21 (H12, dd, 6.3, 10.4), 4.10 (H18, dd, 5.5, 12.8), 3.88 (H11, dd, 6.2, 9.7), 3.56 (13-OCH$_3$, s), 3.47 (H15, m), 3.40 (H13, d, 10.1), 2.25 (H3, m), 2.25 (7-OCOCH$_3$, s), 2.10 and 2.01 (17- and 18-OCOCH$_3$, 2xs), 1.94 (4-CH$_3$, d, 1.3), 1.6–1.8 (H$_2$16, m), 1.44 (2-CH$_3$, d, 6.5), 1.04 (3-CH$_3$, d, 7.0), 0.97 (14-CH$_3$(eq), s), 0.88 (14-CH$_3$(ax), s) ppm (couplings in Hz).

Neomycalamide A triacetate can be prepared as follows: Mycalamide A triacetate (5 mg) was dissolved in CDCl$_3$ (0.5 ml) and 10 μl TFA added. After 5 days at room temperature (monitored by PMR), the reaction was quenched and worked up by evaporation of the solvent and partition between 1:1 CH$_2$Cl$_2$:H$_2$O (5 mg). Prep HPLC (33% H$_2$O in MeOH) gave three fractions (2.5 mg, 1 mg, 0.8 mg), where the first was a mixture of more polar compounds, the third was unreacted mycalamide A triacetate, but the second was about 80% pure neomycalamide A triacetate by PMR, an oil.

EXAMPLE 41

Mycalamide A Tri-p-Bromobenzoate

Mycalamide A Tri-p-Bromobenzoate has a molecular weight of 1052 and a molecular formula of $C_{45}H_{50}Br_3NO_{13}$. Its molecular structure is as follows:

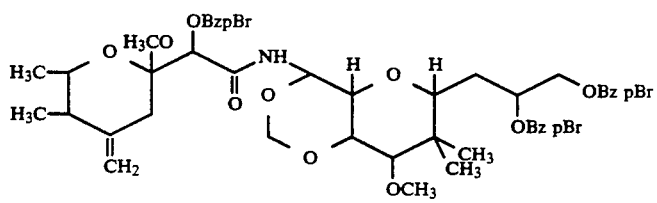

The compound is characterized as follows:
$^1$H NMR (CDCl$_3$): δ 7.97 and 7.84 (7-, 17-, and 18-OCOC$_6$H$_4$Br, 2xd, 8.7), 7.59, 7.58 and 7.56 (7-, 17- and 18-OCOC$_6$H$_4$Br, 3xd, 8.8), 7.45 (NH9, d, 9.2), 5.80 (H10, t, 8.6), 5.64 (H7, s), 5.33 (H17, m), 5.10 (10-OCH$_2$, d, 7.0), 4.89 (10-OCH$_2$, d, 7.0), 4.87 (4=CH$_2$, t, 1.8), 4.75 (4=CH$_2$, t, 1.8), 4.61 (H18, dd, 2.6, 12.5), 4.54 (H18, dd, 4.9, 12.6), 4.11 (H12, dd, 5.9, 9.0), 4.03 (H2, dq, 2.8, 6.6), 3.86 (H11, dd, 5.7, 8.0), 3.62 (H15, dd, 1.4, 10.2), 3.51

(13-OCH₃, s), 3.28 (H13, d, 9.2), 3.20 (6-OCH₃, s), 2.58 (H5(ax), td, 1.7, 14.1), 2.51 (H5(eq), d, 14.3), 2.28 (H3, dq, 2.7, 6.9), 2.02 (H16, m), 1.88 (H16, m), 1.23 (2-CH₃, d, 6.6), 1.05 (3-CH₃, d, 7.1), 1.03 (14-CH₃(eq), s), 0.88 (14-CH₃(ax), s) ppm (couplings in Hz).

Mycalamide A tri-p-bromobenzoate can be prepared as follows: Mycalamide A (5.0 mg, 0.01 mmole), p-bromobenzoyl chloride (11 mg, 0.05 mmole), dimethylaminopyridine (1 mg) and triethylamine (7 mg, 0.07 mmole) were stirred in pyridine (0.4 ml) at 75° C. overnight. H₂O (0.3 ml) was added, the mixture extracted with CH₂Cl₂ (3×0.4 ml), and the solvent removed (17 mg ca.). Prep RPLC (10% H₂O in MeOH) gave four fractions (2 mg, 1 mg, 1.2 mg, 1.1 mg) which were mycalamide A 18-mono-p-bromobenzoate and mycalamide A 7,18-di-p-bromobenzoate, obtained previously, and two new compounds, identified by PMR as pure mycalamide A 17,18-di-p-bromobenzoate and mycalamide A tri-p-bromobenzoate respectively, a white solid.

EXAMPLE 42

Mycalamide A Cis-Oxazolidinone

Mycalamide A Cis-Oxazolidinone has a molecular weight of 473 and a molecular formula of $C_{23}H_{39}NO_9$. Its molecular structure is as follows:

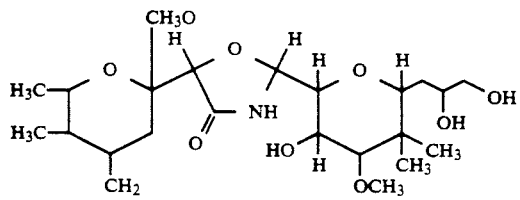

The compound is characterized as follows:
HRFABMS: 496.25270 (M+Na⁺, +0.9 ppm).
DCIMS (NH₃): 491 (5%, M+NH₄⁺), 461 (6%), 460 (30%), 459 (100%, M+NH₄⁺—CH₃OH), 443 (17%), 442 (63%, MH⁺—CH₃OH).
IR (mixed isomers) CHCl₃: 3700-3300, 2910, 1725, 1610, 1380, 1100-1030 cm⁻¹ film 3700-3100, 2950, 1720, 1380, 1150-1030, 870 cm⁻¹.
¹H NMR (CDCl₃): δ 6.58 (NH9, broad s), 5.59 (H10, dd, 1.6, 8.9), 4.83 (4=CH₂, t, 1.9), 4.73 (4=CH₂t, 1.9), 4.39 (H7, d, 1.5), 3.97 (H12, dd, 6.7, 9.8), 3.95 (H2, dq, 2.5, 6.6), 3.94 (H17, m), 3.88 (H11, dd, 6.8, 8.9), 3.61 (13-OCH₃, s), 3.6 (H18, m), 3.6 (H15, m, hidden), 3.56 (H18, dd, 4.1, 11.2), 3.30 (6-OCH₃, s), 2.96 (H13, d, 9.6), 2.40 (H5(ax), td, 2.0, 13.8), 2.28 (H5(eq), d, 13.9), 2.21 (H3, dq, 2.2, 7.0), 1.57 (H16, ddd, 2.5, 10.6, 14.7), 1.51 (H16, m), 1.20 (2-CH₃, d, 6.6), 1.05 (3-CH₃, d, 6.9), 0.98 (14-CH₃(eq), s) 0.89 (14-CH₃(ax), s) ppm (couplings in Hz).
¹H NMR (CD₃OD): δ 5.65 (H10, dd, 1.8, 8.5), 4.80 (4=CH₂, t, 2.0), 4.66 (4=CH₂, t, 2.1), 4.39 (H7, d, 1.7), 3.91 (H2, dq, 3.0, 6.5), 3.9 (H17, m), 3.89 (H12, dd, 6.6, 9.6), 3.73 (H11, dd, 6.6, 8.6), 3.6 (H15, m), 3.59 (H18, dd, 3.8, 11.2), 3.58 (13-OCH₃, s), 3.51 (H18, dd, 4.8, 11.3), 3.27 (6-OCH₃, s), 3.04 (H13, d, 9.5), 2.37 (H5(ax), td, 2.0, 13.8), 2.32 (H5(eq), d, 14.3), 2.19 (H3, dq, 2.7, 7.1), 1.74 (H16, ddd, 1.7, 5.5, 14.4), 1.48 (H16, m), 1.17 (2-CH₃, d, 6.6), 1.02 (3-CH₃, d, 7.0), 0.97 (14-CH₃(eq), s), 0.86 (14-CH₃(ax), s) ppm (couplings in Hz).
¹³C NMR (CDCl₃): δ 170.02 (C8), 146.07 (C4), 110.03 (4=CH₂), 98.82 (C6), 88.02 (C13), 80.83 (C10), 78.58 (C15), 77.58 (C11), 75.68 (C7), 72.04 (C17), 69.31 (C2), 68.89 (C12), 66.74 (C18), 63.09 (13-OCH₃), 48.54 (6-OCH₃), 41.72 (C3), 41.50 (C14), 33.76 (C5), 31.44 (C16), 23.42 (14-CH₃(eq)), 17.87 (2-CH₃), 13.78 (14-CH₃(ax)), 11.70 (3-CH₃).

Mycalamide A cis-oxazolidinone can be prepared as follows: Mycalamide A (3.8 mg) was stirred in a solution of 1M NaOMe in methanol (0.3 ml) at 50° C. for 8 hours. The solvent was removed and the residue extracted with CHCl₃ and filtered (3.3 mg). PMR showed a 1:1 mixture of isomers which were separated by analytical reverse phase HPLC (45% H₂O in MeOH) to give two fractions (0.9 mg, 1.3 mg). PMR and NOE's showed that these were cis and trans isomers respectively at C7-C10 of mycalamide A oxazolidinone, an oil.

EXAMPLE 43

Mycalamide A Trans-Oxazolidinone

Mycalamide A Trans-Oxazolidinone has a molecular weight of 473 and a molecular formula of $C_{23}H_{39}NO_9$. Its molecular structure is as follows:

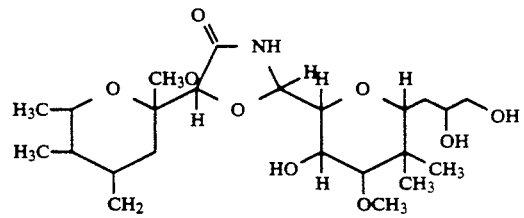

The compound is characterized as follows:
HRFABMS: 496.25390 (M+Na⁺, +3.3 ppm).
DCIMS (NH₃): 461 (6%), 460 (29%), 459 (100%, M+NH₄⁺—CH₃OH), 443 (7%), 442 (41%, MH⁺—CH₃OH).
IR (mixed isomers) CHCl₃: 3700-3300, 2910, 1725, 1610, 1380, 1100-1030 cm⁻¹; film 3700-3100, 2950, 1720, 1380, 1150-1030, 870 cm⁻¹.
¹H NMR (CDCl₃): δ 7.87 (NH9, broad s), 5.62 (H10, dd, 2.3, 5.3), 4.85 (4=CH₂, t, 2.0), 4.74 (4=CH₂, t, 1.9), 4.45 (H7, d, 2.4), 4.00 (H12, dd, 5.6, 7.4), 3.95 (H2, dq, 2.6, 6.5), 3.94 (H11, t, 5.4), 3.92 (H17, m), 3.58 (H₂18, m), 3.56 (13-OCH₃, s), 3.54 (H15, m, hidden), 3.31 (6-OCH₃, s), 2.98 (H13, d, 7.5), 2.48 (H5(ax), td, 1.9, 13.7), 2.32 (H5(eq), d, 13.7), 2.22 (H3, dq, 2.8, 7.0), 1.68 and 1.57 (H₂16, m), 1.19 (2-CH₃, d, 6.6), 1.04 (3-CH₃, d, 6.9), 1.03 (14-CH₃(eq), s), 0.88 (14-CH₃(ax), s) ppm (couplings in Hz).
¹H NMR (CD₃OD): δ 5.51 (H10, dd, 2.6, 3.4), 4.82 (4=CH₂, t, 1.9), 4.67 (4=CH₂, t, 2.0), 4.45 (H7, d, 2.6), 3.92 (H12, dd, 5.1, 6.5), 3.91 (H2, dq, 2.6, 6.5), 3.78 (H17, m), 3.85 (H11, dd, 3.6, 5.0), 3.62 (H15, dd, 2.9, 10.2), 3.54 (H18, dd, 4.3, 11.2), 3.51 (13-OCH₃, s), 3.49 (H18, dd, 4.8, 11.3), 3.28 (6-OCH₃,s), 3.10 (H13, d, 6.6), 2.41 (H5(ax), td, 2.0, 14.1), 2.28 (H5(eq), d, 13.8), 2.21 (H3, dq, 2.6, 7.0), 1.82 and 1.68 (H₂16, m), 1.17 (2-CH₃, d, 6.6), 1.06 (14-CH₃(eq), s), 1.01 (3-CH₃, d, 7.0), 0.87 (14-CH₃(ax), s) ppm (couplings in Hz).
¹³C NMR (CDCl₃): δ 171.63 (C8), 146.37 (C4), 109.75 (4=CH₂), 99.28 (C6), 86.88 (C13), 86.41 (C18), 79.56 (C15), 77.12 (C7), 74.12 (C11), 72.48 (C17), 69.29 (C2), 68.89 (C12), 66.76 (C18), 61.73 (13-OCH₃), 48.81 (6-OCH₃), 41.61 (C3), 39.81 (C14), 33.65 (C5), 31.01 (C16), 24.43 (14-CH₃(eq)), 17.86 (2-CH₃), 16.28 (14-CH₃(ax)), 11.80 (3-CH₃).

Mycalamide A trans-oxazolidinone can be prepared as follows: Mycalamide A (3.8 mg) was stirred in a solution of 1M NaOMe in methanol (0.3 ml) at 50° C. for 8 hours. The solvent was removed and the residue extracted with CHCl3 and filtered (3.3 mg). PMR showed a 1:1 mixture of isomers which were separated by analytical reverse phase HPLC (45% H2O in MeOH) to give two fractions (0.9 mg, 1.3 mg). PMR and NOE's showed that these were cis and trans isomers respectively at C7–C10 of mycalamide A oxazolidinone, an oil.

EXAMPLE 44

Mycalamide A 17,18-Bis-TBDMS Ether

Mycalamide A 17,18-bis-TBDMS ether has a molecular weight of 731 and a molecular formula of $C_{36}H_{69}NO_{10}Si_2$. Its molecular structure is as follows:

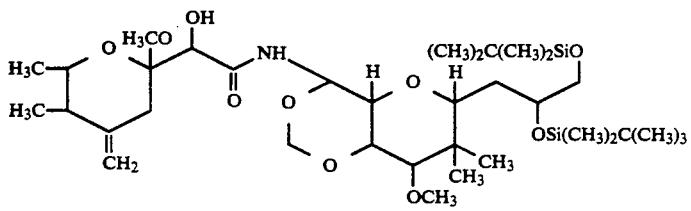

EXAMPLE 45

10-Epimycalamide A 7-Mono-Benzyl Ether

10-Epimycalamide A 7-Mono-Benzyl Ether has a molecular weight of 593 and a molecular formula of $C_{31}H_{47}NO_{10}$. Its molecular structure is as follows:

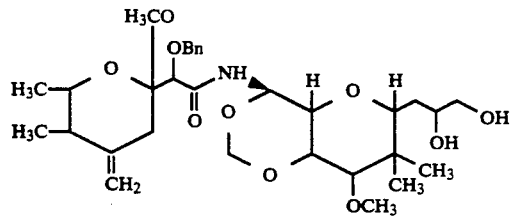

The compound is characterized as follows:

$^1$H NMR (CDCl3): δ 7.58 (NH9, d, 9.9), 5.74 (H10, t, 9.1), 10-OCH2, d, 6.9), 4.88 (4=CH2, m), 4.84 (10-OCH2, d, 6.8), 4.75 (4=CH2, t, 1.8), 4.23 (H7, s), 4.15 (H12, dd, 6.3, 9.7), 4.03 (H2, dq, 2.9, 6.6), 3.77 (H11, dd, 6.3, 8.8), 3.66 (H17, m), 3.59 (H18, dd, 4.2, 10.8), 3.54 (13-OCH3, s), 3.51 (H18, dd, 2.5, 10.7), 3.41 (H15, broad d, 9.9), 3.38 (H13, d, 9.5), 3.31 (6-OCH3, s), 2.38 (H5(eq), d, 14.1), 2.26 (H3, dq, 2.9, 7.0), 2.17 (H5(ax), broad d, 14.4), 1.80 (H16, ddd, 1.7, 9.9, 14.1), 1.55 (H16, m), 1.21 (2-CH3, d, 6.5), 1.02 (3-CH3, d, 7.0), 1.01 (14-CH3(eq), 0.89 (18-OSiC(CH3)3, s), 0.86 (14-CH3(ax), s), 0.83 (17-OSiC(CH3)3, s), 0.06 (18-OSi(CH3)2, s), −0.02 (17-OSi(CH3)2, 2xs) ppm (couplings in Hz).

$^{13}$C NMR (CDCl3): δ 171.34 (C8), 144.91 (C4), 111.35 (4=CH2), 99.93 (C6), 86.28 (10-OCH2), 79.86 (C13), 76.15 (C15), 74.17 (C10), 74.05 (C12), 71.80 (C7), 70.38 (C17), 70.10 (C11, broad), 69.71 (C2), 65.81 (C18), 61.58 (13-OCH3), 48.71 (6-OCH3), 41.42 (C3), 41.10 (C14), 33.49 (C5), 33.31 (C16), 26.03 and 25.89 (17- and 18-OSiC(CH3)3), 23.86 (14-CH3(eq)), 17.98 (2-CH3), 14.25 (14-CH3(ax), broad), 11.97 (3-CH3), −4.32 and −4.67 (17-OSi(CH3)2), −5.22 (18-OSi(CH3)2).

Mycalamide A 17,18-bis-TBDMS ether can be prepared as follows: Mycalamide A (2.6 mg), t-butyldimethylchlorosilane (large excess), dimethylaminopyridine (2 mg) and triethylamine (20 mg) were stirred in pyridine (0.4 ml) at 60° C. for 2 days. H2O (0.5 ml) was added and the mixture extracted with CH2Cl2. The organic extract was washed with H2O (3×0.3 ml), the solvent removed, and the combined product subjected to silica gel chromatography (200 mg Davisil, 150 Å, 35–70 μm), developed in steps from hexane to ethyl acetate. A minor fraction (1.5 mg) which eluted with 9:1 PE:EtOAc was mycalamide A tris-TBDMS ether, while the major fraction (2.5 mg) which eluted with 3:1 PE:EtOAc was pure mycalamide A 17,18-bis-TBDMS ether by PMR, an oil.

The compound is characterized as follows:

DCIMS (NH3): 611 (2%, M+NH4+), 594 (3%, MH+), 582 (9%), 581 (26%), 580 (28%), 579 (80%, M+NH4+—CH3OH), 565 (12%), 564 (37%), 563 (33%), 562 (100%, MH+—CH3OH).

$^1$H NMR (CDCl3): δ 7.77 (NH9, d, 9.3), 7.4–7.2 (φ, m), 5.46 (H10, dd, 2.1, 9.3), 5.07 (10-OCH2, d, 6.6), 4.83 (10-OCH2, d, 6.9), 4.81 (4=CH2, m), 4.80 (7-OCH2φ, d, 12.0), 4.71 (4=CH2, t, 1.9), 4.53 (7-OCH2φ, d, 11.3), 4.02 (H7, s), 3.89 (H2, dq, 2.7, 6.5), 3.81 (H11, t, 1.9), 3.75 (H12, dd, 1.7, 2.4), 3.65 (H17, m), 3.64 (H15, dd, 3.0, 12.9), 3.51 (H18, dd, 3.4, 11.0), 3.38 (13-OCH3, s), 3.33 (H18, dd, 7.5, 11.0), 3.19 (6-OCH3, s), 2.92 (H13, d, 2.4), 2.45 (H5(ax), td, 1.9, 14.4), 2.32 (H5(eq), d, 14.6), 2.25 (H16, ddd, 7.1, 12.1, 15.1), 2.19 (H3, dq, 2.9, 7.0), 1.44 (H16, ddd, 3.1, 5.0, 15.4), 1.21 (14-CH3(ax), s), 1.17 (2-CH3, d, 6.6), 0.99 (3-CH3, s, 7.0), 0.91 (14-CH3(eq), s) ppm (couplings in Hz).

$^{13}$C NMR (CDCl3): δ 169.81 (C8), 146.46 (C4), 137.26, 128.49, 128.38 and 127.98 (7-OCH2φ), 110.08 (4=CH2), 99.65 (C6), 91.59 (10-OCH2), 83.74 (C13), 81.28 (C7), 80.92 (C15), 77.2 (C10), 73.43 (7-OCH2), 72.69 (C12), 71.50 (C17), 69.66 (C2), 66.31 (C18), 61.81 (C11), 59.25 (13-OCH3), 49.59 (6-OCH3), 41.37 (C3), 36.65 (C14), 34.39 (C5), 30.41 (C16), 27.35 (14-CH3(ax)), 22.47 (14-CH3(eq)), 17.74 (2-CH3), 11.82 (3-CH3).

10-epimycalamide A 7-monobenzyl ether can be prepared as follows: Mycalamide A (6 mg), BaO (26 mg) and benzyl bromide (15 mg) were stirred in DMSO (0.3 ml) at 60° C. for 2 hours. H2O was added (0.5 ml) and the mixture transferred onto a reverse phase pipette column (200 mg C18, equilibrated to H2O), flushed with H2O (8 ml), then eluted with MeOH (6 ml). The resulting MeOH fraction was evaporated to dryness, then subjected to prep TLC (1:2 PE:EtOAc). Four bands of silica were recovered and each eluted with ethyl acetate to give four fractions (1 mg, 1 mg, 1.3 mg, 1.3 mg) which were mycalamide A and 10-epimycalamide A 7-monobenzyl ethers, and 10-epimycalamide A and mycalamide A 7,18-dibenzyl ethers by NMR respectively, an oil.

EXAMPLE 46

10-Epimycalamide A 7,18-Dibenzyl Ether

10-Epimycalamide A 7,18-Dibenzyl Ether has a molecular weight of 683 and a molecular formula of $C_{38}H_{53}NO_{10}$. Its molecular structure is as follows:

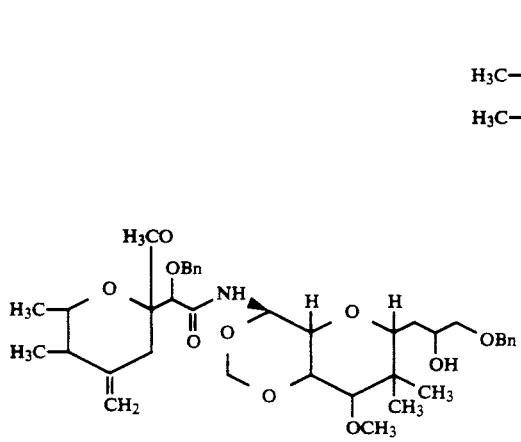

The compound is characterized as follows:

DCIMS (NH3): 701 (4%, M+NH4+), 672 (5%), 671 (18%), 670 (42%), 669 (100%, M+NH4+—CH3OH), 654 (11%), 653 (21%), 652 (53%, MH+—CH3OH).

1H NMR (CDCl3): δ 7.91 (NH9, d, 9.5), 7.4–7.2 (2x$\phi$, m), 5.43 (H10, dd, 2.1, 9.1), 5.05 (10-OCH2, d, 6.6), 4.82 (10-OCH2, d, 6.6), 4.81 (7-OCH2$\phi$, d, 11.6), 4.78 (4=CH2, t, 1.9), 4.67 (4=CH2, t, 1.9), 4.50 (18-OCH2$\phi$, d, 12.0), 4.48 (7-OCH2$\phi$, d, 11.4), 4.43 (18-OCH2$\phi$, d, 12.0), 3.99 (H7, s), 3.87 (H2, dq, 2.8, 6.6), 3.82 (H17, m), 3.78 (H11, t, 2.0), 3.74 (H12, dd, 1.9, 2.4), 3.58 (H15, dd, 3.2, 11.8), 3.40 (H18, dd, 3.6, 9.5), 3.37 (13-OCH3, s) 3.30 (H18, dd, 7.1, 9.4), 3.07 (6-OCH3, s), 2.91 (H13, d, 2.3), 2.44 (H5(ax), td, 1.9, 14.6), 2.35 (H5(eq), d, 14.1), 2.22 (H16, ddd, 6.7, 11.9, 15.0), 2.16 (H3, dq, 3.0, 7.3), 1.54 (H16, ddd, 3.3, 5.9, 15.2), 1.20 (14-CH3(ax), s), 1.13 (2-CH3, d, 6.6), 0.99 (3-CH3, d, 7.1), 0.91 (14-CH3(eq), s) ppm (couplings in Hz).

13C NMR (CDCl3): δ 170.03 (C8), 146.57 (C4), 137.71, 128.53, 128.40, 128.33, 127.89, 127.72 and 127.66 (7- and 18-OCH2$\phi$), 109.87 (4=CH2), 99.72 (C6), 91.42 (10-OCH2), 83.84 (C13), 80.48 (C15), 79.95 (C7), 77.26 (C10), 73.85 (C18), 73.31 and 73.25 (7- and 18-OCH2), 72.71 (C12), 69.69 (C17), 69.46 (C2), 61.54 (C11), 59.26 (13-OCH3), 48.83 (6-OCH3), 41.50 (C3), 36.64 (C14), 34.18 (C5), 30.71 (C16), 27.41 (14-CH3(ax)), 22.50 (14-CH3(eq)), 17.77 (2-CH3), 11.81 (3-CH3). NB: 1x$\phi$ not observed.

10-epimycalamide A 7,18-dibenzyl ether can be prepared as follows: Mycalamide A (6 mg), BaO (26 mg) and benzyl bromide (15 mg) were stirred in DMSO (0.3 ml) at 60° C. for 2 hours. H2O was added (0.5 ml) and the mixture transferred onto a reverse phase pipette column (200 mg C18, equilibrated to H2O), flushed with H2O (8 ml), then eluted with MeOH (6 ml). The resulting MeOH fraction was evaporated to dryness, then subjected to prep TLC (1:2 PE:EtOAc). Four bands of silica were recovered and each eluted with ethyl acetate to give four fractions (1 mg, 1 mg, 1.3 mg, 1.3 mg) which were mycalamide A and 10-epimycalamide A 7-monobenzyl ethers, and 10-epimycalamide A and mycalamide A 7,18-dibenzyl ethers by NMR respectively, an oil.

EXAMPLE 47

Mycalamide A Tris-TBDMS Ether

Mycalamide A Tris-TBDMS Ether has a molecular weight of 845 and a molecular formula of $C_{42}H_{83}NO_{10}Si_3$. Its molecular structure is as follows:

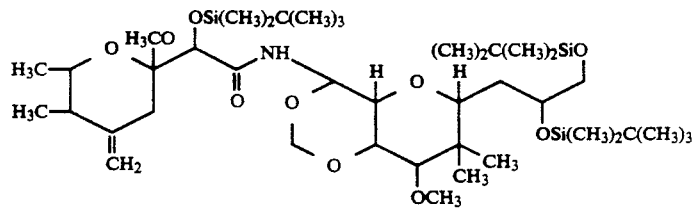

The compound is characterized as follows:

1H NMR (CDCl3): δ 7.30 (NH9, d, 9.7), 5.74 (H10, dd, 8.5, 9.7), 5.09 (10-OCH2, d, 6.9), 4.81 (4=CH2, t, 1.9), 4.81 (10-OCH2, d, 6.8), 4.71 (4=CH2, t, 1.9), 4.20 (H7, s), 4.11 (H12, dd, 6.0, 9.3), 3.86 (H2, dq, 2.6, 6.5), 3.71 (H11, dd, 6.1, 8.5), 3.71 (H17, m), 3.64 (H18, dd, 3.8, 11.3), 3.53 (H18, dd, 2.2, 11.3), 3.52 (13-OCH3, s), 3.41 (H15, dd, 1.6, 10.0), 3.36 (H13, d, 9.2), 3.29 (6-OCH3, s), 2.55 (H5(eq), d, 14.4), 2.36 (H5(ax), td, 2.0, 14.4), 2.19 (H3, dq, 2.5, 7.0), 1.83 (H16, ddd, 1.7, 10.2, 13.8), 1.5 (H16, m), 1.17 (2-CH3, d, 6.6), 1.01 (14-CH3(eq), s), 0.99 (3-CH3, d, 7.1), 0.94 (7-OSiC(CH3)3, s), 0.88 (18-OSiC(CH3)3, s), 0.87 (14-CH3(ax), s), 0.84 (17-OSiC(CH3)3, s), 0.17 and 0.13 (7-OSi(CH3)2, 2xs), 0.05 and −0.01 (17- and 18-OSi(CH3)2, 2xs) ppm (couplings in Hz).

13C NMR (CDCl3): δ 170.58 (C8), 146.65 (C4), 109.96 (4=CH2), 99.58 (C6), 86.13 (10-OCH2), 80.12 (C13), 77.13 (C7), 76.20 (C15), 73.76 (C12), 73.54 (C10), 70.38 (C17), 70.03 (C11, broad), 69.54 (C2), 65.60 (C18), 61.44 (13-OCH3), 50.10 (6-OCH3), 41.36 (C3), 40.89 (C14, broad), 35.79 (C5), 33.05 (C16), 26.02 and 25.90 (7-, 17- and 18-OSiC(CH3)3), 24.06 (14-CH3(eq)), 17.86 (2-CH3), 14.6 (14-CH3(ax), broad), 11.77 (3-CH3), −4.27, −4.43, −4.74, −4.84, −5.13 and −5.26 (7-, 17- and 18-OSi(CH3)2).

Mycalamide A tris-TBDMS ether can be prepared as follows: Mycalamide A (2.6 mg), t-butyldimethylchlorosilane (large excess), dimethylaminopyridine (2 mg) and triethylamine (20 mg) were stirred in pyridine (0.4 ml) at 60° C. for 2 days. H2O (0.5 ml) was added and the mixture extracted with CH2Cl2. The organic extract was washed with H2O (3×0.3 ml), the solvent removed, and the combined product subjected to silica gel chromatography (200 mg Davisil, 150 Å, 35–70 μm), developed in steps from hexane to ethyl acetate. A minor fraction (1.5 mg) which eluted with 9:1 PE:EtOAc was mycalamide A tris-TBDMS ether, while the major fraction (2.5 mg) which eluted with 3:1 PE:EtOAc was pure mycalamide A 17,18-bis-TBDMS ether by PMR, an oil.

EXAMPLE 48

7,17,18-Trimethoxy Mycalamide A 7,17,18-Trimethoxy Mycalamide A has a molecular weight of 545 and a molecular formula of $C_{27}H_{47}NO_{10}$. Its molecular structure is as follows:

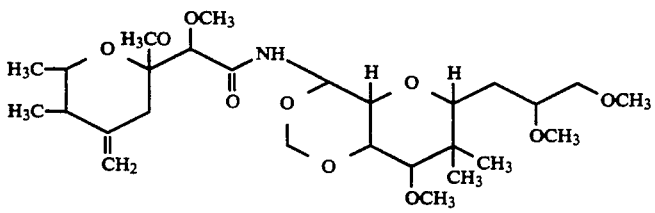

The compound is characterized as follows:

DCIMS (NH$_3$): 563 (10%, M+NH$_4^+$), 533 (18%), 532 (37%), 531 (100%, M+NH$_4^+$—CH$_3$OH), 516 (11%), 515 (22%), 514 (74%, MH$^+$—CH$_3$OH).

$^1$H NMR (CDCl$_3$): δ 7.13 (NH9, d, 9.6), 5.81 (H10, t, 9.8), 5.13 (10-OCH$_2$, d, 7.0), 4.82 (10-OCH$_2$, d, 7.0), 4.82 (4=CH$_2$, t, 1.9), 4.71 (4=CH$_2$, t, 1.9), 4.21 (H12, dd, 6.6, 10.4), 3.91 (H2, dq, 2.7, 6.5), 3.87 (H7, s), 3.84 (H11, dd, 6.6, 9.9), 3.55 (7-and 13-OCH$_3$, s), 3.45 (H18, m), 3.44 (H12, d, 10.2), 3.37 (18-OCH$_3$, s), 3.32 (H15, m), 3.31 (H18, m), 3.3 (H17, m), 3.29 (17-OCH$_3$, s), 3.28 (6-OCH$_3$, s), 2.43 (H5(ax), td, 2.0, 13.2), 2.30 (H5(eq), d, 14.2), 2.19 (H3, dq, 2.6, 7.2), 1.62 (H$_2$16, m), 1.16 (2-CH$_3$, d, 6.6), 0.97 (14-CH$_3$(eq), s), 0.97 (3-CH$_3$, d, 7.0), 0.87 (14-CH$_3$(ax), s) ppm (couplings in Hz).

$^{13}$C NMR (CDCl$_3$): δ 170.06 (C8), 146.20 (C4), 110.02 (4=CH$_2$), 99.91 (C6), 86.49 (10-OCH$_2$), 82.98 (C7), 79.48 (C13), 77.66 (C17), 75.81 (C15), 74.41 (C12), 73.11 (C10), 72.87 (C18), 70.59 (C11, broad), 69.39 (C2), 61.80 (13-OCH$_3$), 60.20 (7-OCH$_3$), 59.19 (18-OCH$_3$), 56.81 (17-OCH$_3$), 49.01 (6-OCH$_3$), 41.57 (C14), 41.42 (C3), 34.16 (C5), 29.83 (C16), 23.18 (14-CH$_3$(eq)), 17.82 (2-CH$_3$), 13.45 (14-CH$_3$(ax), broad), 11.80 (3-CH$_3$).

7,17,18-trimethoxy mycalamide A can be prepared as follows: Mycalamide A (4.2 mg), Ag$_2$O (25 mg) and MeI (18 mg), were stirred in benzene (0.3 ml) at 80° C. in a sealed vial for 3 days. The solution was filtered over celite and the solvent removed (4.6 mg). Preparative TLC (developed in EtOAc) gave three fractions (0.5 mg, 1.2 mg, 2.0 mg) which were 7,17-dimethoxy mycalamide A, 7,18-dimethoxy A and 7,17,18-trimethoxy A by NMR respectively. These were individually rechromatographed by prep. TLC to give the pure compounds, an oil.

EXAMPLE 49

7-Methoxy, N-Methyl Mycalamide B

7-Methoxy, N-Methyl Mycalamide B has a molecular weight of 545 and a molecular formula of C$_{27}$H$_{47}$NO$_{10}$. Its molecular structure is as follows:

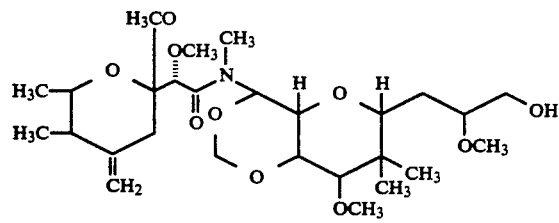

The compound is characterized as follows:

DCIMS (NH$_3$): 563 (2%, M+NH$_4^+$), 533 (9%), 531 (34%, M+NH$_4^+$—CH$_3$OH), 516 (25%), 514 (100%, MH$^+$—CH$_3$OH).

$^1$H NMR (CDCl$_3$): δ 6.26 (H10, d, 10.2), 5.16 (10-OCH$_2$, d, 6.7), 4.87 (10-OCH$_2$, d, 6.7), 4.83 (4=CH$_2$, m), 4.74 (4=CH$_2$, m), 4.29 (H12, dd, 7.0, 10.0), 4.25 (H7, s), 4.16 (H11, dd, 6.8, 9.8), 3.94 (H2, dq, 2.7, 6.3), 3.72 (H18, dd, 2.7, 11.8), 3.57 (13-OCH$_3$, s), 3.52 (H18, dd, 5.9, 11.3), 3.50 (H15, m), 3.48 (H13, d, 10.0), 3.46 (7-OCH$_3$, s), 3.31 and 3.30 (6-OCH$_3$ and 17-OCH$_3$, 2xs), 3.3 (H17, m), 3.22 (N-CH$_3$, s), 2.71 (H5(ax), broad d, 14.2), 2.28 (H5(eq), d, 14.1), 2.20 (H3, dq, 2.9, 7.0), 1.54 (H$_2$16, m), 1.14 (20CH$_3$, d, 6.5), 1.00 (3-CH$_3$, d, 7.0), 0.99 (14-CH$_3$(eq), s), 0.87 (14-CH$_3$(ax), s) ppm (couplings in Hz).

7-Methoxy, N-Methyl Mycalamide B can be prepared as follows: Mycalamide B (2 mg), powdered KOH (2 mg) and MeI (4.6 mg) were stirred in DMSO at room temperature for 24 hours. H$_2$O was added (0.3 ml), the mixture extracted with CH$_2$Cl$_2$ (3×0.4 ml), and the solvent removed (3 mg). Prep RPLC (30% H$_2$O in MeOH) gave two fractions (1.2 mg, 0.6 mg) which were pure 7-methoxy, N-methyl mycalamide B and 7,18-dimethoxy, N-methyl mycalamide B by PMR respectively, an oil.

Example 50

7'-Methoxy, N-Methyl Mycalamide B

7'-Methoxy, N-Methyl Mycalamide B has a molecular weight of 545 and a molecular formula of C$_{27}$H$_{47}$NO$_{10}$. Its molecular structure is as follows:

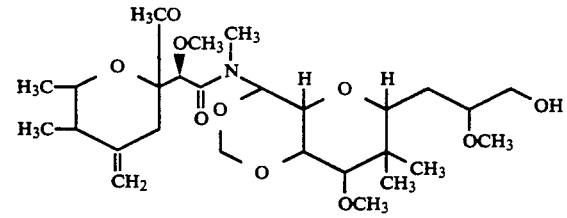

The compound is characterized as follows:

DCIMS (NH$_3$): 563 (3%, M+NH$_4^+$), 533 (5%), 532 (13%), 531 (45%, M+NH$_4^+$—CH$_3$OH), 516 (14%), 515 (28%), 514 (100%, MH$^+$—CH$_3$OH).

$^1$H NMR (CDCl$_3$): δ 6.32 (H10, d, 10.3), 5.13 (10OCH$_2$, d, 6.8), 4.85 (10-OCH$_2$, d, 6.8), 4.83 (4=CH$_2$, t, 2.0), 4.73 (4=CH$_2$, t, 2.1), 4.28 (H12, dd, 7.0, 10.7), 4.22 (H7, s), 4.09 (H11, dd, 7.1, 10.2), 3.94 (H2, dq, 2.6, 6.6), 3.72 (H18, dd, 2.5, 11.8), 3.61 (7-OCH$_3$, s), 3.55 (13-OCH$_3$, s), 3.54 (H18, m, hidden), 3.50 (H13, d, 10.8), 3.47 (H15, dd, 1.6, 8.6), 3.36 (17-OCH$_3$, s), 3.29 (6-OCH$_3$, s), 3.14 (N-CH$_3$, s), 3.12 (H17, m), 2.84 (H5(ax), td, 2.0, 14.9), 2.54 (H5(eq), d, 15.0), 2.20 (H3, dq, 2.3, 7.0), 1.58 and 1.45 (H$_2$16, m), 1.14 (2-CH$_3$, d, 6.5), 1.02 (3-CH$_3$, d, 7.0), 0.96 (14-CH$_3$(eq), s), 0.85 (14-CH$_3$(ax), s) ppm (couplings in Hz).

$^{13}$C NMR (CDCl$_3$): δ 146.98 (C4), 110.10 (4=CH$_2$), 102.04 (C6), 86.85 (10-OCH$_2$), 81.09 (C7), 79.73 (C17), 79.05 (C13), 75.84 (C15), 74.74 (C12), 69.63 (C2), 67.24 (C11), 65.70 (C18), 61.88 (13-OCH$_3$), 60.39 (7-OCH$_3$), 56.94 (17-OCH$_3$), 50.55 (6-OCH$_3$), 41.66 (C14), 41.35 (C3), 32.34 (C5), 30.83 (C16), 29.09 (N-CH$_3$), 23.00

(14-CH$_3$(eq)), 18.00 (2-CH$_3$), 12.94 (14-CH$_3$(ax)), 11.96 (3-CH$_3$). NB: C8, C10 not observed.

7'-methoxy, N-methyl Mycalamide B can be prepared as follows: 7-Methoxy, N-methyl mycalamide B (1.2 mg) was dissolved in a solution of 1M NaOMe in MeOH and stirred at 80° C. for two days. The solvent was removed, then the residue partitioned in 1:1 H$_2$O:CHCl$_3$ (4 ml), extracted in CHCl$_3$ (3×1 ml), and dried. The combined organic extract was subjected to silica gel chromatography (200 mg Davisil), developed in steps from PE to 5% EtOH:EtOAc. The major fraction eluted with 1:19 EtOH:EtOAc (0.9 mg) was a 1:3 mixture of starting material and its epimer at C7 by NMR. (Subsequent mixtures of the two epimers were combined (2 mg), treated as above, and purified by prep. TLC (developed twice in EtOAc) to give two fractions containing the pure epimers by PMR), an oil.

EXAMPLE 51

Biological Activity Evaluation Methodology

Preparation of splenocyte cell suspensions. Splenocyte suspensions were prepared from 8 to 15-week-old C57BL/6J and BALB/c female mice as follows: mice were sacrificed by cervical dislocation, spleens excised, and single-cell suspensions prepared by grinding the spleen with the plastic end of a sterile plunger of a 1-ml syringe in 10 ml of cold (4° C.) tissue culture medium (TCM) (RPMI 1640 medium, supplemented with 10% fetal calf serum, 100 U/ml penicillin, 100 µg/ml streptomycin, and 1.0 mM of 1-glutamine. The cell suspension was transferred to a sterile 15-ml centrifuge tube and allowed to stand for 5 minutes on ice to settle-out debris. The resulting supernatant was then transferred to another sterile centrifuge tube, and the cell concentration adjusted to 2×10$^6$ cells/ml dilution with TCM.

Preparation of human peripheral blood leukocyte (PBL) suspensions. Human peripheral blood suspensions were prepared from Leukotrap blood filters as follows: Leukotrap filters containing processed leukocytes from random, unrelated blood donors were obtained from the Indian River Blood Bank (Vero Beach, Fla.). Buffy-coat blood cell suspensions were recovered by reverse-flow phosphate-buffered saline purging and centrifugation for 15 minutes at 475× g. Buffy coats were removed, and 5 ml of the suspension was layered onto 5 ml of Histopaque gradient material. The Histopaque gradients were centrifuged at 475× g for 30 minutes. Lymphocytes were removed from the Histopaque-medium interface, and washed twice with 10 ml of PBS (Dulbecco's phosphate-buffered saline without CaCl$_2$ and MgCl$_2$.6H$_2$O). The final cell pellet was resuspended in TCM, and the cell concentration adjusted to 2×10$^6$ cells/ml.

Two way mixed lymphocyte reaction (MLR). The immunosuppressive properties of mycalamide A were evaluated using the two-way MLR, utilizing murine splenocytes and human PBL. For the murine MLR, splenocytes from C57Bl/6J and BALB/c mice were prepared as described above, and a volume of 0.100 µl of each cell suspension was added together to test and control wells of microtiter plates. Wells containing 0.20 ml of each cell suspension alone served as controls.

Dilutions of the drug to be tested were prepared in absolute EtOH and further diluted to the appropriate concentration in TCM and added directly to the wells containing splenocyte combinations. Additional solvent (EtOH) control wells were also prepared by adding the equivalent percentage of EtOH to each culture well. Plates were incubated at 37° C. in a 5% CO$_2$ humidified atmosphere for 88 hours. Following the incubation, 1.0 µCi of $^3$H-thymidine was added to each well, and the plates were returned to the incubator for 5 hours. The contents of each well were harvested onto glass-fiber filter strips, and the incorporation of $^3$H-thymidine was determined by a liquid scintillation counter. Similar conditions were utilized for MLR cultures using human peripheral blood lymphocytes prepared from unrelated donors as described above, with the exception that the initial incubation and subsequent $^3$H-thymidine pulse times were different (114 hours for initial incubation followed by a 6-hour incubation with $^3$H-thymidine). Plates were harvested in a similar manner, and $^3$H-thymidine incorporation determined as described above.

Determination of mycalamide A toxicity. The toxicity of mycalamide A on murine splenocytes and human PBL was determined using a colorimetric assay, based on the ability of viable cells to convert the colorless tetrazolium salt, 3-(4,5-dimethylthiazol-2yl)-2,5-diphenyl tetrazolium bromide (MTT) to a colored formazan product and trypan blue exclusion. For the colorimetric assay, a volume of 0.075 ml of an MTT solution (550 µg/ml of MTT in TCM) was added to test and control wells containing one of the populations of splenocytes or test wells and incubated for 5-6 hours following the initial incubation period. Microtiter plates were centrifuged at 100× g, supernatants carefully removed, and a volume of 0.20 ml of isopropyl alcohol was added to each well to dissolve the formazan crystals. The absorbance at 570 nm was determined for each well using an ELISA plate reader. Concentrations of mycalamide A that resulted in cell cultures exhibiting less than 65% of the control (no compound) response were considered as nontoxic. As an additional parameter of toxicity, wells containing cultured lymphocytes with various dilutions of mycalamide A were examined with trypan blue, and the percentage of dye-excluding (viable) cells was determined.

Mitogen studies. The effects of mycalamide A on the mitogen-induced proliferation of murine splenocytes was investigated. Splenocytes (2×10$^5$/well) from C57BL/6J or BALB/c mice were incubated with 1.0 µg/ml of Con A, 10 µg/ml of phytohemagglutinin (PHA), lipopolysaccharide (LPS) or pokeweed mitogen (PWM) and various concentrations of mycalamide A at 37° C. in a 5% CO, humidified atmosphere for 90 hours. A volume of 0.50 ml of a 20.0 µCi/ml of $^3$H-thymidine was added to each well, and the plates incubated for an additional 6 hours. Plates were harvested, and $^3$H-thymidine incorporation determined by counting samples in a liquid scintillation counter.

mB7-mediated activation of murine CD4+ T cells. Mouse T cells were purified as follows: splenocytes were depleted of red blood cells by treatment with Tris-NH$_4$Cl. T cells were enriched by nylon wool fractionation. CD4+ T cells from BALB/c mice were purified by two-fold treatment with a mixture of anti-MHC Class II and anti-CD8 monoclonal antibodies and rabbit complement. Chinese hamster ovary cells (CHO) and CHO cells transfected with the murine B7 molecule (CHOmB7) were fixed with 1% paraformaldehyde prior to addition to the cultures. Microcultures were set up in duplicate 96-well plates. 2×10$^5$ T cells were cultured with or without 2×10$^4$ paraformaldehyde-fixed CHO transfectants in 0.2 ml of RPMI 1640 supplemented with 10% FCS, 4 mM L-glutamine, 10 mM HEPES, $5 \times 10^{-5}$M 2 ME, antibiotics, and non-essential amino acids in the presence of 0.1 pM, 1.0 pM or 10 pM of mycalamide A and the indicated concentrations of anti-CD3 monoclonal antibody or indicated concentrations of phorbol 12, 13 myristate (PMA). Immunosuppressive standard compounds, FK506 and cyclosporin A (CsA) were also analyzed at various concentrations. All cultures were incubated for 48 hours and pulsed with 1 μCi $^3$H-thymidine/well for the last 6 hours of the incubation period to assay for T cell proliferation.

Graft vs. host reaction. In vivo studies with mycalamide A utilized the parenteral→$F_1$, GVHR model (Simonsen splenomegaly assay). CB6F$_1$ male mice, 4 weeks of age, were injected intraperitoneally with $5 \times 10^7$ splenocytes from BALB/c male mice, 8 weeks of age, on day 0 (BALB/c→CB6F$_1$). A syngeneic control group (CB6F$_1$→CB6F$_1$) was similarly prepared and served as the negative control. For experiment 1, the grafted mice were divided into 5 treatment groups of 5 mice each. Groups were injected intraperitoneally with mycalamide A (dissolved initially in ethanol followed by dilution in sterile phosphate-buffered saline as a vehicle) or vehicle alone on days 1–7. For experiment 2, the grafted mice were divided into 7 treatment groups of 5 mice each and similarly injected intraperitoneally with mycalamide A, an immunosuppressive standard, didemnin B, or vehicle alone on days 1–7. On day 7 all groups were sacrificed, spleens excised, and the mean spleen weight and stimulation index calculated for each group. The stimulation index was calculated as follows:

$$SI = \frac{\text{spleen wt. of test group/body wt. of test group}}{\text{spleen wt. of syngeneic group/body wt. of syngeneic group}} \times 100$$

A spleen index of 1.3 or greater is considered a positive response.

Allogeneic skin grafting. The effects of mycalamide A on the rejection of allogeneic skin grafts were determined using the BALB/c→CBA skin graft model. Skin grafts were prepared from BALB/c donors as follows: donors were sacrificed by cervical dislocation and hair shaved from back, sides, and torso. A depilatory agent was used to remove any remaining hair. The prepared skin area was then swabbed with a Betadine and alcohol solution. The skin was removed by making an incision at the base of the tail, and the skin was lifted and separated from the underlying muscle in two sections. The skin was then placed in a sterile petri dish containing sterile, ice cold normal saline. A sterile, #7 cord borer was used to punch out approximately 16 graft discs from each animal skin preparation. Recipient CBA mice were anesthetized with 1.5 cc ketamine:xylamine. The back of each recipient animal was shaved and a depilatory agent used to remove excess hair. The prepared area was swabbed with Betadine:alcohol, and a small plug of skin, approximately the size of the prepared grafts, was removed by excision. The skin graft plug was then placed in the center of the excised region and the resulting transplanted area sprayed with a barrier film (liquid skin). Animals were placed one to a cage and supplied with sterile food and water, ad libitum. Mice were observed each day for signs of rejection of the graft (a shrinking and thickening of the graft with eventual sloughing).

Results of Activity Assays

Immunosuppression of the two-way murine mixed lymphocyte response (MLR) by mycalamide A. Mycalamide A was evaluated for its ability to suppress the two-way murine mixed lymphocyte response, an in vitro correlation of the in vivo graft, graft vs. host response (GVHR). The results shown in Table 1 show that mycalamide A suppressed the MLR in a range of concentrations from $5 \times 10^2$ to $5 \times 10^{-16}$ μg/ml. The IC$_{50}$ of the mycalamide A for the MLR was $6.1 \times 10^{-17}$ μg/ml. The TC$_{50}$ of mycalamide A, as measured by the lymphocyte viability assay (LCV) was $5 \times 10^{-7}$ μg/ml. These results show that mycalamide A is a potent immunosuppressive agent in the MLR and its immunosuppressive activity is not correlated with a general cytotoxicity.

TABLE 1

Immunosuppression of the murine two-way mixed lymphocyte response by mycalamide A

| [a]Concentration of Mycalamide A | [b]% of Positive Control MLR | [c]% Viability (LCV) |
|---|---|---|
| $5.0 \times 10^2$ | 0 | 0 |
| $5.0 \times 10^1$ | 0 | 0 |
| $5.0 \times 10^0$ | 0 | 0 |
| $5.0 \times 10^{-1}$ | 0 | 55 |
| $5.0 \times 10^{-2}$ | 0 | 79 |
| $5.0 \times 10^{-3}$ | 0 | 66 |
| $5.0 \times 10^{-4}$ | 0 | 62 |
| $5.0 \times 10^{-5}$ | 0 | 63 |
| $5.0 \times 10^{-6}$ | 0 | 83 |
| $5.0 \times 10^{-7}$ | 0 | 71 |
| $5.0 \times 10^{-8}$ | 0 | 100 |
| $5.0 \times 10^{-9}$ | 0 | >99 |
| $5.0 \times 10^{-10}$ | 0 | >99 |
| $5.0 \times 10^{-11}$ | 0 | >99 |
| $5.0 \times 10^{-12}$ | 0 | >99 |
| $5.0 \times 10^{-13}$ | 0 | >99 |
| $5.0 \times 10^{-14}$ | 0 | >99 |
| $5.0 \times 10^{-15}$ | 0 | >99 |
| $5.0 \times 10^{-16}$ | 0 | >99 |
| $5.0 \times 10^{-17}$ | 85 | >99 |
| $5.0 \times 10^{-18}$ | 82 | >99 |
| $5.0 \times 10^{-19}$ | 128 | >99 |

[a]Concentration in μg/ml
[b]Percent of positive MLR control (no drug)
[c]Percent viability as measured by MTT Immunosuppression of mitogen induced proliferation of murine splenocytes by mycalamide A. Mycalamide A was assessed for its suppressive effects on mitogen induced stimulation of murine splenocytes. The results in Table 2 show that mycalamide A suppressed Con A, LPS, and PWM stimulation of murine splenocytes at $5 \times 10^{-5}$ μg/ml with no toxicity as measured by the LCV assay. Concentrations greater than $5 \times 10^{-5}$ μg/ml were toxic to the cells.

TABLE 2

Immunosuppression of mitogen induced proliferation of murine splenocytes by mycalamide A

| [a]Concentration of Mycalamide A | Con A [b]% of control | PHA % of control | LPS % of control | PWM % of control | LCV % viability |
|---|---|---|---|---|---|
| $5.0 \times 10^2$ | 0 | 0 | 0 | 0 | 3 |
| $5.0 \times 10^1$ | 0 | 0 | 0 | 0 | 2 |
| $5.0 \times 10^0$ | 0 | 0 | 0 | 0 | 1 |

TABLE 2-continued

| | Immunosuppression of mitogen induced proliferation of murine splenocytes by mycalamide A | | | | |
|---|---|---|---|---|---|
| [a]Concentration of Mycalamide A | Con A [b]% of control | PHA % of control | LPS % of control | PWM % of control | LCV % viability |
| $5.0 \times 10^{-1}$ | 0 | 0 | 0 | 0 | 4 |
| $5.0 \times 10^{-2}$ | 0 | 0 | 0 | 0 | 3 |
| $5.0 \times 10^{-3}$ | 0 | 0 | 0 | 0 | 3 |
| $5.0 \times 10^{-4}$ | 0 | 38 | 0 | 0 | 4 |
| $5.0 \times 10^{-5}$ | 0 | 139 | 68 | 62 | 180 |

[a]Concentration in µg/ml
[b]% of positive (no drug) control

Immunosuppression of the two-way human mixed lymphocyte response (MLR) by mycalamide A. Mycalamide A was evaluated for its ability to suppress the two-way human mixed lymphocyte response, an in vitro correlation of the in vivo graft vs. host response (GVHR). The results in Table 3 show that mycalamide A suppressed the human MLR with an $IC_{50}$ of $1.7 \times 10^{-5}$ µg/ml. The $TC_{50}$ of mycalamide A, as measured by the LCV, was $8.3 \times 10^{-2}$ µg/ml. These results show that mycalamide A is a potent immunosuppressive agent in the human MLR, and its immunosuppressive activity is not correlated with a general cytotoxicity.

TABLE 3

| Immunosuppression of the human two-way mixed lymphocyte response by mycalamide A | | |
|---|---|---|
| [a]Concentration of Mycalamide A | [b]% of Positive Control MLR | [c]% Viability (LCV) |
| $5.0 \times 10^{-1}$ | 0 | 42 |
| $5.0 \times 10^{-2}$ | 0 | 52 |
| $5.0 \times 10^{-3}$ | 0 | 46 |
| $5.0 \times 10^{-4}$ | 40 | 128 |
| $5.0 \times 10^{-5}$ | 43 | 111 |
| $5.0 \times 10^{-6}$ | 71 | 114 |
| $5.0 \times 10^{-7}$ | 81 | 116 |

[a]Concentration in µg/ml
[b]Percent of positive MLR control (no drug)
[c]Percent viability as measured by MTT Immunosuppression of mitogen induced proliferation of human peripheral blood lymphocytes (PBL) by mycalamide A. Mycalamide A was assessed for its suppressive effects on mitogen induced stimulation of human PBL. The results in Table 4 show that mycalamide A suppressed PHA and Con A stimulation of human PBL with $IC_{50}$ values of approximately $5.7 \times 10^{-6}$ and $5 \times 10^{-11}$ µg/ml, respectively. These results show that mycalamide suppresses mitogen responses of human PBL.

TABLE 4

| Immunosuppression of mitogen induced proliferation of human PBL by mycalamide A | | |
|---|---|---|
| [a]Concentation of Mycalamide A | Con A [b]% of control | PHA % of control |
| $5.0 \times 10^{0}$ | 0 | 0 |
| $5.0 \times 10^{-1}$ | 0 | 0 |
| $5.0 \times 10^{-2}$ | 0 | 0 |
| $5.0 \times 10^{-3}$ | 0 | 0 |
| $5.0 \times 10^{-4}$ | 10 | 9 |
| $5.0 \times 10^{-5}$ | 44 | 41 |
| $5.0 \times 10^{-6}$ | 74 | 41 |
| $5.0 \times 10^{-7}$ | 78 | 40 |
| $5.0 \times 10^{-8}$ | 82 | 43 |
| $5.0 \times 10^{-9}$ | 90 | 42 |
| $5.0 \times 10^{-10}$ | 99 | 36 |
| $5.0 \times 10^{-11}$ | 93 | 47 |

[a]Concentation in µg/ml
[b]% of positive (no drug) control

Figure 1B:
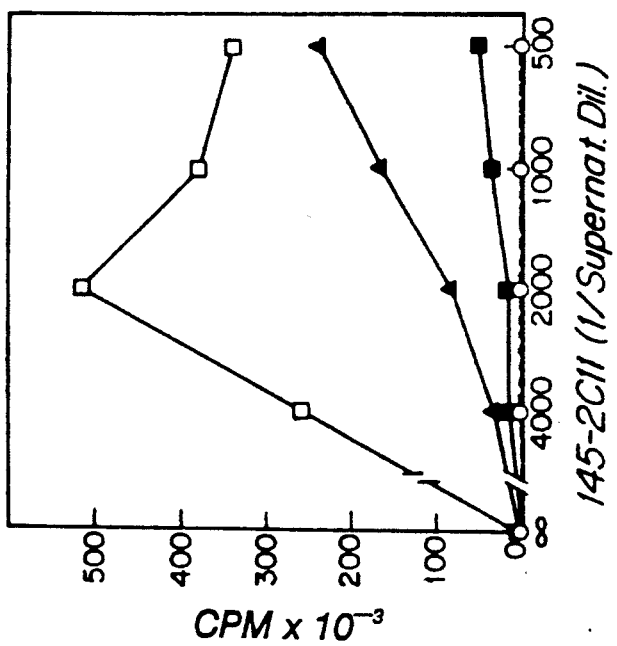
Figure 2A:
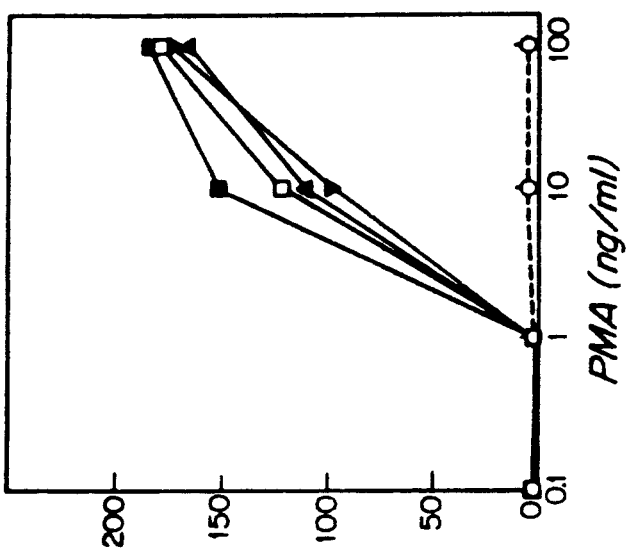
FIG. 2 shows that the effects of FK506 on mB7-mediated T cell activation parallel those of CsA. (A) Costimulation of T cells with anti-CD3 mAb and mB7. $2\times10^5$ purified BALB/c CD4+ T lymphocytes were stimulated with the indicated concentrations of anti-CD3 mAb in the presence of medium (◯), $2\times10^4$ paraformaldehyde-fixed CHO-mB7 cells (□), or $2\times10^4$ paraformaldehyde-fixed CHO-mB7 cells in the presence of 0.1 nM FK506 (▽), 1 nM FK506 (△), or 10 nM FK506 ( ). (B) Costimulation of T cells with mB7 and PMA. $2\times10^5$ purified BALB/c CD4+ T lymphocytes were stimulated with the indicated concentrations of PMA and either medium (◯), $2\times10^4$ paraformaldehyde-fixed CHO-mB7 cells (□), or paraformaldehyde-fixed CHO-mB7 cells in the presence of 0.1 nM FK506 (▽), 1 nM FK506 (△), or 10 nM FK506 ( ). All cultures were incubated for 48 hours and pulsed with 1 μCi [$^3$H] thymidine/well for the last 6 hours of the incubation period to assay for T cell proliferation.
Figure 2B:
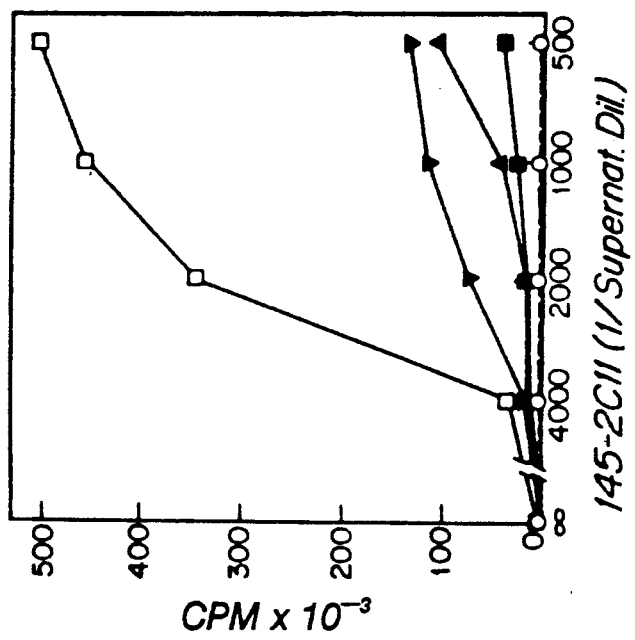
Figure 3A:
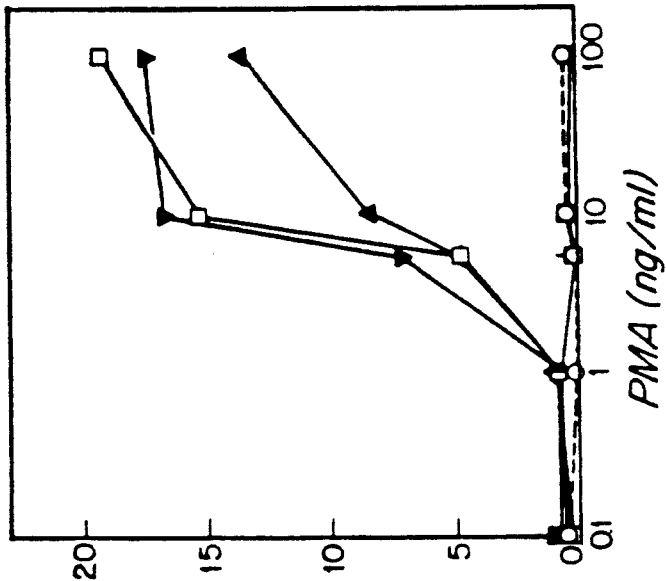
FIG. 3 shows that mycalamide A blocks activation of murine CD+ cells by anti-CD3 mAb and mB7 as well as activation by mB7 and PMA. (A) Costimulation of T cells with anti-CD3 mAb and mB7. $2\times10^5$ purified BALB/c CD4+ T lymphocytes were stimulated with the indicated concentrations of anti-CD3 mAb in the presence of medium (◯), $2\times10^4$ paraformaldehyde-fixed CHO-mB7 cells (□), or $2\times10^4$ paraformaldehyde-fixed CHO-mB7 cells in the presence of 0.1 pM mycalamide A (▽), 1 pM mycalamide A (△), or 10 pM mycalamide A ( ). (B) Costimulation of T cells with mB7 and PMA. $2\times10^5$ purified BALB/c CD4+ T lymphocytes were stimulated with the indicated concentrations of PMA and either medium (◯), $2\times10^4$ paraformaldehyde-fixed CHO-mB7 cells (□), or paraformaldehyde-fixed CHO-mB7 cells in the presence of 0.1 pM mycalamide A (▽), 1 pM mycalamide A (△), or 10 pM mycalamide A ( ). All cultures were incubated for 48 hours and pulsed with 1 μCi [$^3$H] thymidine/well for the last 6 hours of the incubation period to assay for T cell proliferation.
Figure 3B:
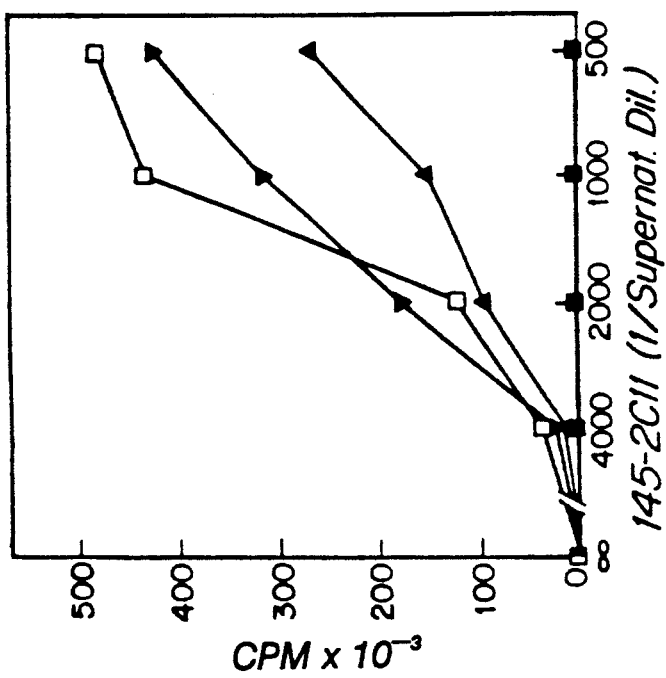

Mycalamide A blocks activation of murine CD4+ T cells by anti-CD3 mAb/mB7 and PMA/mB7. Mycalamide A was tested for its ability to block the activation of purified, CD4+ T cells by either anti-CD3/mB7 or PMA/mB7. FIG. 1a shows that the immunosuppressive standard, cyclosporin A (CsA), blocks the activation of CD4+ cells by anti-CD3/CHO-mB7 with an $IC_{50}$ of approximately 1.0 µM. Stimulation by PMA/CHO-mB7, however, is CsA-resistant (FIG. 1b). FIG. 2a shows that a second immunosuppressive standard, FK506, similarly blocks the anti-CD3/mB7 activation of CD4+ cells; however, the potency is approximately 100 times greater compared to CsA. The PMA/CHO-mB7 stimulation of CD4+ cells is similarly not affected by FK506 (FIG. 2b). FIGS. 3a and 3b show that mycalamide A blocked both the anti-CD3/mB7 (FIG. 3a) and PMA/mB7 (FIG. 3b) induced activation of CD4+ T cells with $IC_{50}$ values of approximately 1.0 pM each. This demonstrates that mycalamide A is 10 times more potent than FK506 and approximately 1000 times more potent than cyclosporin A in regards to its immunosuppressive activity. Incubation of T cells with mycalamide A did not significantly affect the cell viability as assessed by trypan blue exclusion (Table 5). These results indicate the mycalamide A is a potent immunosuppressive agent with suppressive activity which is superior to FK506 or CsA.

TABLE 5

| Effect of CsA, FK506, and mycalamide A on T cell viability[a] | | |
|---|---|---|
| Treatment | Experiment 1 | Experiment 2 |
| none | $1.59 \times 10^6$ (<2%) | $1.39 \times 10^6$ (<2%) |
| CsA 0.1 µg/ml | $1.48 \times 10^6$ (<2%) | $1.67 \times 10^6$ (<2%) |
| CsA 1 µg/ml | $1.36 \times 10^6$ (<2%) | $1.59 \times 10^6$ (<2%) |
| FK506 1 nM | $1.40 \times 10^6$ (<2%) | $1.64 \times 10^6$ (<2%) |
| Mycalamide A 1 pM | $1.39 \times 10^6$ (<2%) | $1.45 \times 10^6$ (<2%) |
| Mycalamide A 5 pM | $1.41 \times 10^6$ (<2%) | $1.68 \times 10^6$ (<2%) |
| Mycalamide A 10 pM | N.D. | $1.49 \times 10^6$ (<2%) |

[a]Approximately $1.5 \times 10^6$ T cells were seeded out in 1 ml of culture medium. Compounds were added as indicated. Cells were harvested 20 hours after initiation of the culture. Indicated in the table is the number of cells excluding trypan blue and, in parentheses, the percentage of trypan blue-positive cells. Each data point represents the mean value of two independent cultures.

Immunosuppression of the graft vs. host reaction (GVHR) by mycalamide A. Mycalamide A was evaluated for its in vivo immunosuppressive effects on the GVHR using the Simonsen splenomegaly assay. The results of two studies, presented in Table 6, demonstrate that mycalamide A suppressed the splenomegaly response of CB6F$_1$ mice grafted with allogeneic splenocytes when mice were treated with 0.01 mg/kg, intraperitoneally for 7 days (102% and 88% suppression, respectively). Dosages higher than 0.01 mg/kg were toxic. Dosages lower than 0.01 mg/kg were not immunosuppressive. These results demonstrate that mycalamide A is a potent immunosuppressive agent in vivo.

TABLE 6

Immunosuppressive effect of mycalamide A on the graft vs. host response

| Treatment[a] | No. of mice[b] | Stim. index[c] | % Suppression[d] |
|---|---|---|---|
| Experiment #1 | | | |
| Mycalamide A (0.1 mg/kg) | 0/5 | ND | 0 |
| Mycalamide A (0.05 mg/kg) | 0/5 | ND | 0 |
| Mycalamide A (0.01 mg/kg) | 5/5 | 0.99 | 102 |
| Positive (vehicle) | 5/5 | 1.30 | 0 |
| Syngeneic | 5/5 | 1.0 | 0 |
| Experiment #2 | | | |
| Mycalamide A (0.1 mg/kg) | 0/5 | ND | 0 |
| Mycalamide A (0.05 mg/kg) | 0/5 | ND | 0 |
| Mycalamide A (0.01 mg/kg) | 5/5 | 1.06 | 88 |
| Mycalamide A (0.005 mg/kg) | 5/5 | 1.92 | 0 |
| Didemnin B (0.2 mg/kg)[e] | 5/5 | 0.93 | 113 |
| Positive (vehicle) | 5/5 | 1.54 | 0 |
| Syngeneic | 5/5 | 1.0 | 0 |

[a]CB6F$_1$ mice (5 per group) were grafted with $5 \times 10^7$ BALB/c splenocytes, intraperitoneally on Day 0. Groups were injected intraperitoneally with drug or vehicle on Days 1–7. Positive indicates grafted mice receiving vehicle alone.
[b]Number of surviving mice at the end of the experiment.
[c]Stimulation index (SI) = (spleen weight of test group/body weight of test group)/(spleen weight of syngeneic group/body weight of syngeneic group).
[d]Suppression = [(SI of positive control) - (SI of test group)]/[(SI of positive control) - (SI of syngeneic group)].
[e]Didemnin B immunosuppressive standard.

Immunosuppression of allogenic skin graft rejection by mycalamide A. Mycalamide A was evaluated for its in vivo immunosuppressive effects on the rejection of allogeneic skin grafts using the BALB/c→CBA murine model. The results in Table 7 show that mycalamide A treatment of mice (0.01 mg/kg, twice daily, intraperitoneally for 14 days) suppressed the normal rejection of allogeneic skin grafts as indicated by a prolonged survival of the grafts, with a mean rejection time of 17.8 days. As a comparison, mice treated with an immunosuppressive standard, CsA, had a mean rejection time of 16.4 days. Untreated, grafted mice, however, all rejected their skin grafts by day 5. These results indicate that mycalamide A effectively suppresses the rejection of allogeneic skin grafts.

TABLE 7

In vivo suppression of allogeneic skin graft rejection by mycalamide A

| [a]Compound/treatment | | No. of mice | [b]Day of Death | [c]Graft Scores [d]Day (0, +) | | % Alive |
|---|---|---|---|---|---|---|
| Positive | QD1 × 14, IP | 3 | | D5 | (0) | 100 |
| CsA (50 mg/kg) | QD1 × 14, IP | 5 | 4, 9, 9, 21, 39 | D39 | (+) | 0 |
| Mycal. A (0.01 mg/kg) | Q2D × 7, 1–14 IP | 5 | 10, 11, 11, 22, 35 | D35 | (+) | 0 |

[a]Recipient CBA mice received skin grafts from BALB/c mice on Day 0. Mice injected, intraperitoneally (IP), beginning on Day 1 according to the indicated schedule.
[b]Day of death of each animal.
[c]0 = rejection, + = no rejection.
[d]Day of sacrifice of remaining mice.

EXAMPLE 52

Uses, Formulations, and Administrations

Therapeutic and prophylactic application of the mycalamide compounds, and compositions comprising them, can be accomplished by any suitable method and technique presently or prospectively known to those skilled in the art. Further, the compounds of the invention have use as starting materials or intermediates for the preparation of other useful compounds and compositions. The compounds of the invention are useful for various non-therapeutic and therapeutic purposes. It is apparent from the testing that the compounds of the invention have effective immunomodulatory activity. Specifically, they are useful in regulating immune responses in animals and humans.

The administration of the mycalamide compounds of the invention is useful as an immunomodulatory agent. Thus, pharmaceutical compositions containing compounds of the invention as active ingredients are useful in prophylatic or therapeutic treatment of an immunomodulatory response in humans or other mammals.

An intended use is for immune reactions (in vivo/in vitro) that require modulation via T cell activity. One aspect of the subject invention concerns human in vivo suppression of T cell response, e.g., transplantation and autoimmunity.

The dosage administered will be dependent upon the immunomodulatory response desired; the type of host involved; its age, health, weight, kind of concurrent treatment, if any; frequency of treatment; therapeutic ratio and like considerations. Advantageously, dosage levels of the administered active ingredients can be, for examples, dermal, 1 to about 500 mg/kg; orally, 0.01 to 200 mg/kg; intranasal 0.01 to about 100 mg/kg; and aerosol 0.01 to about 50 mg/kg of animal body weight.

Expressed in terms of concentration, the active ingredient of the invention can be present in the new compositions for localized use dermally, intranasally, bronchially, intramuscularly, intravaginally, intravenously, or orally in a concentration of from about 0.01 to about 50% w/w of the composition, and especially from about 0.1 to about 30% w/w of the composition.

The compositions of the invention are advantageously used in a variety of forms, e.g., tablets, ointments, capsules, pills, powders, aerosols, granules, and oral solutions or suspensions and the like containing the indicated suitable quantities of the active ingredient. Such compositions are referred to herein and in the accompanying claims generically as "pharmaceutical compositions." Typically, they can be in unit dosage form, namely, in physically discrete units suitable as unitary dosages for human or animal subjects, each unit containing a predetermined quantity of active ingredient calculated to produce the desired therapeutic or prophylactic effect in association with one or more pharmaceutically acceptable other ingredients, e.g., diluent or carrier.

Where the pharmaceutical compositions are aerosols, the active ingredients can be packaged in pressurized aerosol containers with a propellant, e.g., carbon dioxide, nitrogen, propane, etc. with the usual adjuvants such as cosolvents, wetting agents, etc.

Where the pharmaceutical compositions are ointments, the active ingredient can be mixed with a diluent vehicle such as cocoa butter, viscous polyethylene glycols, hydrogenated oils, and such mixtures can be emulsified if desired.

In accordance with the invention, pharmaceutical compositions comprise, as an active ingredient, an effective amount of one or more non-toxic, pharmaceutically acceptable ingredient(s). Examples of such ingredients for use in the compositions include ethanol, dimethyl sulfoxide, glycerol, silica, alumina, starch, calcium carbonate, talc, flour, and equivalent non-toxic carriers and diluents.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for treating a transplant patient by effecting immune suppression in said patient, said method comprising administering to said patient a therapeutically effective amount of a compound selected from the group consisting of:
   (a) mycalamide B 7-monobenzyl ether;
   (b) 7,7,18-trimethoxy, N-methyl mycalamide A;
   (c) 7,18-dimethoxy, N-methyl mycalamide A;
   (d) 7-methoxy, N-methyl mycalamide A;
   (e) mycalamide A 17,18-Di-p-bromobenzoate;
   (f) 7',17,18-trimethoxy, N-methyl mycalamide A;
   (g) mycalamide B trans-oxazolidinone;
   (h) mycalamide B cis-oxazolidinone;
   (i) mycalamide B bis-ethylcarbonate hydrochloride;
   (j) mycalamide B 7-mono-p-bromobenzoate;
   (k) mycalamide B 18-mono-p-bromobenzoate;
   (l) mycalamide B Di-p-bromobenzoate;
   (m) mycalamide B 7,N-dibenzyl ether;
   (n) mycalamide B 7,18-dibenzyl ether;
   (o) mycalamide B 7,18,N-tribenzyl ether;
   (p) mycalamide B 7,8,18-tribenzyl ether;
   (q) mycalamide A 7,N-dibenzyl ether;
   (r) mycalamide A 7,18-dibenzyl ether;
   (s) mycalamide A 7-monobenzyl ether;
   (t) mycalamide A 7,18,N-tribenzyl ether;
   (u) 7'-deutero, 7'-methoxy, N-methyl mycalamide A;
   (v) 7-epimycalamide A trans-oxazolidinone;
   (w) 7-epimycalamide A cis-oxazolidinone;
   (x) neomycalamide A triacetate;
   (y) mycalamide A tri-p-bromobenzoate;
   (z) mycalamide cis-oxazolidinone;
   (aa) mycalamide A trans-oxazolidinone;
   (bb) 10-epimycalamide A 7-monobenzyl ether;
   (cc) 10-epimycalamide A 7,18-dibenzyl ether;
   (dd) 7-methoxy, N-methyl mycalamide B;
   (ee) 7'-methoxy, N-methyl mycalamide B;
   (ff) mycalamide A; and
   (gg) mycalamide B.

2. A method for treating a transplant patient by effecting immune suppression in said patient said method comprising administering a therapeutically effective amount of a compound to said patient, said compound having the following structural formula:

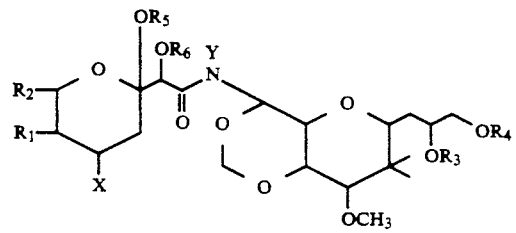

wherein $R^1$ and $R^2$ are the same or different and are hydrogen or lower alkyl, particularly C1–C5 alkyl; $R^{3-6}$ are the same or different and are hydrogen, lower alkyl, acyl, lower alkyl silyl, Bn, or Bz; X is $=CH_2$, $-CH_3$, or $-O-CH_2$; and Y is lower alkyl, Bn, or Bz.

3. The method according to claim 1, wherein said method comprises administering the compound as a pharmaceutical composition, said pharmaceutical composition comprising said compound and an acceptable pharmaceutical carrier.

* * * * *

UNITED STATES PATENT AND TRADEMARK OFFICE
CERTIFICATE OF CORRECTION

PATENT NO. : 5,298,523
DATED : March 29, 1994
INVENTOR(S) : Ross E. Longley, Glynn T. Faircloth It is certified that error appears in the above-indentified patent and that said Letters Patent is hereby corrected as shown below:

Column 3: lines 11, 17, 30, 36, 50, and 57: "CsA ( )" should read --CsA (■)--.

Column 7: line 2: "1213" should read --12.13--.

Column 10: structure:

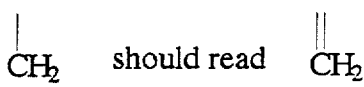

Column 16: line 67: "(4=$H_2$, m)" should read --(4=$CH_2$, m)--.

Column 33: lines 4 and 5:

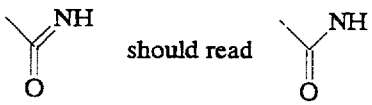

Column 35: lines 52-55:

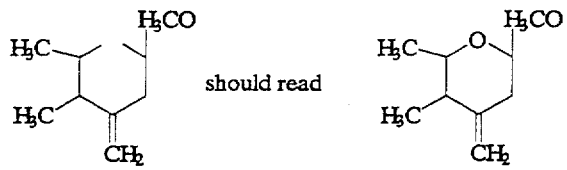

UNITED STATES PATENT AND TRADEMARK OFFICE
CERTIFICATE OF CORRECTION

PATENT NO. : 5,298,523
DATED : March 29, 1994
INVENTOR(S) : Ross E. Longley, Glynn T. Faircloth It is certified that error appears in the above-indentified patent and that said Letters Patent is hereby corrected as shown below:

Column 41: lines 30-35:

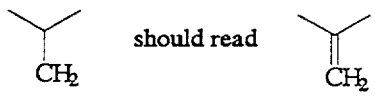

line 45: "(4=CH$_2$t, 1.9)" should read --(4=CH$_2$, t, 1.9)--.

Column 43: lines 15-30:

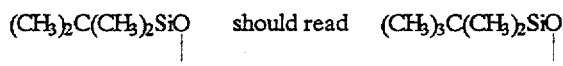

Column 46: lines 14-20:

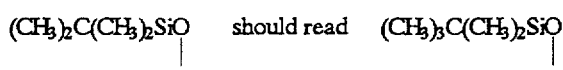

Signed and Sealed this

Sixth Day of September, 1994

BRUCE LEHMAN

Attest:

*Attesting Officer*     *Commissioner of Patents and Trademarks*